US010801055B2

(12) United States Patent
Young et al.

(10) Patent No.: US 10,801,055 B2
(45) Date of Patent: Oct. 13, 2020

(54) METHODS AND DEVICES FOR REAL-TIME DIAGNOSTIC TESTING (RDT) FOR EBOLA AND OTHER INFECTIOUS DISEASES

(71) Applicant: Theranos, Inc., Palo Alto, CA (US)

(72) Inventors: Daniel Young, Palo Alto, CA (US); Elizabeth A. Holmes, Palo Alto, CA (US)

(73) Assignee: Labrador Diagnotstics LLC, Wilmington, DE (US)

( * ) Notice: Subject to any disclaimer, the term of this patent is extended or adjusted under 35 U.S.C. 154(b) by 27 days.

(21) Appl. No.: 15/162,216

(22) Filed: May 23, 2016

(65) Prior Publication Data

US 2016/0281131 A1    Sep. 29, 2016

Related U.S. Application Data

(63) Continuation of application No. PCT/US2015/054618, filed on Oct. 8, 2015.

(60) Provisional application No. 62/061,671, filed on Oct. 8, 2014, provisional application No. 62/062,808, filed on Oct. 10, 2014, provisional application No. 62/077,011, filed on Nov. 7, 2014, provisional application No. 62/077,016, filed on Nov. 7, 2014, provisional application No. 62/094,848, filed on Dec. 19, 2014, provisional application No. 62/094,856, filed on Dec. 19, 2014.

(51) Int. Cl.
*C12Q 1/70* (2006.01)
*C12Q 1/6804* (2018.01)
*G01N 33/569* (2006.01)
*G01N 33/68* (2006.01)

(52) U.S. Cl.
CPC .............. *C12Q 1/6804* (2013.01); *C12Q 1/70* (2013.01); *G01N 33/56983* (2013.01); *G01N 33/6854* (2013.01); *G01N 2333/08* (2013.01); *G01N 2469/20* (2013.01)

(58) Field of Classification Search
None
See application file for complete search history.

(56) References Cited

U.S. PATENT DOCUMENTS

| 4,810,096 | A  | 3/1989  | Russell et al.    |
|-----------|----|---------|-------------------|
| 5,005,981 | A  | 4/1991  | Schulte et al.    |
| 5,055,263 | A  | 10/1991 | Meltzer           |
| 5,112,574 | A  | 5/1992  | Horton            |
| 6,143,252 | A  | 11/2000 | Haxo, Jr. et al.  |
| 6,290,907 | B1 | 9/2001  | Takahashi et al.  |
| 7,172,897 | B2 | 2/2007  | Blackburn et al.  |
| 8,088,593 | B2 | 1/2012  | Burd et al.       |
| 8,133,671 | B2 | 3/2012  | Williams et al.   |
| 8,669,047 | B2 | 3/2014  | Holmes et al.     |
| 2007/0087008 | A1 | 4/2007 | Hodge et al.    |
| 2011/0143947 | A1 | 6/2011 | Chamberlin et al. |
| 2013/0115685 | A1 | 5/2013 | Holmes et al.   |
| 2014/0186238 | A1 | 7/2014 | Holmes et al.   |
| 2014/0234949 | A1 | 8/2014 | Wasson et al.   |

FOREIGN PATENT DOCUMENTS

| WO | 2011094577 A3 | 11/2011 |
| WO | 2013096817 A2 | 6/2013  |

OTHER PUBLICATIONS

510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Diamandis. Theranos phenomenon: promises and fallacies. Clin Chem Lab Med. Jun. 2015;53(7):989-93.
Drosten et al. Rapid detection and quantification of RNA of Ebola and Marburg viruses, Lassa virus, Crimean-Congo hemorrhagic fever virus, Rift Valley fever virus, dengue virus, and yellow fever virus by real-time reverse transcription—PCR, J Clin Microbiol, Feb. 2002, 40(7), 2323-2330.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/5969923/Theranos_Inc_Cover_Letter_01-25-2016.0.pdf.
International Search Report and Written Opinion dated Jan. 12, 2016 for PCT/US2015/054618.
Ksiazek et al. ELISA for the detection of antibodies to Ebola viruses, J Infect Dis, Feb. 1999, 179 Suppl 1, S192-S198.
Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Plebani. Evaluating and using innovative technologies: a lesson from Theranos? Clin Chem Lab Med. Jun. 2015;53(7):961-2.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb. 8, 2016. http://www.beckershospitalreview.com/hospital-management-adminstration/theranos-gets-extension-to-fix-issues-following-cms-investigation.html.

(Continued)

*Primary Examiner* — Benjamin P Blumel

(57) ABSTRACT

Methods, devices, systems, and kits for use in detecting and measuring infectious diseases are provided. In particular embodiments, methods, devices, systems, and kits for detecting and measuring Ebola virus, including Ebola Zaire strain virus, are provided. Devices and systems may be used within regions suffering from Ebola or other infections, providing local, rapid, and effective diagnosis of infectious diseases such as Ebola, improving treatment and reducing or preventing spread of such infectious diseases.

20 Claims, 9 Drawing Sheets

Specification includes a Sequence Listing.

(56) References Cited

OTHER PUBLICATIONS

Abbott. FDA Clears Abbott's i-STAT 1 Wireless Point of Care Testing System. Press release dated Mar. 29, 2011.
Abbott. Procedure Manual for the i-STAT System. Rev. dated Jul. 12, 2004.
Abbott. Testing Cartridges for the i-STAT System. Rev. B. 06/09. Available at http://www.abbottpointofcare.com/PDFs/17845_CrtrdgeBrochure_M1.pdf. Accessed Sep. 13, 2011.
AppliedBiosystems StepOne Real-Time PCR System Manual, Rev. 2010.
BD Max System User's Manual, Sep. 2012.
Craw et al. Isothermal nucleic acid amplification technologies for point-of-care diagnostics: a critical review, Lab on a Chip, vol. 12, No. 14, Jul. 1, 2012.
Lounsbury et al., Lab Chip, 2013, 13, pp. 1384-1393.
Mahony et al. Molecular diagnosis of respiratory virus infections. Crit Rev Clin Lab Sci. Sep.-Dec. 2011;48(5-6):217-49.
Metzgar D. et al. Single assay for simultaneous detection and differential identification of human and avian influenza virus types, subtypes, and emergent variants. PLoS One. Feb. 3, 2010;5(2):e8995.
Niemz, et al. Nucleic acid testing for tuberculosis at the point-of-care in high-burden countries. Expert Rev Mol Diagn. Sep. 2012; 12(7): 687-701.
*SEC* vs. *Holmes*, et al: "Complaint", Mar. 14, 2018.
Chen et al. Development of a Generic Mirofluidic Device for Simultaneous Detection of Antibodies and Nucleic Acids in Oral Fluids, Biomed Research International, vol. 2013, Jan. 1, 2013, pp. 1-12.
Kurosaki et al. Rapid and simple detection of Ebola virus by reverse transcription-loop-mediated isothermal amplification, Journal of Virological Methods 141 (2007) 78-83.
Towner et al. Rapid Diagnosis of Ebola Hemorrhagic Fever by Reverse Transcription-PCR in an Outbreak Setting and Assessment of Patient Viral Load as a Predictor of Outcome, Journal of Virology, vol. 78, No. 8, Apr. 15, 2004, pp. 4330-4341.
You et al. Evaluating the Utility of Rapid Point-of-Care Potassium Testing for the Early Identification of Hyperkalemia in Patients with Chronic Kidney Disease in the Emergency Department, Yonsei Medical Journal, vol. 55, No. 5, Jan. 1, 2014, p. 1348.

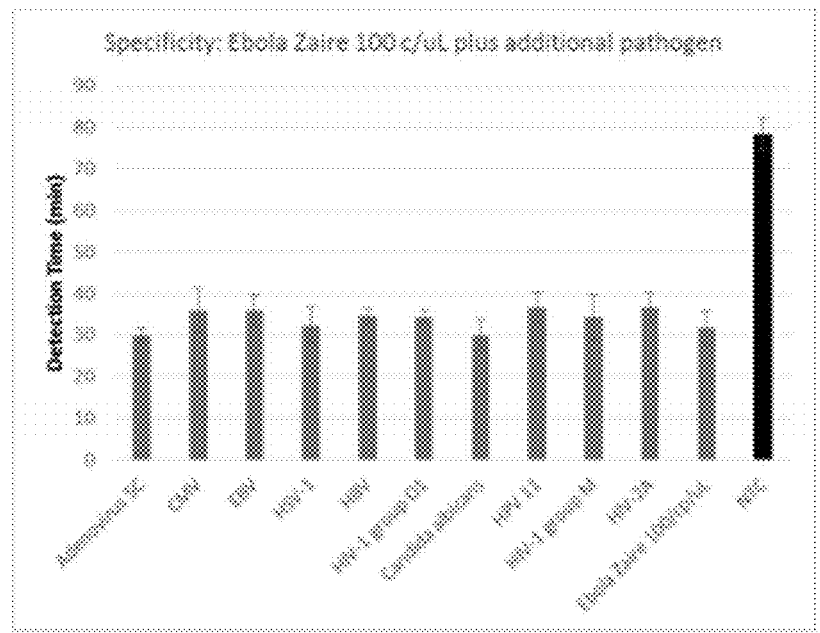

Fig. 5

| Blood Interfering Substance Panel | | | | | | | |
|---|---|---|---|---|---|---|---|
| Substance | 1x Concentration | Inhibits True Positive | Causes False Positives | 0.1x Concentration | Inhibits True Positive | Causes False Positives |
| hemoglobin | 5 g/L | N | Y | 0.5 g/L | N | N |
| triglycerides | 1430 mg/dL | N | N | 143 mg/dL | N | N |
| BSA | 120 g/L | N | N | 12 g/L | N | N |
| EDTA, pH 8.0 (anticoagulant) | 10 mg/mL | N | N | 1 mg/mL | N | N |
| heparin sodium salt (anticoagulant) | 106 U/mL | Y | N | 10.6 U/mL | Y | N |
| cholesterol | 13 mmol/L | N | N | 1.3 mmol/L | N | N |
| γ-globulin | 60 g/L | N | N | 6 g/L | N | N |
| universal transfer media (viral) | 50% v/v | N | N | 5% v/v | N | N |
| Amies transfer media (bacteria) | 50% v/v | N | N | 5% v/v | N | N |
| BACTEC™ Plus Anaerobic/F Medium | 50% v/v | N | N | 5% v/v | N | N |
| BACTEC™ Standard/10 Aerobic/F Medium | 50% v/v | N | N | 5% v/v | N | N |
| bilirubin | 684 μmol/L | N | N | 68.4 μmol/L | N | N |
| hgDNA | 200 ng/mL | N | N | 20 ng/mL | N | N |
| ampicillin sodium salt | 152 μmol/L | N | N | 15.2 μmol/L | N | N |
| Bactrim (1:5 trimethoprim:sulfamethoxazole) | 308 μmol/L | N | N | 30.8 μmol/L | N | N |
| azithromycin | 1.38 mg/mL | N | N | 0.138 mg/mL | N | N |
| nicotine/cotinine | 6.2 μmol/L; 10.8 μmol/L | N | N | 0.62 μmol/L; 1.08 μmol/L | N | N |
| DNA/RNA shield | 50% v/v | N | N | 5% v/v | N | N |

| Antibody | Result |
|---|---|
| Human anti-ZEBOV GP mab (KZ52) | Reactive |
| Rabbit anti-ZEBOV L pab | Reactive |
| Rabbit anti-ZEBOV NP pab | Reactive |
| Rabbit anti-ZEBOV VP35 pab | Reactive |
| Rabbit anti-ZEBOV VP40 pab | Reactive |
| Mouse anti-MMARV GPdTM mab | Non-Reactive |
| R-H Bundibugyo GP Pab | Non reactive |
| R-H Reston GP Pab | Non-Reactive |
| R-H Sudan GP Pab | Weakly reactive |
| M-H Sudan GPdTM mab (2H5) | Weakly reactive |
| M-H MMARV GP mab | Non-Reactive |

| Antigen | Result |
|---|---|
| ZEBOV GP | Reactive |
| ZEBOV NP | Non-Reactive |
| ZEBOV VP40 | Non-Reactive |
| MMARV GP | Non-Reactive |
| Bundibugyo GP | Non-Reactive |
| Reston GP | Non-Reactive |
| Sudan GP | Non-Reactive |
| Angola MARV GP | Non-Reactive |

Fig. 9B

METHODS AND DEVICES FOR REAL-TIME DIAGNOSTIC TESTING (RDT) FOR EBOLA AND OTHER INFECTIOUS DISEASES

CROSS-REFERENCE TO RELATED APPLICATIONS

This application claims the benefit of, and priority to, U.S. Patent Application 62/061,671, filed Oct. 8, 2014; U.S. Patent Application 62/062,808, filed Oct. 10, 2014; U.S. Patent Application 62/077,011, filed Nov. 7, 2014; U.S. Patent Application 62/077,016, filed Nov. 7, 2014; U.S. Patent Application 62/094,848, filed Dec. 19, 2014; and U.S. Patent Application 62/094,856, filed Dec. 19, 2014, the entire contents of which are hereby incorporated by reference in their entireties for all purposes.

BACKGROUND

Ebola is a highly contagious disease that causes the death of the majority of patients suffering from the disease. (The term "Ebola" is used to refer generally to all species and strains of hemorrhagic fever-inducing Ebola virus, including Zaire, Sudan, Tai Forest, Bundibugyo, and Reston.) The initial symptoms are similar to those of many viral disorders, most of which other viral disorders do not require quarantine. An outbreak of Ebola in West Africa in 2014 highlighted the importance of early diagnosis of Ebola victims in order to begin treatment of those victims, and in order to quickly isolate them so as to prevent the further spread of the disease. However, present methods of detection and diagnosis of Ebola are time-consuming, expensive, complicated, and typically require laboratory equipment not often available in rural areas.

SEQUENCE LISTING

The instant application contains a Sequence Listing which has been submitted electronically in ASCII format and is hereby incorporated by reference in its entirety. Said ASCII copy, created on Oct. 7, 2015, is named 3042.601_SL.txt and is 51,058 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Applicant provides assays, devices, kits, methods, and systems for identifying Ebola virus and for identifying blood markers that are indicative or characteristic of Ebola infection. These assays and assay methods provide rapid results from small volume samples, such as small volume blood samples. These assays, devices, kits, methods, and systems are effective when applied to small volume blood samples, such as fingerstick blood samples, including but not limited to samples as small as 250 µL or less. These assays and assay methods are rapid, and provide results within a short time, e.g., in three hours of less, within two hours or less, or within one hour or less from the time sample analysis begins. In embodiments, these assays and assay methods provide results within a short time, e.g., in three hours of less, or within two hours or less, from the time a sample was obtained from a subject. In some embodiments, these assays, devices, kits, methods, and systems include nucleic acid assays for detection of Ebola Zaire virus (detected in the West Africa outbreak in 2014) in EDTA-anti-coagulated whole blood. These assays, devices, kits, methods, and systems may be used and performed at point of service locations, including in rural locations or locations remote from a hospital, clinic, or laboratory, as well as within a clinical laboratory or hospital.

Applicant provides assays, devices, kits, methods, and systems which may be performed entirely within a region of active infection (a "hot zone"), such as a region where subjects suffering from Ebola infections are present. Samples obtained from subjects suspected of suffering an Ebola infection may be obtained and analyzed within the hot zone using automatic sample analysis devices and systems (e.g., a sample processing unit ("SPU")), so that no samples need leave the hot zone, thereby reducing possible further spread of the disease. Advantageous automatic sample processing devices or systems (for example, an SPU) contain samples entirely within the devices or systems during analysis following loading the sample on or in the devices or systems; containing samples within the system reduces or prevents spread of contamination and may reduce or prevent the spread of disease that might otherwise occur due to actions or events incident to sample analysis. An automatic sample processing device or system (e.g., an SPU) may be enclosed in a container, or wrapped in a sheath, in order to reduce or prevent contamination of that device or system. Such a container or sheath may prevent spread of infectious material or agents from one location to another if the device or system is moved from one location to another location.

Applicant provides assays, devices, kits, methods, and systems which utilize nucleic acid assays along with assays for antibodies to the Ebola virus. In embodiments, Applicant provides assays, devices, kits, methods, and systems which utilize i) nucleic acid assays, ii) assays for antibodies to the Ebola virus, and iii) electrolyte assays. In embodiments, nucleic acid assays may comprise isothermal nucleic acid assays. In embodiments, isothermal nucleic acid assays include isothermal nucleic acid assays as described in U.S. patent application Ser. No. 14/214,850, filed Mar. 15, 2014; in international patent application PCT/US2014/030034, filed Mar. 15, 2014; and in international patent application PCT/US2014/056151, filed Sep. 17, 2014; these methods are collectively termed "TNAA" methods. In embodiments, assays for antibodies to the Ebola virus comprise IgM and IgG assays for antibodies to the Ebola virus. In embodiments, electrolyte assays comprise sodium assays, or potassium assays, or sodium and potassium assays. Thus, in embodiments, Applicant provides assays, devices, kits, methods, and systems which utilize i) nucleic acid assays, ii) IgM and IgG assays for antibodies to the Ebola virus, and iii) Sodium and Potassium assays. In embodiments, Applicant provides assays, devices, kits, methods, and systems which utilize i) TNAA nucleic acid assays, ii) IgM and IgG assays for antibodies to the Ebola virus, and iii) Sodium and Potassium assays. Such assays are typically performed on blood samples (e.g., fingerstick blood samples) obtained from subjects suspected of suffering from Ebola; however, in embodiments, such assays may be performed on urine or other bodily fluid samples obtained from a subject.

These assays, devices, kits, methods, and systems are suitable for evaluating patients with signs and symptoms of Ebola infection and for electrolyte balance management; evaluation of electrolytes allows caregivers to quickly assess patients for dehydration, and is believed to help protect caregivers from unnecessary Ebola exposure risk by expediting the assessment of whether oral or intravenous hydration is appropriate (e.g., avoidance of intravenous hydration where possible is believed to reduce Ebola exposure risk to caregivers).

The assays, devices, kits, methods, and systems disclosed herein may be used with blood samples collected by capillary means, e.g., with samples obtained using single-use fully retractable lancets. Thus, unlike prior methods which require personnel trained in performing phlebotomy, the assays, devices, kits, methods, and systems do not require needles and do not require trained personnel. Furthermore, the systems, devices, and kits can be deployed and used in any area, including rural areas, where Ebola is present or spreading, effective to provide local and real-time assessment, treatment and quarantine in a "hot zone" where the need is greatest. In embodiments, the assays, devices, kits, methods, and systems disclosed herein facilitate real-time reporting and modeling of cases through real-time connectivity to self-learning epidemiological models and software systems; e.g., assays may be run in configurations that enable remote connectivity through electronic links (e.g., satellite link, cellular network, landline, or other communication link).

In embodiments, the assays, devices, kits, methods, and systems may be used in conjunction with further assays useful for triage of patients to identify those suffering from Ebola from those suffering from other diseases. Such other assays useful for such triage include assays for detecting or measuring other pathogens causing other fevers of unknown origin, molecular tests for multiple strains of Ebola virus, assays for hemoglobin, and iron tests for anemia. In embodiments, assays for fevers of unknown origin may include but are not limited to assays for Lassa fever, malaria, cholera, typhoid fever, Marburg, dengue I, II, III and IV, chikungunya, West Nile, and meningitis. Triage of patients is believed to enable the rapid separation of Ebola patients from other patients, and to reduce the risk of Ebola infection to such other patients. Anemia assays may be useful to aid in triaging of patients (e.g., to determine whether or not a subject suffers from hookworm or other conditions, and so are at risk of dying of anemia for that reason as well, e.g., before being able to get treated for Ebola infection itself).

Accordingly, in embodiments, Applicants disclose an assay for the detection of Ebola Zaire virus (detected in the West Africa outbreak in 2014) comprising a TNAA assay that is for the detection of Ebola Zaire virus in whole blood or plasma specimens (e.g., in EDTA-anti-coagulated specimens). In embodiments, such assays include assays for detecting anti-Ebola antibodies in heparin-anticoagulated plasma specimens or in EDTA-anti-coagulated whole blood specimens. In embodiments, such assays include assays for detecting and measuring electrolyte levels, such as sodium and potassium levels in heparin-anticoagulated plasma specimens. Thus, Applicant discloses simultaneous or contemporaneous performance of i) a TNAA assay for Ebola Zaire virus, ii) IgM and IgG assays for the qualitative detection of IgM and IgG antibodies for Ebola virus, and iii) the quantitative measurement of levels of sodium and potassium from whole blood or plasma specimens (e.g., EDTA-anti-coagulated, or heparin-anti-coagulated whole blood or plasma, which may be extracted from whole blood specimens). Optionally, some embodiments may include Antigen ELISA assay for detection of the virus. In one embodiment, the TNAA assay may be used to detect for the virus in a window of 3 to 10 days after the onset of fever in the subject.

In embodiments, one or more of such assays are performed within an automatic sample analysis device or system (termed herein "SPU"). In embodiments, heparin-anti-coagulated plasma is extracted from whole blood in an SPU. IN embodiments, samples provided herein may contain an anticoagulant, such as heparin or EDTA.

Applicant discloses devices, including automatic sample analysis devices (e.g., an SPU) for performing the assays disclosed herein.

Applicant discloses systems, the systems including cartridges and including automatic sample analysis devices (e.g., an SPU) for performing the assays disclosed herein, the cartridges being configured for use with the automatic sample analysis devices. A system as disclosed herein may include a communication device, or communication link, or other electronic connection configured to provide information (e.g., protocols) to the automatic sample analysis device, or configured to transmit data or other information from the automatic sample analysis device, or both. A cartridge may include reagents for use in processing or testing a sample, disposables for use in processing or testing a sample, or other materials. For example, a cartridge may include reagents for use in processing or testing a sample for the presence of viral nucleic acids (e.g., Ebola RNA); may include reagents for use in processing or testing a sample for the presence of viral amino acids (e.g., Ebola nucleoprotein, or other proteins and proteinaceous material indicative of Ebola infection); may include reagents for use in processing or testing a sample for the presence of antibodies to a virus (e.g., antibodies to Ebola virus antigens); may include reagents for use in processing or testing a sample for the presence of electrolytes (e.g., for detecting sodium or potassium level abnormalities in a subject's blood); and combinations thereof. A cartridge may include vessels, such as, e.g., reagent vessels, mixing vessels, waste vessels, or other vessels, for use in processing or testing a sample. A cartridge may include disposables for use in processing or testing a sample. A cartridge may include cuvettes, and may include other components, elements, and materials for use in processing or testing a sample. A cartridge may include at least one sample. Optionally, the cartridge includes at least one or more slots for the insertion of one or more containers that may contain one or more samples.

Applicant discloses kits, the kits including reagents for performing the assays disclosed herein. In embodiments, the kits may include cartridges configured for use with the automatic sample analysis devices for performing the assays disclosed herein. In embodiments, the kits may include sample collection devices for performing the assays disclosed herein. In embodiments, the kits containing reagents may include cartridges, and, in embodiments, the reagents may be carried on the cartridges. In embodiments, the reagents carried on cartridges may include reagents for assays for detecting nucleic acids (e.g., Ebola virus nucleic acids); for detecting proteins or proteinaceaous material (e.g., reagents for detecting antibodies to Ebola virus, for detecting Ebola virus antigens, or both); for detecting electrolytes (e.g., for detecting sodium, potassium, or other electrolytes); and combinations thereof. In embodiments, the kits may include sample containers configured for use with the cartridges, or with the automatic sample analysis devices, or both, for performing the assays disclosed herein.

Such assays may be applied to any subject or any blood sample; for example, such assays may be usefully applied to samples obtained from individuals in affected areas with signs and symptoms of Ebola virus infection or who are at risk for exposure or may have been exposed to the Ebola Zaire virus (detected in the West Africa outbreak in 2014) in conjunction with epidemiological risk factors. In embodiments, the assays, devices, kits, methods, and systems disclosed herein may be used in areas where subjects may be at risk of contracting Ebola, e.g., in areas where patients may present for diagnosis and treatment of Ebola infection.

The assays, devices, systems, methods, and kits disclosed herein provide many advantages and benefits. A chief benefit associated with the present Ebola Zaire TNAA assays, along with the Ebola antibody and electrolyte assays disclosed herein, is the ability to perform continued testing of human specimens for Ebola virus, even in rural and remote locations, and even outside of clinical, hospital, or laboratory environments. The testing of human specimens for Ebola virus as disclosed herein provide diagnostic, clinical, and public health benefits, in addition to providing better tools for further research. True positive results provide confirmatory support for the diagnosis of an Ebola virus infection. True positive results also support the decision to isolate patients in negative-pressure rooms, if available, and employ practical viral hemorrhagic fever isolation precautions. Also, establishing the Ebola virus as the true cause of the patient's symptoms prevents further workup for other possible causes and allows saving of other healthcare resources. True negative results benefit both physicians and patients by ruling out a diagnosis and allowing other possible illnesses to be pursued.

The assays additionally benefit public health. If people infected with the Ebola virus are immediately isolated from other people and appropriate precautions are taken, this can prevent others from getting sick. By having this test done, the chance of spreading the virus to others is reduced. Also, using the test can help healthcare providers learn more about the Ebola virus and stop its spread.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 1 depicts the pre-analytical (sample processing, performed by the sample processing devices and systems described herein (termed "SPU", and as controlled by laboratory automation systems, termed herein "LAS"), analytical (report generation, performed by the LAS), and post-analytical (report transmission, performed by the LAS) parts of the devices and systems disclosed herein, and of the pre-analytical, analytical, and post-analytical steps of the methods disclosed herein.

FIG. 5. This figure illustrates the specificity of the TNAA nucleic acid assays. The specificity of the TH-EZN reaction was tested by adding the listed pathogens to the sample in addition to the positive control synthetic templates. No false negative reactions were seen. Ebola Zaire virus RNA was used as a positive control. The non-template control is labeled "NTC". The y-axis shows the time of detection based on the fluorescent signal recorded in real-time during the TNAA amplification reaction. The cutoff for assessing a positive reaction was 45.6 minutes.

FIG. 6. The effect of interfering substances was tested for the TH-EZN reaction in two ways. First interfering substances were added to the sample in addition to the positive control synthetic templates to see if the substances interfered with the reaction ("Inhibits True Positive"). Second, interfering substances were added to a sample without any template (NTC) to assess if a non-specific reaction occurred ("Causes False Positive"). Each substance was tested at two levels.

Figures 7A, 7B:
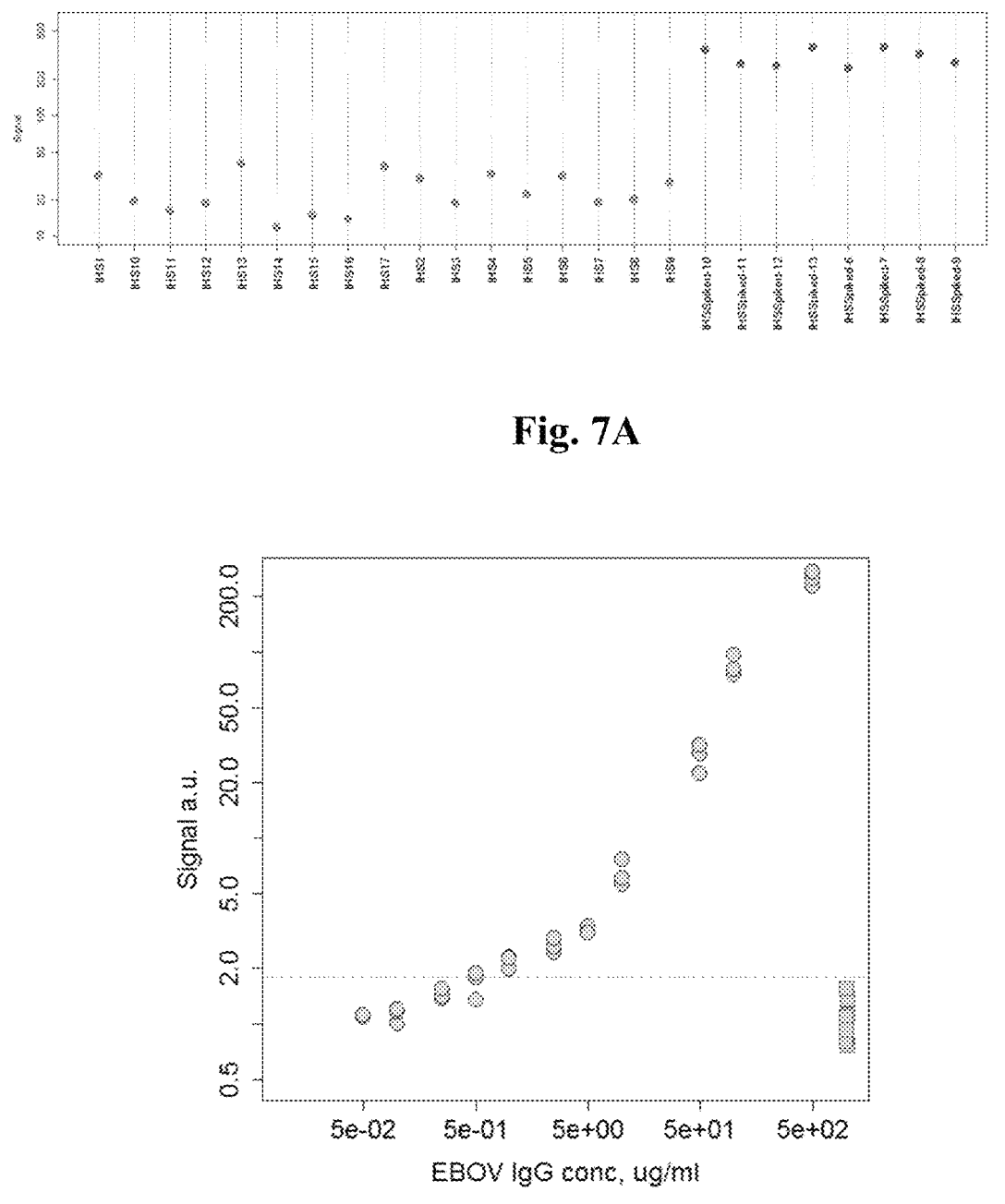

FIG. 7A shows results of assays using anti-Ebola IgG antibodies that were tested on spiked plasma samples. The data shown in FIG. 7A demonstrates the performance of the Ebola IgG Assays. FIG. 7A provides results comparing in-house (negative) EDTA-anticoagulated plasma samples with spiked samples. All samples were spiked with human anti-ZEBOV IgG to a nominal concentration of 1 µg/ml, FIG. 7B compares assay results from negative and spiked samples; the figure shows signals from assays run with in-house (negative) EDTA-anticoagulated plasma samples (squares) and spiked samples. All samples were spiked with human anti-ZEBOV IgG.

FIG. 7C provides a Table that summarizes cross reactivity data from Ebola IgG Assays.

Figures 8B, 9A:
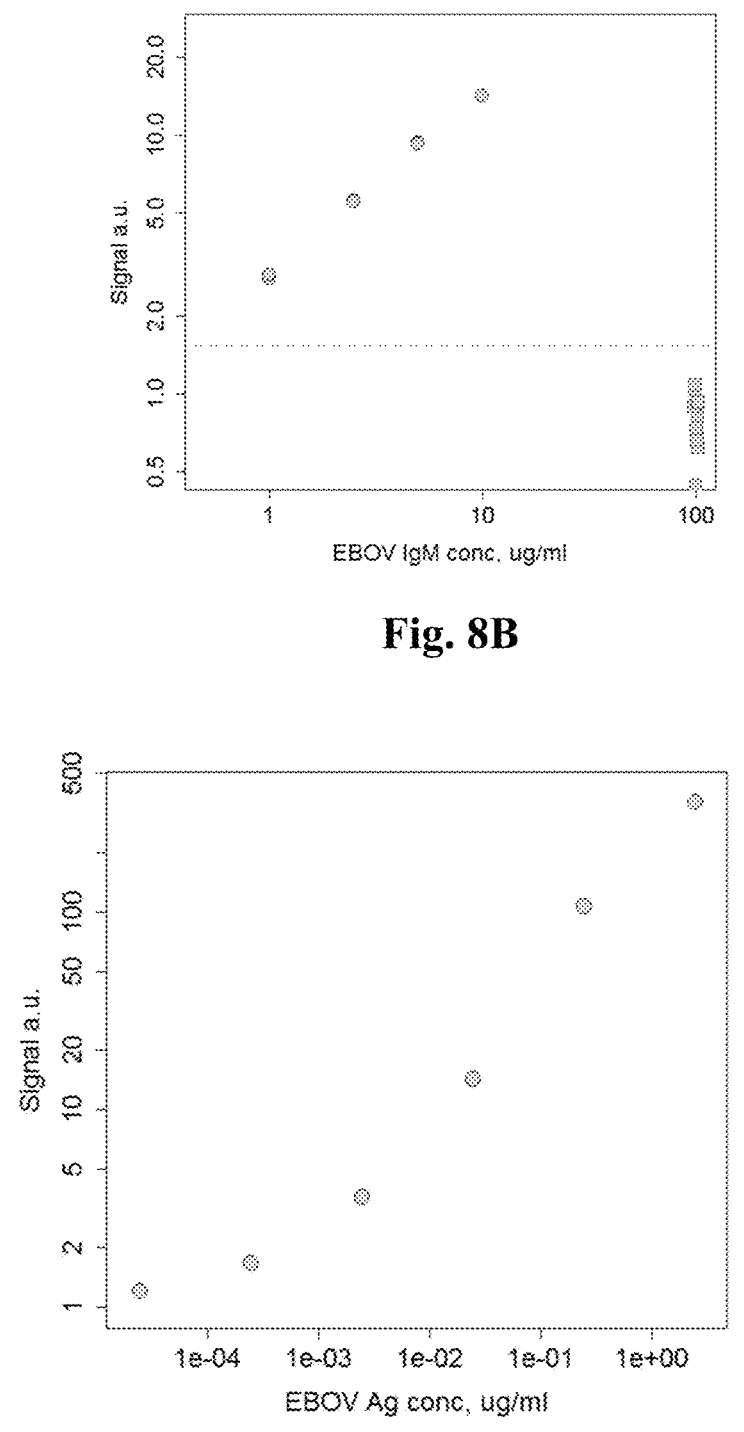

FIG. 8A shows results of assays using anti-Ebola antibodies were tested on spiked plasma samples. FIG. 8A provides results comparing in-house (negative) EDTA-anticoagulated plasma samples with spiked weak positive samples. All samples were spiked with human anti-ZEBOV IgM to a nominal concentration of 0.3 µg/ml.

FIG. 8B compares assay results from negative and spiked samples; the figure shows signals from assays run with in-house (negative) EDTA-anticoagulated plasma samples (squares) and spiked samples. All samples were spiked with human anti-ZEBOV IgM.

FIG. 9A shows dose-response results from assays with recombinant ZEBOV GP antigen spiked pooled normal serum calibrators.

FIG. 9B provides a Table that summarizes cross reactivity data from ZEBOV GP antigen ELISA Assays.

DETAILED DESCRIPTION

Figure 1:
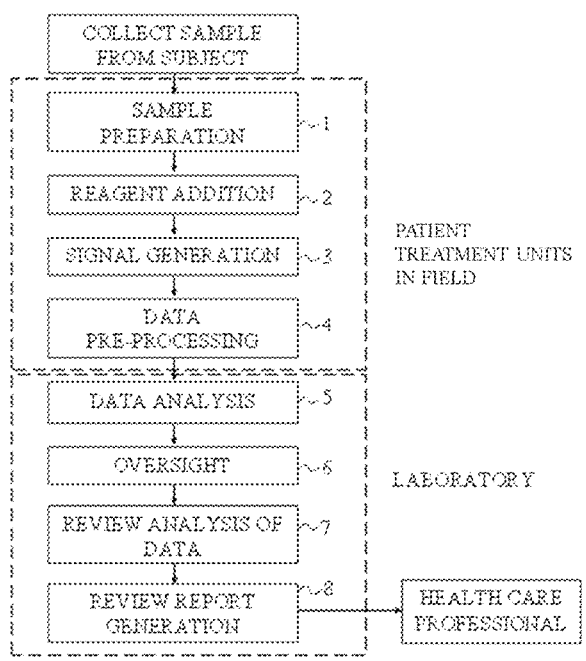
FIG. 1 provides a schematic outline of systems for detecting Ebola virus and related markers of Ebola as described herein.

Description and disclosure of examples of reagents, assays, methods, kits, devices, and systems which may use, or be used with, assays, devices, systems, kits, and methods disclosed herein may be found, for example, in U.S. Pat. Nos. 8,088,593; 8,380,541; 8,435,738; 8,475,739; 8,840,838; U.S. patent application Ser. No. 13/769,820, filed Feb. 18, 2013; U.S. patent application Ser. No. 14/183,503, filed Feb. 18, 2014; U.S. patent application Ser. No. 14/214,850, filed Mar. 15, 2014; International Patent Application PCT/US2014/030034, filed Mar. 15, 2014; International Patent Application PCT/US2014/056151, filed Sep. 17, 2014; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. patent application Ser. No. 13/244,946, filed Sep. 26, 2011; U.S. patent application Ser. No. 13/244,949, filed Sep. 26, 2011; and U.S. application Ser. No. 13/945,202, filed Jul. 18, 2013, the disclosures of which patents and patent applications are all hereby incorporated by reference in their entireties.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

Acronyms used herein typically have their customary meanings. Some acronyms as used herein include: ribonucleic acid (RNA); dexoyribonucleic acid (DNA); limits of detection (LOD); Sample Processing Unit (SPU); Laboratory Automation System (LAS); Clinical Laboratory Improvements Amendments (CLIA); polymerase chain reaction (PCR); reverse transcriptase PCR (RT-PCR); quantitative RT-PCR (Q-RT-PCR); personal protective equipment (PPE); real-time diagnostic (RDT); alkaline phosphatase (ALP); ethylene diamine tetra acetic acid (EDTA); Ebola Virus, Zaire strain (ZEBOV); Tetraphenylborate (TPB); Sodium Tetraphenylborate (NaTPB); Nucleic acid assay (NAA); isothermal nucleic acid assay (TNAA, or TNAA assay, or TNAA nucleic acid assay); Ebola virus Glycoprotein (GP); Ebola Zaire virus nucleoprotein (TH-EZN); Ebola Zaire virus glycoprotein (TH-EZG); RNA Spike-in Control (TH-RNA-SIC) assay; and Human Centromeric Repeat (TH-HCR) assay.

In this specification and in the claims which follow, reference may be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

The term "nucleic acid" refers to nucleotides and nucleosides which make up, for example, deoxyribonucleic acid (DNA) macromolecules and ribonucleic acid (RNA) macromolecules. Nucleic acids may be identified by the base attached to the sugar (e.g., deoxyribose or ribose); as used herein, the following abbreviations for these bases are used to represent nucleic acids in sequence listings identifying and describing their structures (either upper-case or lower-case may be used).

TABLE 1A

| Base (in Nucleic Acid) | Letter Code |
| --- | --- |
| Adenine | A |
| Thymine | T |
| Guanine | G |
| Cytosine | C |
| Uracil | U |

The terms "peptide", "polypeptide", "proteinaceous material", and "protein" may be used interchangeably to refer to molecules comprised of amino acids linked by peptide bonds. Individual amino acids may be termed "residues" of a polypeptide or protein. The amino acid sequences of polypeptides disclosed herein may be identified by SEQ ID NO: presented as a string of letters, where the letters have the following meanings:

TABLE 1B

| Amino Acid | 3-Letter Code | 1-Letter Code |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, a "sample" may be but is not limited to a blood sample, or a portion of a blood sample, may be of any suitable size or volume, and is preferably of small size or volume. A sample may be, for example, a blood sample (e.g., a sample obtained from a fingerstick, or from venipuncture, or an arterial blood sample), a urine sample, a biopsy sample, a tissue slice, stool sample, or other clinical sample; a water sample, a soil sample, a food sample, an air sample; or other sample. A blood sample may comprise, e.g., whole blood, plasma, or serum. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, a "fingerstick" or a "fingerstick sample" is a blood sample obtained by a small puncture in the skin, typically, although not necessarily, on a finger (e.g., such a puncture may be made on any skin surface, including a toe, a heel, an arm, a leg, or other body portion). A puncture for a fingerstick may be made, e.g., by a lancet, a needle, a sharp probe, or any other suitable instrument or implement.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Nucleic Acid Amplification Methods

The TNAA nucleic acid amplification method includes an isothermal method that provides rapid qualitative detection and identification of pathogens from clinical samples. In embodiments, a pre-amplification step may be included before the isothermal amplification; such a pre-amplification step may increase the overall sensitivity of the overall TNAA method.

For example, in order to further enhance the sensitivity of the TNAA assay, a pre-amplification step may be performed via RT-PCR on an SPU. PCR primers are designed to amplify the target gene for the subsequent isothermal amplification reactions used for specific detection. The RT-PCR reaction is conducted by thermal cycling, and the final product of this reaction is used for the subsequent isothermal amplification and specific detection conducted subsequently. Thus, in embodiments utilizing thermal cycling nucleic acid pre-amplification and isothermal nucleic acid amplification, steps may include, for example, pre-amplification by RT-PCR of an extracted RNA sample, resulting in greatly increasing copy numbers in the original extracted sample. The resulting pre-amplified product forms the starting sample for the TNAA reaction. Subsequent processing of the pre-amplified product by TNAA (i.e., without further thermal cycling) provides further amplification, and provides detection, of the target molecules.

Methods for nucleic acid amplification which do not require thermal cycling are described in U.S. Patent Application 61/800,606, filed Mar. 15, 2013, incorporated by reference herein in its entirety. Such methods may be used to detect nucleic acid markers of disease, such as respiratory disease, in small-volume samples in short periods of time. Such methods are discussed below, and examples of results obtained with such methods, from small samples and in short periods of time, are presented in the Figures and Examples disclosed herein. In the following, such methods are termed "non-cycling amplification methods."

Non-cycling amplification methods of nucleic acid amplification may be applied to double-stranded DNA. However, target nucleic acid molecules need not be limited to double-stranded DNA targets; for example, double-stranded DNA for use in non-cycling amplification methods described herein may be prepared from viral RNA, or mRNA, or other single stranded RNA target sources, by reverse transcriptase. In further example, double-stranded DNA for use in non-cycling amplification methods described herein may be prepared from single-stranded DNA targets by DNA polymerase. Such methods may be applied as an initial step, prior to application of the non-cycling amplification methods discussed below.

Amplification of a double-stranded DNA target, for example, begins with a primary double-stranded DNA to be amplified (termed the "primary nucleic acid" in the following). The primary nucleic acid contains a target region termed a template region; the template region has a template sequence. Such a double-stranded template region contains a first DNA strand and a complementary second DNA strand, and includes a 5' terminal nucleotide in one strand and a 3' terminal nucleotide in the other strand that are complementary to each other.

A first primer and a second primer are provided which each have template-binding regions and tail regions; the primer template-binding regions are complementary to the target template regions. The tail regions of the primers may contain three components: a) the 5' terminal nucleotide of the primer, b) an innermost nucleotide, wherein the innermost nucleotide is downstream from the 5' terminal nucleotide, and c) a middle section between the 5' terminal nucleotide and the innermost nucleotide, comprising one or more nucleotides. In addition, at least portions of the two primer tail regions may be complementary to each other when properly aligned.

It should be noted that although the tail region of the second primer may contain a nucleotide sequence which is complementary to the nucleotide sequence of the tail region of the first primer, typically, products formed by the annealing of the first primer and second primer are not desirable or useful for methods or compositions provided herein. Accordingly, in some embodiments, steps may be taken to minimize the formation of first primer—second primer annealed products. Such steps may include, for example, not pre-incubating a first primer and a second primer under conditions where the primers may anneal for an extended period of time before initiating a method provided herein.

The primary nucleic acid may be treated with a polymerase and a first copy of the first primer under conditions such that the template-binding region of the first copy of the first primer anneals to the first strand of the nucleic acid template. Under these conditions, an extension product of the first copy of the first primer is formed. The polymerase, which may have strand displacement activity, may catalyze the formation of the extension product of the first copy of the first primer. The first copy of the first primer may be covalently linked to the synthesized extension product, such that the first copy of the first primer (which is complementary to the first strand of the nucleic acid template) becomes part of the molecule described herein as the "extension product of the first copy of the first primer." The template-binding region but not the tail region of the first copy of the first primer anneals to the first strand of the nucleic acid template. Examples of conditions suitable for polymerase-based nucleic acid synthesis are known in the art and are provided, for example, in *Molecular Cloning: A Laboratory Manual*, M. R. Green and J. Sambrook, Cold Spring Harbor Laboratory Press (2012), which is incorporated by reference herein in its entirety.

The extension product of the first copy of the first primer may be treated with a polymerase (which may have strand displacement activity) and with the second primer under conditions such that the template-binding region of the second primer anneals to the extension product of the first copy of the first primer. In this way, an extension product of the second primer may be formed. The polymerase may displace the first strand of the nucleic acid template from the extension product of the first copy of the first primer during the synthesis of the extension product of the second primer. The second primer may be covalently linked to the synthesized extension product, such that the second primer becomes part of the molecule described herein as the "extension product of the second primer." The extension product of the second primer is complementary to the extension product of the first copy of the first primer. The template-binding region but not the tail region of the second primer may anneal to the extension product of the first copy of the first primer when the second primer anneals to the extension product of the first copy of the first primer.

The extension product of the second primer may be treated with a polymerase (which may have strand displacement activity) and a second copy of the first primer so as to form an extension product of the second copy of the first primer. During the generation of the extension product of the second copy of the first primer, the second copy of the first primer may be covalently linked to the synthesized extension product, such that the second copy of the first primer becomes part of the molecule described herein as the "extension product of the second copy of the first primer." The extension product of the second copy of the first primer is complementary to the extension product of the second primer.

Generation of the extension product of the second copy of the first primer may result in the generation of a molecule comprising the extension product of the second copy of the first primer and the extension product of the second primer, which may be referred to herein as the "secondary nucleic acid." A secondary nucleic acid may comprise the 3' terminal region of the extension product of the second primer (and the complement thereof) and may comprise the 3' terminal region of the extension product of the second copy of the first primer (and the complement thereof). Secondary nucleic acid molecules include sequences of the template region adjacent to tail sequences. In embodiments, double-stranded nucleic acids are produced in which complementary template and tail region sequences line up. In practice, multiple copies (e.g., two or more) of the secondary nucleic acid are produced by any process whereby a nucleic acid having the general structure of the secondary nucleic acid may be generated, including by practice of non-cycling amplification methods discussed herein.

Thus, pairs of copies of the secondary nucleic acid may be provided. Further numbers of copies may then be generated, for example, by repetition of the foregoing steps and methods. For example, the full process as described above for generating a secondary nucleic acid from a primary nucleic acid may be repeated two times, in order to generate a two pairs of copies of the secondary nucleic acid; further repetitions may be performed to amplify the number of copies further, e.g., to exponentially amplify the number of copies (e.g., by powers of two).

In addition, since the secondary nucleic acid molecules include sequences of the template region adjacent to tail sequences, partially double-stranded nucleic acids may be produced in which tail region sequences hybridize and line up. Since these tail region sequences are attached to single-stranded template regions, a cross-over structure having two nucleic acid strands together held by the hybridized tail region sequences is produced. These cross-over structures may be extended by a polymerase to form extension products of both component strands. These extension products which may be referred to as "concatemer strands." Two concatemer strands may be annealed together, and may be collectively referred to as a concatemer; such concatemers may contain two or more copies of the nucleic acid template.

In some embodiments, even longer concatemers may be formed. For example, concatemers may anneal together; or two concatemer molecules may form a cross-over structure similar to those formed by the shorter molecules termed concatemer strands, as discussed above, followed by a larger concatemer molecule containing four copies of the nucleic acid template. In another example, a secondary nucleic acid and a concatemer may form a cross-over structure, followed by a larger concatemer molecule containing three copies of the nucleic acid template. In some embodiments, multiple different concatemers of multiple different lengths may be simultaneously generated.

Thus, concatemers generated according to such methods may be of any length of nucleotides. In some embodiments, concatemer molecules generated herein may be at least 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. Concatemers generated according to such methods may contain any number of copies of a nucleic acid template. In some embodiments, concatemer molecules generated herein may contain at least 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies of a nucleic acid template. Further examples are provided, and greater detail of these and other examples, is provided in U.S. Patent Application 61/800,606, filed Mar. 15, 2013.

Detection of Reactions

Progress of a method provided herein may be monitored in multiple different ways. In one embodiment, a reaction may be assayed for a nucleic acid amplification product (e.g. for the level of the product or the rate of its generation). In another embodiment, a reaction may be assayed for the activity of a polymerase along a nucleic acid template (e.g. for movement of a polymerase along a template strand). Thus, in some embodiments, events of a method provided herein may observed due to the accumulation of product from a method (which may be during or after completion of steps of the method), or due to detectable events occurring during the steps of a method.

The presence of amplified nucleic acids can be assayed, for example, by detection of reaction products (amplified nucleic acids or reaction by-products) or by detection of probes associated with the reaction progress.

In some embodiments, reaction products may be identified by staining the products with a dye. In some embodiments, a dye may have greater fluorescence when bound to a nucleic acid than when not bound to a nucleic acid. In some embodiments, a dye may intercalate with a double-stranded nucleic acid or it may bind to an external region of a nucleic acid. Nucleic acid dyes that may be used with methods and compositions provided herein include, for example, cyanine dyes, PicoGreen®, OliGreen®, RiboGreen®, SYBR® dyes, SYBR® Gold, SYBR® Green I, SYBR® Green II, ethidium bromide, dihydroethidium, BlueView™, TOTO® dyes, TO-PRO® dyes, POPO® dyes, YOYO® dyes, BOBO® dyes, JOJO® dyes, LOLO® dyes, SYTOX® dyes, SYTO® dyes, propidium iodide, hexidium iodide, methylene blue, DAPI, acridine orange, quinacrine, acridine dimers, 9-amino-6-chloro-2-methoxyacridine, bis-benzimide dyes, Hoechst dyes, 7-aminoactinomycin D, actinomycin D, hydroxystilbamidine, pyronin Y, Diamond™ dye, GelRed™, GelGreen™ and LDS 751.

In some embodiments, reaction products may be identified by analysis of turbidity of amplification reactions for example, where increased turbidity is correlated with formation of reaction products and reaction by-products (e.g. pyrophosphate complexed with magnesium).

In some embodiments, reaction products may be identified by separating a reaction performed according to a method herein by gel electrophoresis, followed by staining of the gel with a dye for nucleic acids. The dye may be any nucleic acid dye disclosed herein or otherwise known in the art.

In some embodiments, any method or composition known in the art for the detection of nucleic acids or processes associated with the generation of nucleic acids may be used with methods and compositions provided herein.

In some embodiments, a nucleic acid probe which contains a nucleotide sequence complementary to a portion of a nucleic acid template strand (or strand having a similar or identical sequence) and which contains one or both of a fluorescent reporter (fluorophore) and a quencher are included in a reaction provided herein.

In an example, a nucleic acid probe may contain a fluorescent reporter at its 5' or 3' terminus, and a quencher at the other terminus.

In another example, a nucleic acid probe may contain a fluorescent reporter at its 5' or 3' terminus, and it may be annealed to a nucleic acid primer containing a quencher. The nucleic acid primer containing a quencher may contain the quencher at a position in the primer such that when the nucleic acid probe is annealed to the primer, the fluorescent reporter is quenched.

In probes containing a fluorescent reporter and quencher pair, the fluorescent reporter and quencher may be selected so that the quencher can effectively quench the reporter. In some embodiments, a fluorescent reporter is paired with a quencher where the emission maximum of the fluorescent reporter is similar to the absorption maximum of the quencher. Fluorphores that may be used as the fluorescent reporter include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applies Science), Texas red, FAM, TET, HEX, JOE, TMR, and ROX. Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

In some embodiments, a method provided herein may be monitored in an apparatus containing a light source and an optical sensor. In some situations, the reaction may be positioned in the path of light from the light source, and light absorbed by the sample (e.g. in the case of a turbid reaction), scattered by the sample (e.g. in the case of a turbid reaction), or emitted by the sample (e.g. in the case of a reaction containing a fluorescent molecule) may be measured. In some embodiments, a method provided herein may be performed or monitored in a device or module therein as disclosed in U.S. patent application Ser. No. 13/769,779, filed Feb. 18, 2013, which is herein incorporated by reference in its entirety.

Systems and Devices

In embodiments, systems and devices provided herein may be deployed in airplanes or airports, in order to test travelers for one or more pathogens, symptoms, or conditions described herein. In embodiments, systems and devices provided herein may be deployed in rural locations or in locations which are relatively far from a traditional laboratory (e.g. at least 10, 20, 50, 100, 200, or 500 miles from a traditional laboratory). In embodiments, systems and devices provided herein may have one or both of audio and visual input and output. Systems and devices provided herein with one or both of audio and visual functionalities may permit, for example, a subject to participate in a telemedicine session with a healthcare professional located at a remote location from the subject through a system or device provided herein. In embodiments, a healthcare professional may be remotely provided to a subject through a system or device provided herein, wherein the healthcare professional is the same gender as the subject seeking the healthcare consultation. For example, a female subject may want to see a female doctor, but there may be no female doctor near the location of the female subject. Through a system or device provided herein having one or both of audio and visual input and output, the female subject can consult with a female doctor who is located remotely from the location of the female subject.

The assays and methods disclosed herein may be performed on a device, or on a system, for processing a sample. The assays and methods disclosed herein can be readily incorporated into and used in an automated assay device, and in an automated assay system. For example, systems as disclosed herein may include a communication assembly for transmitting or receiving a protocol based on the analyte to be detected (e.g., an Ebola virus, such as an Ebola Zaire virus, an anti-Ebola antibody, or an electrolyte) or based on other analytes to be detected by the device or system. In embodiments, an assay protocol may be changed based on optimal scheduling of a plurality of assays to be performed by a device, or may be changed based on results previously obtained from a sample from a subject, or based on results previously obtained from a different sample from the subject. In embodiments, a communication assembly may comprise a channel for communicating information from said device to a computer, said wherein said channel is selected from a computer network, a telephone network, a metal communication link, an optical communication link, and a wireless communication link. In embodiments, systems as disclosed herein may transmit signals to a central location, or to an end user, and may include a communication assembly for transmitting such signals. Systems as disclosed herein may be configured for updating a protocol as needed or on a regular basis.

Accordingly, Applicants disclose devices configured to measure an analyte such as an Ebola virus in a sample of blood according to a method disclosed herein. Devices configured to measure an analyte such as, e.g., an Ebola virus, an anti-Ebola antibody, or an electrolyte in a sample of blood according to a method disclosed herein may be configured to detect or measure amounts of an analyte such as, e.g., an Ebola virus, an anti-Ebola antibody, or an electrolyte from a sample of blood that comprises no more than about 1000 µL of blood, or no more than about 500 µL of blood, no more than about 250 µL of blood, or no more than about 150 µL of blood, or no more than about 100 µL of blood, or no more than about 50 µL of blood, or, in embodiments, wherein said sample of blood comprises no more than about 25 µL of blood, or wherein said sample of blood comprises no more than about 10 µL of blood, or wherein said sample of blood comprises less than about 10 µL of blood. Such devices may be configured to detect or measure an analyte such as, e.g., an Ebola virus, an anti-Ebola antibody, or an electrolyte in a sample of blood in less than about three hours, less than about two hours, or less than about one hour, or, in embodiments, in less than about 40 minutes, or in less than about 30 minutes.

Devices disclosed herein may be configured to perform an assay for the detection or measurement of an analyte such as, e.g., an Ebola virus, an anti-Ebola antibody, or an electrolyte, and also to perform an assay for the measurement of another analyte in the blood sample. Devices disclosed herein may be configured to perform an assay for the detection or measurement of an analyte such as, e.g., an Ebola virus, an anti-Ebola antibody, or an electrolyte, and also to perform an assay comprising the measurement of a morphological characteristic of a blood cell in the blood sample. Devices disclosed herein may be configured to perform an assay for the detection or measurement of an analyte, e.g., an Ebola virus, an anti-Ebola antibody, or an electrolyte and also to perform an assay comprising the measurement of another blood analyte, e.g., a vitamin, a hormone, a drug or metabolite of a drug, or other analyte. Such devices may be configured wherein the assays, or the order of performance of assays, that are performed by said device may be altered by communication with another device.

Applicants also disclose systems comprising a device as disclosed herein. In embodiments, the system comprises a device that is configured to perform an assay for the detection or measurement of an analyte, e.g., an Ebola virus, an anti-Ebola antibody, or an electrolyte, and also to perform an assay for the measurement of another analyte in the blood sample. In embodiments, the system comprises a device that is configured to perform an assay for the detection or measurement of an analyte, such as, e.g., an Ebola virus, an anti-Ebola antibody, or an electrolyte, and also to perform an assay for the measurement of a morphological characteristic of a blood cell in the blood sample. In embodiments of such a system, assays, or the order of performance of assays, that are performed by said device may be altered by communication with another device.

Methods and compositions disclosed herein provide rapid assays which require only small amounts of sample, such as only small amounts of blood. Device and systems disclosed herein are configured to perform such rapid assays which require only small amounts of sample, such as only small amounts of blood. Accordingly, the methods, compositions, devices, and systems provide rapid tests, which require only small biological samples, and thus provide advantages over other methods, compositions, assays, devices, and systems.

The assays and methods disclosed herein may be performed on a device, or on a system, for processing a sample. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be an automatic assay device. A device may be an automatic assay device. An automatic assay device may be configured to facilitate collection of a sample, prepare a sample for a clinical test, or effect a chemical reaction with one or more reagents or other chemical or physical processing, as disclosed herein. An automatic assay device may be configured to obtain data from a sample. An automatic assay device may be configured to transmit data obtained from a sample. An automatic assay device may be configured to analyze data from a sample. An automatic assay device may be configured to communicate with another device, or a laboratory, or an individual affiliated with a laboratory, to analyze data obtained from a sample.

An automatic assay device may be configured to be placed in or on a subject. An automatic assay device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. An automatic assay device may receive a sample from the subject through a housing of the device. The sample collection may occur at a sample collection site, or elsewhere. The sample may be provided to the device at a sample collection site.

In some embodiments, an automatic assay device may be configured to accept or hold a cartridge. In some embodiments, an automatic assay device may comprise a cartridge. The cartridge may be removable from the automatic assay device. In some embodiments, a sample may be provided to the cartridge of the automatic assay device. Alternatively, a sample may be provided to another portion of an automatic assay device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, an automatic assay device, one or more components of the cartridge may be brought into fluid communication with other components of the automatic assay device. For example, if a sample is collected at a cartridge, the sample may be transferred to other portions of the automatic assay device. Similarly, if one or more reagents are provided on a cartridge, the reagents may be transferred to other portions of the automatic assay device, or other components of the automatic assay device may be brought to the reagents. In some embodiments, the reagents or components of a cartridge may remain on-board the cartridge. In some embodiments, no fluidics are included that require tubing or that require maintenance (e.g., manual or automated maintenance).

In embodiments, a cartridge may include reagents for use in nucleic acid assays for processing or testing a sample by detecting or quantifying nucleic acid targets in the sample, and may also include disposables for use in processing or testing a sample, or other materials. In embodiments, a cartridge may include all reagents for use in nucleic acid assays for processing or testing a sample by detecting or quantifying nucleic acid targets in the sample, and may also include all disposables required for processing or testing a sample.

In embodiments, a cartridge may include reagents for use in amino acid assays (e.g. ELISAs) for processing or testing a sample by detecting or quantifying proteins, peptides, or other proteinaceous material in the sample, and may also include disposables for use in processing or testing a sample, or other materials. In embodiments, a cartridge may include reagents for use in general chemistry assays for processing or testing a sample by detecting or quantifying target material (e.g., vitamins, hormones, metabolites, and other molecules) in the sample In embodiments, a cartridge may include reagents for use in receptor-based assays for processing or testing a sample by detecting or quantifying target material in the sample that binds specifically to the receptors used in the receptor-based assays. In embodiments, a cartridge may include reagents for use in further assays for processing or testing a sample by detecting or quantifying electrolytes in the sample. In embodiments, a cartridge may include reagents for use in further assays for processing or testing a sample by detecting or quantifying cells in the sample by cytometry.

Accordingly, in embodiments, a cartridge may include all reagents necessary for performing a nucleic acid assay in an automatic sample analysis device or system; and, in embodiments, that cartridge may further carry a sample, may further carry pipettes, mixing vessels, cuvettes, waste containers, or other implements and tools useful for the performance of such nucleic acid assays. In embodiments, a cartridge may include all reagents necessary for performing an amino acid assay in an automatic sample analysis device or system; and, in embodiments, that cartridge may further carry a sample, may further carry pipettes, mixing vessels, cuvettes, waste containers, or other implements and tools useful for the performance of such amino acid assays. In embodiments, a cartridge may include all reagents necessary for performing a general chemistry assay in an automatic sample analysis device or system; and, in embodiments, that cartridge may further carry a sample, may further carry pipettes, mixing vessels, cuvettes, waste containers, or other implements and tools useful for the performance of such general chemistry acid assays. In embodiments, a cartridge may include all reagents necessary for performing an electrolyte assay in an automatic sample analysis device or system; and, in embodiments, that cartridge may further carry a sample, may further carry pipettes, mixing vessels, cuvettes, waste containers, or other implements and tools useful for the performance of such electrolyte assays. In embodiments, a cartridge may include all reagents necessary for performing a receptor-based assay in an automatic sample analysis device or system; and, in embodiments, that cartridge may further carry a sample, may further carry pipettes, mixing vessels, cuvettes, waste containers, or other implements and tools useful for the performance of such receptor-based assays. In embodiments, a cartridge may include all reagents necessary for performing a cytometric assay in an automatic sample analysis device or system; and, in embodiments, that cartridge may further carry a sample, may further carry pipettes, mixing vessels, cuvettes, waste containers, or other implements and tools useful for the performance of such cytometric assays. In embodiments, a cartridge may include reagents, tools, implements, or a sample, or combinations thereof, for any two or more of nucleic acid assays, amino acid assays, general chemistry assays, electrolyte assays, and receptor-based assays.

For example, a cartridge may include reagents for use in processing or testing a sample for the presence of viral nucleic acids (e.g., Ebola RNA); may include reagents for use in processing or testing a sample for the presence of viral amino acids (e.g., Ebola nucleoprotein, or other proteins and proteinaceaous material indicative of Ebola infection); may include reagents for use in processing or testing a sample for the presence of antibodies to a virus (e.g., antibodies to Ebola virus antigens); may include reagents for use in processing or testing a sample for the presence of electrolytes (e.g., for detecting sodium or potassium level abnormalities in a subject's blood); and combinations thereof. A cartridge may include vessels, such as, e.g., reagent vessels, mixing vessels, waste vessels, or other vessels, for use in processing or testing a sample. A cartridge may include disposables for use in processing or testing a sample. A cartridge may include cuvettes, and may include other components, elements, and materials for use in processing or testing a sample. A cartridge may include at least one sample. Optionally, the cartridge includes at least one or more slots for the insertion of one or more containers that may contain one or more samples.

In embodiments, a sample may be a blood sample, such as a small volume blood sample, e.g., a fingerstick blood sample. The blood sample may be whole blood; plasma; serum; heparin-treated whole blood; ethylene diamine tetra-acetic acid (EDTA)-treated whole-blood; centrifuged blood; filtered blood; or other form of blood sample.

A sample or reagent may be transferred to a device, such as an automatic assay device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the automatic assay device. The sample, reagent, or aliquot thereof can be deposited at a location on or within the automatic assay device. Sample and reagent, or multiple reagents, may be mixed using a sample handling system in a similar manner. One or more components of the cartridge may be transferred in an automated fashion to other portions of the automatic assay device, and vice versa.

A device, such as an automatic assay device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

An automatic assay device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. An automatic assay device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

An automatic assay device may be configured to run one or more assay on a sample, and to obtain data from the sample. An assay may include one or more physical or chemical treatments, and may include running one or more chemical or physical reactions. An automatic assay device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

An automatic assay device may be configured to perform a plurality of assays on a sample. In embodiments, an automatic assay device may be configured to perform a plurality of assays on a single sample. In embodiments, an automatic assay device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. An automatic assay device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

An automatic assay device may perform nucleic acid assays, including isothermal nucleic acid assays (e.g., assays for detecting and measuring nucleic acid targets in a sample, including DNA and RNA targets). In embodiments, an automatic assay device may perform nucleic acid assays as disclosed in U.S. patent application Ser. No. 14/183,503, filed Feb. 18, 2014; U.S. patent application Ser. No. 14/214,850, filed Mar. 15, 2014; International Patent Application PCT/US2014/030034, filed Mar. 15, 2014; and in International Patent Application PCT/US2014/056151, filed Sep. 17, 2014. An automatic assay device may perform antibody assays, including enzyme-linked immunosorbent assays (ELISA), and other assays for detecting and measuring the amounts of proteins (including antibodies), peptides, and small molecules in samples. An automatic assay device may perform general chemistry assays, including electrolyte assays (e.g., assays for detecting and measuring the amounts of electrolytes such as sodium and potassium in a sample).

An automatic assay device may be configured to detect one or more signals relating to the sample. An automatic assay device may be configured to identify one or more properties of the sample. For instance, the automatic assay device may be configured to detect the presence or concentration of one analyte or a plurality of analytes or a disease condition in the sample (e.g., in or through a bodily fluid, secretion, tissue, or other sample). Alternatively, the automatic assay device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, an automatic assay device may be configured to transmit data obtained from a sample. In embodiments, an automatic assay device may be configured to communicate over a network. An automatic assay device may include a communication module that may interface with the network. An automatic assay device may be connected to the network via a wired connection or wirelessly. The network may be a local area network (LAN) or a wide area network (WAN) such as the Internet. In some embodiments, the network may be a personal area network. The network may include the cloud. The automatic assay device may be connected to the network without requiring an intermediary device, or an intermediary device may be required to connect an automatic assay device to a network. An automatic assay device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

An automatic assay device may provide data regarding a sample to, e.g., a health care professional, a health care professional location, such as a laboratory, or an affiliate thereof. One or more of a laboratory, health care professional, or subject may have a network device able to receive or access data provided by the automatic assay device. An automatic assay device may be configured to provide data regarding a sample to a database. An automatic assay device may be configured to provide data regarding a sample to an electronic medical records system, to a laboratory information system, to a laboratory automation system, or other system or software. An automatic assay device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by an automatic assay device, or analysis of such data, or reports, may be provided to a database, an electronic medical records system, to a laboratory information system (LIS), to a laboratory automation system (LAS), or other system or software.

In one embodiment, nucleic acid amplification (NAA) is performed from a capillary blood sample. The nucleic acid amplification may be qualitative or quantitative. In one embodiment, the portion of the sample for NAA is processed to remove formed components and leave only plasma. Optionally, the portion of the sample for NAA is processed to remove formed components and leave only serum. Optionally, the portion of the sample for NAA comprises capillary blood that is processed with at least one pre-treatment such as but not limited to at least one anti-coagulant compatible with the NAA technique.

In one non-limiting example, the collection of the sample may be by way of a sample collection device such as but not limited to those described in PCT Patent Application Ser. No. PCT/US14/30792 filed Mar. 17, 2014 and PCT Patent Application Ser. No. PCT/US13/00268 filed Dec. 5, 2013, both fully incorporated herein by reference for all purposes.

In another non-limiting example, the process may involve shipping and/or collecting fingerstick samples of capillary blood and/or other biological sample for analysis, wherein such analysis may include but is not limited to nucleic acid amplification, electrolyte(s) measurement, and combined antibody measurement from the same original sample. Also, some embodiments may include complete blood count (CBC) and cell counting for infection triage and management, all on the same sample collected from the subject at one collection.

In one non-limiting example, the process may involve use of a phenol based inactivation material on the sample to inactivate a virus, such as the Ebola virus (e.g., Ebola Zaire virus), wherein such inactivation material may be but is not limited to Trizol (Invitrogen) (comprising by weight: 30-60% Phenol, 15-40% Guanidine isothiocyanate, and 7-13% Ammonium thiocyanate) or other inactivation agent in sample collection vial(s), sample collection circuit, or the like to fully deactivate sample for transport or prior to instrument use. Optionally, some embodiments may use RNeasy (Qiagen) and/or Tripure (Roche) reagent(s). In one non-limiting example, sample inactivation is accomplished through use of a one-step sample homogenization/lysis procedure, in which the TriPure isolation reagent disrupts cells and denatures endogenous nucleases, wherein chloroform may also be added along with or after the TriPure reagent. Other optional virus inactivation techniques may include use of: bleach such as but not limited to 1:10 Bleach solution, 5% Lysol/phenolics, micro-chem/quaternary ammonium, incineration/autoclave, and or virus labile to desiccation and UV. Some of these inactivation techniques may be applied to sample after the sample has been processed for analyte levels. Optionally, some may be applied to certain portion(s) of the sample, such as a pellet of formed blood components, that will not be analyzed. Some embodiments may have an SPU with inactivation to be conducted in the device, wherein the user loads a sample container with active sample into a cartridge and inserts the cartridge into the SPU. In such an embodiment, the SPU will automatically handle inactivation to all or parts of the sample at time(s) as determined by programmable protocol being executed by the SPU. Some embodiments may include inactivation material in the cartridge C. Optionally, some embodiment may contain inactivation material in a reservoir that is onboard the SPU and not part of the cartridge C. Optionally, some embodiments may allow for insertion of two cartridges into the SPU, which in one non-limiting example, one cartridge has reagents and one cartridge has inactivation material(s).

Alternatively, the process may inactivate the sample through lysis and extraction steps in device (or both). Optionally, some embodiments may use an activated sample so long as a cap or cover is added prior to vigorous motion. Optionally, still further embodiments may centrifuge the collection vial prior to insertion into the device, or optionally, centrifuge inside the device. Optionally, other formed component separation techniques may be used on the sample prior to insertion into the device, or optionally, inside the device. Optionally, some embodiments may use a further containment enclosure around the device to minimize the risk of contamination outside of the device.

An automatic sample analysis device may have a housing; such a housing may act as a containment enclosure. In embodiments, an automatic sample analysis device may be placed within an enclosure, such as a containment enclosure. An automatic sample analysis device placed within an enclosure may have a housing, and in such an embodiment the housing thus will be enclosed within the enclosure.

A housing may include one or more air filters, such as, e.g., high efficiency particulate air (HEPA) filters suitable for blocking the flow of contaminants and micro-organisms. A containment enclosure may include one or more air filters, such as, e.g., HEPA filters suitable for blocking the flow of contaminants and micro-organisms. In embodiments, air filters may filter outside air as it flows to, or as it enters, or both, the interior of the containment enclosure, effective to reduce or prevent the entry of dust or other contamination into the SPU, to reduce or prevent interference with the operation of the SPU, and to reduce or prevent damage to the SPU. In embodiments, air filters may filter air as it flows outwardly, or as it leaves, or both, the interior of the containment enclosure, effective to reduce or prevent contamination (whether droplets, particulate matter, or other contaminants) from exiting the SPU, effective to reduce or prevent transport or spread of hazardous material out of the SPU. In embodiments, an air filter suitable for use in a containment enclosure is capable of filtering out the vast majority of particles (i.e., preventing the passage of the particles through the filter) in air entering the filter. For example, a suitable air filter may filter out greater than about 98% of the 0.3 micron (0.3 µm) diameter particles in air entering the filter. In embodiments, a suitable air filter may filter out greater than about 99% of the 0.3 µm diameter particles in air entering the filter; or greater than about 99.5%, or greater than about 99.7%, or greater than about 99.8%, or greater than about 99.9%, or greater than about 99.95%, or greater than about 99.995%, or greater than about 99.9995%, or greater than about 99.99995%, or greater than about 99.999995%, or greater, of the 0.3 µm diameter particles in air entering the filter.

In one non-limiting example, sensitive (low limit of detection [LoD]) NAA is performed on capillary samples from dilutions or pre-amplification thermal cycling to increase sensitivity (especially on an isothermal assay). Additionally, some embodiments may use an isothermal assay from capillary samples to generate real-time data (<1 hour and often <30 minutes on positive patients) for real-time triage and to be able to effect quarantine on subject(s) that test positive.

Optionally, some embodiments may use a sample collection device with formed component separation capability for obtaining plasma or otherwise separating out cells, such as but not limited to a sample collection device described in PCT Patent Application Ser. No. PCT/US14/30070 filed Mar. 15, 2014 and fully incorporated herein by reference for all purposes. Optionally, the system may provide any combination of tests run from a fingerstick sample shipped as whole blood or shipped and separated into plasma immediately after collection through a collection circuit.

Embodiments of the system may provide the ability to put the system into hot zones themselves as opposed to reference labs to facilitate quarantine on the spot without wait times for tests to be couriered off, and the therefore facilitate containment, wherein active samples are not being transported outside the hot zone.

Also, some embodiments may use customized trucks with sample processing devices on them with optionally, one or more of the following: power built in/generators, refrigerators, connectivity including satellite connectivity, and/or security for driving/locating in disaster zones. These trucks or similar vehicles can distribute and create decentralized locations around which to do real-time quarantine for containment. Optionally, some embodiment may use trucks or mobile units for Ebola detection that is decentralized to distributed locations with built in power and satellite connectivity for real-time triage and quarantine, with containment housing structures with beds built around them.

In embodiments, an SPU may be a modular device used for performing pre-analytic functions (e.g., one or more of sample dilution, sample aliquotting, sample preparation, and other functions) as described herein. An SPU may be designed to automatically replicate the processing systems used in the relevant traditional, manual or partially manual, assay protocols. In embodiments, an SPU may be enclosed in a thermally insulated and light-tight sheet metal enclosure. In embodiments, an SPU may have some, and in embodiments, may have all, of the following components: Liquid Handling Module, Centrifuge Module, Sonicator Module, Magnet Tool, one or more detectors (which may include a Luminometer Module, a Fluorometer Module, a Fluorometer/Turbidimeter Module, a Spectrophotometer Module, and a Microscopy Module; in embodiments, an SPU will include all such detectors), a Thermal Control System, and a Machine Vision System. In embodiments, an SPU may be made from any suitable components, including purchased components, machined parts, and molded parts. In embodiments, such machined parts may be made of aluminum, stainless steel, or other metals.

A sample, consumables, reagents, reagent vessels, and other items may be provided to a SPU via a cartridge. For example, the sample and products of further processing and reaction may be contained in disposable consumables inside the disposable reagent tray or Cartridge. All consumables are discrete such that reagents and reactions for each assay reside and occur, respectively, in physically separate locations to prevent cross-reactivity. The consumables contain all liquids or reagents such that no sample or reagent ever directly interacts with an SPU. All consumables for processing are contained in the Cartridge (and are not built into the SPU) and may be placed back into the Cartridge at the completion of processing for disposal.

Consumables which may be used for the NAA assays include, without limitation, the following: Round vessels (e.g., 60 µL capacity polypropylene vessels for storing reagents, dilutions, mixing, and reactions); Wash vessels (e.g., 200 µL capacity polypropylene vessels for storing wash buffers); Centrifuge vessels (e.g., in one embodiment, a narrow diameter 100 µL capacity polystyrene vessels for centrifuging blood and efficiently removing supernatant; or, in another embodiment, a 120 µL capacity polypropylene vessels for centrifuging samples and efficiently mixing and transferring small volumes); Mini tips (e.g., 10 µL capacity polypropylene tips for transporting fluids; may include silica filters for preventing cross-contamination); Large tips (e.g., 40 µL capacity polypropylene tips for transporting fluids; with silica filters for preventing cross-contamination); Dynamic Dilution tips (e.g., 10 µL capacity coated polystyrene tips for transporting solutions; with silica filters for preventing cross-contamination); NAA vessels (e.g., 60 µL capacity polypropylene vessels which serve as reaction vessels for the amplification reaction). In embodiments, a final fluorescence signal from the product generated in these vessels may be detected from NAA vessels.

Further consumables may include, for example, NAA trays (e.g., trays which hold multiple NAA vessels, such as 8 NAA vessels); such trays may be designed so as to be able to be picked up by the fluid handling module to transport the vessels between the Cartridge and the NAA module of a SPU. Further consumables may include, for example, a sonicator vessel (e.g., a 350 µL polystyrene vessel which may be used to contain sample during sonication). Further consumables may include, for example, a Magnet Tool Sleeve (e.g., a disposable polypropylene sleeve used to separate a magnet from a consumable, or sample, or other material or object, to prevent contamination).

A cartridge may house some or all of the consumables listed above. A cartridge may house a sample and some or all of the consumables listed above. A cartridge may include a lid to hold all consumables in place and prevent user interaction. In embodiments, a cartridge may be provided with a closed lid, under which all consumables required for NAA assays may be carried as required. Reagents and buffers required for performance of NAA assays may be pre-filled and sealed in vessels (e.g., in Round vessels and Wash vessels). Similarly, consumables and reagents for another type of assay, such as cytometry, ELISA, general chemistry, or other assay, may be provided in a Cartridge. Similarly, consumables and reagents for other types of assays, such as cytometry, ELISA, general chemistry, and other assays, may be included with those for NAA or with those for other assays in the same Cartridge. Thus, in embodiments, consumables and reagents for other types of assays, such as cytometry and other general chemistry assays, may be included with a Cartridge dedicated to a single type of assay, or dedicated to two types of assays (e.g., two of NAA, Cytometry, ELISA, and general chemistry). In embodiments, consumables and reagents for other types of assays, such as cytometry and other general chemistry assays, may be included with a Cartridge dedicated to three types of assays (e.g., three of NAA, Cytometry, ELISA, and general chemistry), or may include consumables for all of these types of assays. The NAA vessels may be provided pre-filled with the master mix for the assay, and may include by a protective wax layer on top of the NAA vessels to contain the master mix.

In embodiments, a Laboratory Automation System (LAS) may include at least one server configured to communicate with and control one or more SPUs. For example, communication with and control of one or more SPUs may be accomplished using an encrypted, certificate-based security system. An LAS may provide a number of functions, including communicating test protocols to the SPU based on the desired tests to be run on the sample and for maintaining oversight over the SPUs. During processing, the SPU and LAS may communicate to validate the quality and integrity of the consumables, based on lot information tracked in the LAS, execute the sample processing steps, and monitor and oversee the quality of the sample processing, and perform other functions and operations. After controlling sample processing in the SPU, signal sets from the sample may be transferred to the LAS where the raw data may be analyzed, the relevant reportables generated for a Laboratory Information System, and post-analytic processing steps performed.

In embodiments, an LAS may be overseen by a Clinical Laboratory Improvements Act (CLIA)-certified laboratory; such oversight may provide oversight and remote control of the SPU. For example, consumables containing patient samples (e.g., a Theranos Nanotainer™ tube for blood sample) may be placed in a Cartridge and may be inserted into the SPU. The SPU may scan a barcode on the Cartridge, and the barcode value may be communicated to the LAS. The LAS may securely de-code the barcode value, and may communicates a sample processing protocol to the processor in the SPU. A processor may further distribute tasks received from the LAS to various modules in the SPU. The SPU may feed information back to the LAS for monitoring of the SPU and its performance. In embodiments, the SPU may constantly feed information back to the LAS to ensure constant monitoring of the SPU and of its performance. In embodiments, final steps of sample processing may include signal generation (such as, e.g., fluorescence light for NAA assays, chemiluminescence light for ELISA assays, and transmitted light intensity spectrum for electrolyte assays), and signal detection by detectors. Such data may be transmitted to the LAS, which may perform analysis on these raw data and yield clinically relevant analyte reportables. In embodiments, such analysis performed on these raw data, and such clinically relevant analyte reportables yielded by such analysis, may be provided to, and may be useful for, CLIA laboratory staff to oversee and further analyze, as applicable.

In embodiments, as SPU may operate under the control of an LAS. For example, an SPU may be connected to the LAS via a secure Internet or other data network connection, e.g., via Iridium satellite technology and service. An SPU and an LAS may be connected via two-way communication with each other. For example, an LAS can send various commands and protocols to the processor of an SPU, for execution by the SPU. Similarly, an SPU can send information obtained by the SPU to an LAS, such as data obtained from pre-analytic steps with a sample or information obtained from sensors within an SPU (e.g. signal, image, temperature information). Information sent by an SPU to an LAS may be in response to a specific request for information from the LAS to the SPU, or it may be part of a standardized protocol. For example, upon completion of pre-analytic processing in the SPU, an LAS may perform analysis and post-analytic processing.

Although a SPU may be situated at a Field Site location which may be physically separate from an LAS, in embodiments complete control and oversight may be extended from the central LAS to the remote SPU to ensure CLIA-oversight and certification of the tests being reported. The SPU may serve as part of a CLIA-certified laboratory, and laboratory results generated from data analyzed in the LAS and obtained from a sample processed on a SPU may be CLIA-certified.

In embodiments, a touch screen may be provided in or on an SPU for operation of the device. Such a touchscreen may allow for detailed, user-oriented instructions, oversight, e.g., by ensuring a technician follows all appropriate steps before processing a sample, and two way communications. In embodiments, operation of an SPU at a remote location may be performed by a phlebotomist or other appropriately authorized technician trained in the operation of an SPU, e.g., trained in the operation of an SPU at a Field Site location.

In embodiments, an LAS may allow the operation of the clinical laboratory process without operator intervention. For example, such operation without operator intervention may include control of the SPU through one or more of direct LAS interfacing, specimen manipulation, transportation of the specimen and related signals, result evaluation, repeat testing, reflex testing and quality assessment and results reporting.

In embodiments, a secure communications infrastructure may be used to allow for CLIA-compliance for certified analysis and testing through the LAS for determination of the presence or absence of various substances in subjects (e.g., in a human subject) in a CLIA-certified laboratory while automating sample processing in field through the SPU in Field Sites to minimize pre-analytic error and variability.

Example 1

The samples analyzed in this example were analyzed by an automatic sample analysis device, the SPU. The methods illustrated in this example may be applied to other automatic sample analysis devices having capabilities as disclosed herein.

An automatic sample processing device or system, such as an SPU, may include fluid handling and fluid transport capabilities, including sample vessels, mixing vessels, and other containers for holding and processing samples; may include a centrifuge, vessels for use with a centrifuge, and other elements or components for use with a centrifuge; may include a sonicator, vessels for use with a sonicator, and other elements or components for use with a sonicator; may include magnets and magnetic components for use, e.g., in magnetic separation of components of a sample; may include an optical detector, an electronic detectors; may include a light source, a filter, a mirror, a prism, and other optical elements and components; and may include other components and capabilities.

A sample may be provided to (e.g., loaded in) an automatic sample processing device or system, such as an SPU, via a cartridge. A cartridge for use with an automatic sample processing device or system, such as an SPU, may include reagents for sample analysis, vessels for use in analyzing a sample, and other components, tools, devices, or consumables for use in analyzing a sample. Thus, a cartridge may carry a sample, and be used to provide a sample to an automatic sample processing device or system, such as an SPU. A cartridge may carry reagents and other materials for use in analyzing a sample. In embodiments, a cartridge may carry a sample and may carry reagents and other materials together with that sample, for use in analyzing that sample by an automatic sample processing device or system, such as an SPU.

In this example, small volume blood samples are tested for the presence of Ebola virus markers, and for electrolyte levels indicative of Ebola infection.

The Sample used for TNAA assay: ethylene diamine tetra acetic acid (EDTA)-anti-coagulated whole blood collected by fingerstick.

The Sample used for ELISA assay: heparin-anticoagulated plasma collected by a fingerstick as whole blood (processed in the SPU into plasma). EDTA-anti-coagulated whole blood may also be used for the ELISA assay.

The Sample used for Electrolyte assay: heparin-anticoagulated plasma collected by a fingerstick as whole blood (processed in the SPU into plasma).

What was measured: Specific nucleic acid sequences from the genome of the Ebola Zaire Virus, IgM and IgG antibodies to the Ebola virus, and sodium and potassium levels.

The final steps of sample processing are signal generation (which is fluorescence light for the TNAA assays, chemiluminescence light in the case of the ELISA assays, and transmitted light intensity spectrum for the Electrolyte assays).

For the first time, healthcare providers may be able to run a molecular assay for the rapid detection of the Ebola virus at the same time as assays for the antibodies to the Ebola virus along with essential chemistry assays for sodium and potassium assays to manage electrolyte imbalances in the field where patients are presenting with signs and symptoms of Ebola infection without requiring transport of samples to a clinical laboratory for testing. In addition, samples may be able to be collected by capillary means, with single use fully retractable lancets, without requiring the needles and trained personnel needed for performing phlebotomy. Furthermore, systems can be deployed into the hot zone or treatment units where assessment and quarantine can be facilitated in real-time through rapid test run times. The system further facilitates real-time reporting and modeling of cases through real-time connectivity to self-learning epidemiological models/software systems, as the assays are run on a system as provided herein for capillary samples in configurations that enable remote connectivity through satellite (so as to not require the presence of cellular networks) and distribution to the places at which patients are being treated and would ideally be tested and/or quarantined.

In embodiments, further assays to simultaneously measure pathogens causing other fevers of unknown origin may also be performed, as well as molecular tests for the other strains of Ebola virus, and hemoglobin and iron tests for anemia. The fevers of unknown origin tests will target these conditions: Lassa fever, malaria, and cholera, (ultimately to be followed by typhoid fever, Marburg, dengue I, II, III and IV, chikungunya, West Nile, and meningitis), with the objective of allowing for better engagement in the screening process through the inclusion of tests associated with fever like symptoms, so that patients may be less afraid to present themselves for testing. The anemia tests are included to facilitate better triaging of patients in the treatment units, focusing on the fact that those infected often have hookworm or other conditions and die of anemia before being able to get treated for the infection itself.

The present methods, devices, systems, and kits provide advantages otherwise not available to detect infectious diseases, and provide improved methods for treating and for preventing the spread of infectious diseases. For example, a real-time diagnostic (RDT) as disclosed herein allows triage of patients at the entrance of every treatment unit. This enables the rapid separation of those patients with Ebola from other patients who have more typical tropical infections such as malaria, typhoid, and *shigella* infections. This reduces the very large risk of these other patients being exposed to Ebola infection on the suspect side of the treatment unit.

In addition, health care workers are commonly infected when they unsuspectingly tend to an Ebola patient without proper personal protective equipment (PPE). Additionally these Ebola patients in new outbreaks often wait in common waiting areas with other people seeking care and are placed on the ward with other non-ebola patients in the hospital. This practice leads to the avoidable exposure of many others to infection. These preventable infections could be drastically curtailed with the availability of a rapid diagnostic test for Ebola as disclosed herein.

The methods, devices, systems, and kits disclosed herein provide means to assess the true distribution and prevalence of Ebola infection within given geographic areas at any given point in time, allowing planning for clinical and logistical support. Better data on the spread of the infection will enable enhanced forecasting of the rates of spread and enabling the focus of awareness training in areas where it would be most effective.

FIG. 1 provides an outline of an exemplary system as disclosed herein. A system for performing analysis of small-volume blood samples in short periods of time may include pre-analytical (sample processing, performed by the SPU as controlled by the LAS), analytical (report generation, performed by the LAS), and post-analytical (report transmission, performed by the LAS) parts.

An exemplary system as described herein comprises the following components operating under oversight of the Clinical Laboratory Improvement Amendments (CLIA)-certified laboratory: the Sample Processing Unit ("SPU"), designed to be deployed to sites where the patients suspected of infection with the Ebola virus will present for diagnosis and treatment ("Field Site"), and a centralized Laboratory Automation System ("LAS"), which is overseen by the CLIA-certified laboratory, running the assays as disclosed herein. Optionally, it should be understood that other embodiments may use one or more other laboratories certified by an authorized body other than CLIA.

A Field Site may be a field location used to diagnose and treat subjects for Ebola virus. Such a site is considered "hot" as potentially infectious Ebola samples are being collected, handled, and disposed. As such, those individuals collecting and handling these specimens must adhere to applicable safety protocols for handing samples presumed to be positive for Ebola virus. The SPU may be used in this environment, and accordingly may be assumed to be contaminated. Individuals using the SPU must use appropriate PPE as required by the Field Site. In embodiments, an SPU may be contained within a protective container, or sheath, or wrapped in plastic or other material in order to reduce or prevent its contamination, or in order to reduce or prevent contamination of its outer surface.

In embodiments, primary applications of the TNAA and ELISA assays are (i) to detect the presence of Ebola Virus RNA and (ii) to detect Ebola IgM and IgG in patients that are symptomatic or at risk for viral Ebola infection, respectively. The primary applications of the Electrolyte assays are to accurately and precisely quantify the concentrations of Sodium and Potassium in patients presenting with signs and symptoms consistent with infection with Ebola virus.

The sample type for Ebola Zaire assays disclosed herein is EDTA-anti-coagulated whole blood collected by fingerstick. The sample type for the ELISA and Electrolyte assays is heparin-anticoagulated plasma collected by a fingerstick as whole blood (processed in the SPU into plasma). EDTA-anti-coagulated and heparin anti-coagulated, as applicable, whole blood samples are collected and introduced into a disposable Cartridge at the Field Site and fed to the SPU, where the samples undergo processing and reaction steps, and are eventually introduced to a detector to yield a set of signals. These signal sets are transferred to the LAS where the raw data are processed and analyzed and oversight is provided, and the relevant reportables (which may include, e.g., raw data, analyzed data, and data plots) are generated.

FIG. 1 shows a schematic diagram of the workflow of the system. Steps illustrated by boxes numbered from 1 to 4 represent pre-analytic steps. Pre-analytic steps include sample collection, sample processing, reagent addition, signal generation, and transmission. Steps illustrated by boxes numbered from 5 to 8 represent analytic steps. Analytic steps include analysis of data received from a device at a sample collection site, oversight, including analysis of controls, calibrations, replicates, outliers, device and sample identification and quality information, and generation of the reportable. Transmission of the report to the health care professional represents a post-analytic step. Post-analytic steps include further review of the analysis of data, and review of report generation and of the report generated for a particular test prior to sign off by CLIA-laboratory personnel and transmission to the care provider who ordered a given test.

For field deployment where access to the internet is not available via wired connectivity, connectivity to a Laboratory Automation System may be maintained via Iridium satellite technology and service. Test results can be configured to be displayed on a Sample Processing Unit that processed the sample, and/or results can be automatically uploaded to a hosted cloud for display to authorized care providers. The system described herein consists of the following components operating under oversight of the Clinical Laboratory Improvement Amendments (CLIA)-certified laboratory: the Sample Processing Unit ("SPU"), designed to be deployed to sites where the patients suspected of infection with the Ebola virus will present for diagnosis and treatment ("Field Site"), and a centralized Laboratory Automation System ("LAS"), which is overseen by the CLIA-certified laboratory, running the assays as disclosed herein.

As shown in the schematic outline of FIG. 1, operation of systems as disclosed herein may follow the schematic outline of the work-flow of methods disclosed herein. In FIG. 1, steps illustrated by boxes numbered from 1 to 4 represent pre-analytic steps. Pre-analytic steps include sample collection, sample processing, reagent addition, signal generation, and transmission. Steps illustrated by boxes numbered from 5 to 8 represent analytic steps. Analytic steps include analysis of data received from a device at a sample collection site, oversight, including analysis of controls, calibrations, replicates, outliers, device and sample identification and quality information, and generation of the reportable. Transmission of the report to the health care professional represents a post-analytic step. Post-analytic steps include further review of the analysis of data, and review of report generation and of the report generated for a particular test prior to sign off by CLIA-laboratory personnel and transmission to the care provider who ordered a given test.

Terms used in FIG. 1 and elsewhere herein include the following.

CLIA-certified laboratory: the Sample Processing Unit ("SPU"), designed to be deployed to sites where the patients suspected of infection with the Ebola virus will present for diagnosis and treatment ("Field Site"), and a centralized Laboratory Automation System ("LAS"), which is overseen by the CLIA-certified laboratory, running the assays as disclosed herein.

Field Site is field location used to diagnose and treat subjects for Ebola virus. The SPU may be used in this environment, and accordingly may be assumed contaminated.

The primary applications of the TNAA and ELISA assays are (i) to detect the presence of Ebola Virus RNA and (ii) to detect Ebola IgM and IgG in patients that are symptomatic or at risk for viral Ebola infection, respectively.

The primary applications of the Electrolyte assays are to accurately and precisely quantify the concentrations of Sodium and Potassium in patients presenting with signs and symptoms consistent with infection with Ebola virus.

In practicing the methods disclosed herein, whole blood samples are collected and introduced into a disposable Cartridge at the Field Site and fed to the SPU, where the samples undergo processing and reaction steps, and are eventually introduced to a detector to yield a set of signals. These signal sets are transferred to the LAS where the raw data are processed and analyzed and oversight is provided, and the relevant reportables are generated.

In embodiments, Ebola Zaire assays disclosed herein use specific primers to detect genomic sequences for Ebola Zaire Nucleoprotein (EZN) and Ebola Zaire Glycoprotein (EZG). For example, the following primers may be used:

Ebola Zaire Nucleoprotein (TH-EZN) primers: specifically detects genomic sequences encoding Ebola Zaire Nucleoprotein (EZN) in whole blood specimens.

Ebola Zaire Glycoprotein (TH-EZG) primers: specifically detects genomic sequences encoding Ebola Zaire Glycoprotein (EZG) in whole blood specimens.

Human Centromeric Repeat (TH-HCR) primers: specifically detects human centromeric repeat (HCR) and is used as a positive control with human clinical specimens to indicate that adequate isolation of nucleic acid resulted from the extraction of the clinical specimen.

RNA Spike-in Control (TH-RNA-SIC) primers: specifically detects synthetic template RNA that is spiked into the clinical specimen before the RNA extraction process. It is used to indicate that adequate isolation of RNA resulted from the extraction of the clinical specimen. Reagents used in the Ebola Zaire TNAA assay include the following:

In embodiments, Ebola Zaire assays disclosed herein may utilize reagents from the following reagent list:

| Reagent | Composition | Vessel | Volume (μL) |
| --- | --- | --- | --- |
| Lysis Buffer | Theranos RNA spike in control 1000 cp/μL in Chemagen Lysis Buffer | RV | 120 |
| Binding Buffer 2 | Ethanol and other components | RV | 240 |
| Wash Buffer 3 | Ethanol and other components | RV | 200 |
| Wash Buffer 4 | Ethanol and other components | RV | 200 |
| Wash Buffer 5 | Ethanol and other components | RV | 200 |
| Elution Buffer | 10 mM Tris-HCl pH 8.0 | RV | 50 |
| Magnetic Beads | M-PVA beads in solution | RV | 15 |
| Poly(A) RNA | Poly(A) RNA in Poly(A) RNA buffer | RV | 1.5 |
| Proteinase K | Dissolved lyophilized proteinase K | RV | 3.5 |
| TNAA Master Mix | T4 buffer, 1.4 mM dNTPs, 0.1% Tween, 400 mM Betaine, Synto Red 59, 0.8 μM oligonucleotide primers | 8X TNAA | 20 |

-continued

| Reagent | Composition | Vessel | Volume (μL) |
| --- | --- | --- | --- |
| TNAA Enzyme Mix | 0.8 U bst, 0.016 RT in T4 buffer | RV | 2 |
| TH EZN-PTC | Synthetic RNA in elution buffer (1000 cp/μL) | TNAA | 3 |
| TH EZG-PTC | Synthetic RNA in elution buffer (10,000 cp/μL) | TNAA | 3 |
| T4 Buffer | 50 mm potassium acetate, 10 mM magnesium acetate, 1 mM dithiothreitol, 20 mM Tris-HCl, pH 7.9 | NA | NA |

The TNAA nucleic acid assay uses primers to bind to and detect nucleic acids indicative of Ebola, e.g., indicative of Ebola Zaire strain of Ebola. Primers may be designed to include nucleic acid portions (or portions comprising nucleic acid analogs, peptide nucleic acids, or other molecules that mimic nucleic acids) that are complementary to any suitable target portion of the Ebola Zaire strain of Ebola. Such primers include complementary portions that are typically at least about 8 bases long, or about 10 bases long, or about 15 bases long, or more. Complementary portions of primers are able to hybridize to target nucleic acids (e.g., Ebola Zaire strain RNA) and so are useful in detecting the presence of, and measuring amounts of, target nucleic acid in a sample.

In embodiments, control material to be used with the Ebola Zaire assays disclosed herein may include the following material.

In embodiments, Ebola TNAA assays disclosed herein include the following controls processed concurrently with every specimen sample:

Ebola Zaire Nucleoprotein Positive Template Control (TH-EZN-PTC): is a positive template control (PTC) designed to react with the TH-EZN primer reagents to indicate whether the Ebola Zaire Nucleoprotein reaction worked. This PTC material consists of synthetic template RNA.

Ebola Zaire Glycoprotein Positive Template Control (TH-EZG-PTC): is a positive template control (PTC) designed to react with the TH-EZG primer reagents to indicate whether the Ebola Zaire Glycoprotein reaction worked. This PTC material consists of synthetic template RNA.

Negative Processing Control (NPC): is a water sample that serves as a negative sample processing control. It is used to ensure no false positive reactions for both the TH-EZN assay and the TH-EZG assay in two separate reactions.

RNA Spike-in Control (TH-RNA-SIC): is a positive template control (PTC) designed to react with the TH-RNA-SIC reagents to indicate adequate isolation of RNA resulted from the extraction of the clinical specimen and amplification.

Protocol for an Ebola Virus Nucleic Acid Assay

In embodiments, all assay steps for an Ebola virus nucleic acid assay may be performed on the SPU. For example, sample preparation and extraction processing, amplification, and detection may all be performed on the SPU.

For example, as disclosed herein, magnetic bead-based sample preparation chemistry may be used; in embodiments, all required reagents may be provided on the assay cartridge, e.g., along with the sample. To avoid sample degradation by RNases in the sample, a sample preservative technology may be used, in which the sample is treated with lithium chloride and iodoacetic acid. The sample preservative reagents are present in Thermos Nanotainer™ Tubes (into which the sample may be collected, and which hold the sample immediately after collection) to help stabilize the sample upon collection from the patient. After collection, the Nanotainer™ Tube containing a sample may be inserted into the cartridge, and the cartridge inserted into a SPU, where the liquid handling unit in the SPU processes the sample to extract RNA for the subsequent pre-amplification reaction followed by the isothermal amplification and detection.

Figure 2A:
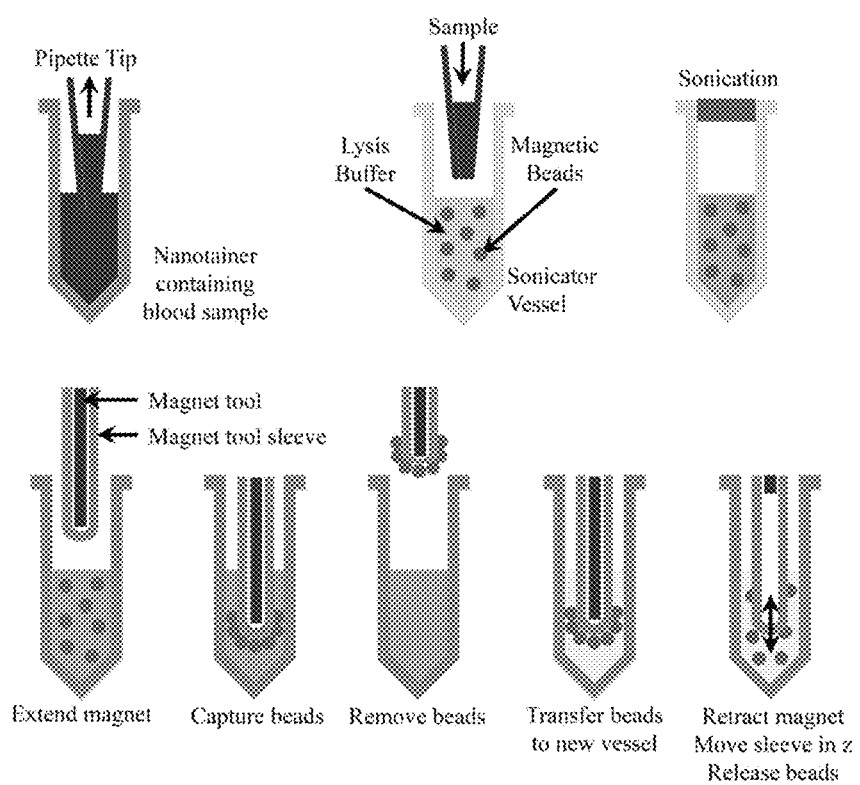
FIG. 2A provides a schematic description of TNAA nucleic acid purification steps. In embodiments, such steps are performed in an automatic sample analysis device or system (e.g., an SPU) and may be performed in the field (e.g., in rural or other locations, and not necessarily within a laboratory, clinic, or hospital setting.

The nucleic acid extraction implemented in the SPU utilizes a magnetic-bead based methodology to isolate and purify the targeted pathogen nucleic acids from the sample. A brief overview of the steps involved in nucleic acid purification as part of the TNAA nucleic acid assay is shown in FIG. 2A. Such steps may be performed by, and may be performed within, an automatic sample analysis device or system, such as an SPU. The operating temperature of an SPU may be set at, and may be controlled to be, at all times, close to a set temperature. In embodiments, the set temperature for operation of an SPU may be, e.g., a temperature selected in the range of from room temperature, or slightly above room temperature, to about 40° C., e.g., may be about 26° C., or be about 27° C., or about 28° C., or about 29° C., or about 30° C., or about 31° C., or about 32° C., or about 33° C., or about 34° C., or about 35° C., or about 36° C., or about 37° C., or about 38° C., or about 39° C., or about 40° C. It will be understood that the temperature may exceed such a range for a period of time, or in portions of the sample analysis device or systems, so that, for example, the temperature may be about 42° C., or about 44° C., or about 46° C., or about 48° C., or about 50° C., or about 52° C., or about 54° C., or about 56° C., or about 58° C., or about 60° C., or about 62° C., or about 64° C., or about 66° C., or about 68° C., or about 70° C., or higher for a period of time, or in portions of the device or system within the housing. FIG. 2A provides a schematic description of TNAA nucleic acid purification steps. In embodiments, such steps are performed in an automatic sample analysis device or system (e.g., an SPU) and may be performed in the field (e.g., in rural or other locations, and not necessarily within a laboratory, clinic, or hospital setting.

The nucleic acid extraction implemented in the SPU utilizes a magnetic-bead based methodology to isolate and purify nucleic acids from a sample matrix.

A brief overview of the steps involved in a magnetic-bead based methodology to isolate and purify nucleic acids from a sample matrix is as follows:

1) For blood samples, a Needle tip is inserted into the sample vessel, to access the sample. The sample is mixed by pipetting up and down for several cycles.

2) For blood samples, the sample is transferred to the Sonicator vessel by means of two large pipette tips. Lysis buffer (that also inactivates ebola virus in the sample) and functionalized magnetic beads are added to the Sonicator vessel from other reagent storage locations on the Cartridge.

3) Binding buffer, which helps the nucleic acids bind to the functionalized magnetic beads, is transferred from a reagent storage well to the Sonicator vessel and mixed by pipetting up and down.

4) The Magnet Tool that resides inside the SPU is picked up using a large pipette nozzle. The Magnet Tool is retracted inside of the nozzle such that only 2-3 mm is visible before that nozzle is used to pick up the Magnet Tool Sleeve in the consumable. This sleeve shields the Magnet Tool from the sample to prevent contamination.

5) The Magnet Tool is then extended into the tip sleeve and inserted into the Sonicator vessel to capture the magnet beads on the exterior of the sleeve.

6) The magnetic beads with captured nucleic acids aggregate on the tip of the sleeve and can be transported into a well containing wash buffer.

7) The Magnet Tool, covered by the Magnet Tool Sleeve, is retracted into the nozzle by moving the piston motor, and the nozzle is moved in a vertical direction multiple times to release the beads and mix them with the fluid. The Magnet Tool/Magnet Tool Sleeve is removed from the well by moving the nozzle.

8) The Magnet Tool is extended back into the tip sleeve and inserted into the wash buffer well to capture the washed magnet beads and transport them to the next step.

9) For each additional bead wash to purify the sample, steps 7 through 9 are repeated.

10) The Magnet Tool and its sleeve carrying captured magnetic beads with purified nucleic acid sample is inserted into the elution well.

11) The Magnet Tool is retracted into the nozzle, and the entire nozzle is moved in vertical directions for several cycles to release the beads and mixed by fluid displacement using a piston motion before retracting the nozzle such that the tip clears the entire well.

12) The released beads are allowed to incubate in the elution well for 1 minute.

13) The Magnet Tool is extended back into the Magnet Tool Sleeve and inserted into the elution buffer well to capture the magnetic beads. The Magnet Tool Sleeve is then discarded into its original location on the Cartridge and the Magnet Tool is returned to its resting location in the SPU.

14) The elution buffer is ready to be distributed into the downstream TNAA assays.

TNAA Assay and Signal Generation

The elution buffer extracted from the steps above contains the extracted nucleic acid material. Detector 3 is brought up to 56° C. utilizing the module's thermal controller. The TNAA tray with the TNAA vessels is picked up by the Liquid Handling Module and transferred to Detector 3. The vessels contain the master mix for the TNAA assay, capped with a wax layer. This wax layer melts at the elevated (56° C.) temperature. 3 uL of elution buffer is aspirated from the elution well on the Cartridge and transferred into the TNAA vessel using a Mini tip, ensuring that the tip penetrates past the molten wax layer. The sample is mixed with the master mix to ensure homogeneity. The tip is discarded back into the Cartridge. When the tip is moved away from the detector module, the lower temperature of the SPU causes the molten wax around the tip to solidify, thereby forming a physical barrier around the tip opening and preventing any sample from leaking out of the tip. This protects against contaminating the SPU. A new tip is picked up by the Liquid Handling Module, and 2 uL of enzyme is transferred from a reagent well in the Cartridge to the NAA vessel, and is mixed with the sample and the master mix. The tip is retracted and returned back to its location on the Cartridge.

The reaction mixture in each NAA vessel is incubated for 5 minutes, after which the photodiode corresponding to each reaction vessel is used to capture the reaction signals of 30 samples sequentially, and capturing such signals of all 30 samples takes slightly over 10 s. After that there is an approximately 10 s pause before capturing the next set, ensuring that each sample is detected at a frequency of 1 detection every 20 s. The data (in the form of counts) is transmitted to the LAS, where the fluorescence signal is recorded and analyzed. The analysis consists of identifying a change point to determine the inflection time of the assay.

Controls for TNAA Assay

Controls are included on board the cartridge for the TNAA assay and include:

1) No Template Control (NTC): For the TH-EZN assay and TH-EZG assay, a NTC test may be run simultaneously to quality control (QC) for background signal and contamination.

2) Positive template controls: for each specimen, positive template controls are run simultaneously for the TH-EZN assay and TH-EZG assays to ensure general performance of the chemistry and the device.

3) Sample collection and transfer control: Each patient sample will carry varying amounts of human specific nucleic acid. For each sample processed, a control human centromeric repeat assay is run to verify appropriate sample collection, sample extraction and device function.

4) Extraction control: A non-natural/synthetic target in the form of RNA is automatically spiked into the sample. This is used as an internal calibrator to QC sample prep and amplification. This test also checks the general performance of the chemistry and the device.

ELISA Assays for the Ebola Virus

In embodiments, an assay for Ebola virus may be directed to Anti-ZEBOV IgG, and may include a solid-phase, three step chemiluminescent enzyme immunoassay. In embodiments, a solid phase, a polystyrene pipette tip, is coated with recombinant EBOV glycoprotein antigen. The patient specimen is first aspirated by this coated tip. After incubation and wash, an alkaline phosphatase (ALP) conjugated goat anti-human IgG is aspirated by the tip. After incubation and wash, a chemiluminescent substrate is aspirated by the tip. This substrate undergoes hydrolysis due to ALP, the emitted photons are measured by the Luminometer module and related to the presence of anti-ZEBOV IgG antibodies in the sample.

In embodiments, Anti-ZEBOV IgM is a solid-phase, four step chemiluminescent enzyme immunoassay. The solid phase, a polystyrene pipette tip, is coated with mouse anti-human IgM. The patient specimen is first aspirated by this coated tip. After incubation and wash, EBOV glycotprotein antigen is aspirated by this tip. After further incubation and wash, an alkaline phosphatase (ALP) conjugated mouse anti-ZEBOV IgG is aspirated by the tip. After incubation and wash, a chemiluminescent substrate is aspirated by the tip. This substrate undergoes hydrolysis due to, the emitted photons are measured by the Luminometer module and related to the presence of anti-ZEBOV IgM antibodies in the sample.

For the ELISA assays, there are positive and negative controls run simultaneously with the assay each time an assay is run. These controls are processed in exactly the same way as the patient samples are processed (cf. ELISA protocol). The output from these control runs are used to look for any performance deficiencies in the system in real-time, thereby helping to ensure that the sample output is accurate. If any of the two controls do not pass, the result from that assay may be considered invalid.

| Assay | Capture reagent | Detection reagent | Assay Principle |
|---|---|---|---|
| anti-Ebola IgM | Mouse anti-human IgM and recombinant EBOV glycoprotein antigen | alkaline phosphatase (ALP) conjugated mouse anti-ZEBOV IgG | ELISA |

-continued

| Assay | Capture reagent | Detection reagent | Assay Principle |
|---|---|---|---|
| anti-Ebola IgG | recombinant EBOV glycoprotein antigen | alkaline phosphatase (ALP) conjugated goat anti-human IgG | ELISA |

Reagent List for the Ebola IgG and IgM Assays:

Reagents used in the antibody assays as disclosed herein are described and listed in the following table (Table 1).

TABLE 1

Ebola IgG and IgM Assay reagent list:

| REAGENT | COMPOSITION | VESSEL | VOLUME (μL) |
|---|---|---|---|
| Assay diluent buffer | 3% BSA in 1x TBS | 2 × Wash well | 100 |
| Inactivation agent | 12% Acetic acid (TBD) | RV | 50 |
| Neutralization agent | 6M NaOH (TBD) | RV | 50 |
| Assay Wash Buffer | 0.1% Tween in 500 mM NaCl | 24 × RV | |
| Conjugate: IgG assay | Goat anti-human IgG conjugated with ALP | 6 × RV | 50 |
| Conjugate: IgM assay | Goat anti-human IgM conjugated with ALP | 6 × RV | 50 |
| Chemiluminescent substrate | | 12 × RV | 50 |
| Positive Control | Serum based | RV | 50 |
| Negative Control | Serum based | RV | 50 |
| Coated tips: IgG | | 12 × Mini tip | NA |

Protocol for Ebola Antibody ELISAs

The antibody ELISA protocol starts with whole blood samples and extracts plasma for the analytical test. Lysis agents are added to the extracted plasma (and residual cells) to inactivate any ebola virus in the sample before further processing in the SPU. The following is the sequence of steps for the antibody assays with the extracted, inactivated plasma.

1. A Large tip is picked up, and 18 uL of diluent is transferred from the Wash vessel to 4 Round vessels. The tip is ejected back in the Cartridge.
2. 4 Mini tips are picked up, and 2 uL of sample is aspirated in each tip, and dispensed into the 4 Round vessels.
3. The mixture is mixed well by pipetting the fluid back and forth.
4. 4 coated Mini tips, corresponding to the four assays, each aspirate 10 uL of the mixture, and the mixture is allowed to incubate with the capture protein on the surface for 10 minutes.
5. The mixture is discarded onto an absorbent waste pad located on the Cartridge, which ensures that the waste fluid is retained to prevent any possible contamination.
6. The 4 tips aspirate 11 uL of wash buffer, followed by a 1 minute incubation, after which the wash buffer is discarded onto the waste pad.
7. Step 6 is repeated 5 more times.
8. The 4 tips aspirate 10 uL of detection antibody, followed by a 5 minute incubation.
9. The fluid is discarded onto an absorbent pad, and the wash steps (steps 7 and 8) are repeated.
10. The four reaction tips aspirate 10 uL of ALP substrate from 4 sealed Round vessels containing substrate, followed by a 1 minute incubation.

11. The four tips are moved to the Luminometer Module where luminescence of each of the four tips is detected, and the corresponding count values transmitted to the LAS.

The count values are analyzed in the LAS, where a calibration function is applied, analysis is performed on these values and associated replicate, control, calibrator, QC, and outlier evaluation, and the final antibody results are generated.

Assays for Electrolyte Imbalance Management

Electrolyte Assay Principle:

The electrolyte assays disclosed herein are a subset of general chemistry assays which may be performed using an automatic sample analysis device or system. The general chemistry assays disclosed herein cover common clinical chemistry tests including measuring electrolytes, such as sodium and potassium, renal function tests, liver function tests, minerals, and metabolites. The sodium and potassium assays described herein adopt the following methodology: Plasma is separated from whole blood by centrifugation inside the SPU, and the plasma is diluted in either water or saline, and mixed with reagent(s). The reaction mixture(s) is incubated as required for each assay. The proceeding reaction results in a solution which absorbs light at a particular wavelength, which is detected on Detector 4. This raw signal is transmitted to and analyzed by the LAS to generate the intensity spectra, which is proportional to the concentration of the respective analyte according to Beer-Lambert law.

Sodium Assay—Overview:

Sodium is an essential electrolyte and mineral in the body. It helps keeps fluids and electrolytes balanced in the body. The concentration of sodium measured in the blood is a reflection of the amount of sodium and the amount of water in the vascular space.

The amount of sodium in the body is partially controlled by aldosterone, a hormone made by the adrenal glands. Aldosterone levels in the body tell the kidneys how much sodium should be excreted and how much sodium should be retained in the body. Sodium is also found in a majority of foods and medications. Too much sodium intake may raise a person's blood pressure and put them at a greater risk for developing heart disease/heart failure, stroke, and kidney damage. Hyponatremia (low sodium in the body) is very rare, but most often occurs in people who take medications which causes increased urination.

Sodium assays are important in assessing acid-base balance, water balance, water intoxication, and dehydration. As discussed above, evaluation of sodium levels is important in the evaluation and treatment of patients presenting with signs and symptoms of Ebola virus infection.

Sodium Assay—Principle of the Method:

In the Sodium colorimetric assay disclosed herein, the sodium dependent enzyme β-galactosidase cleaves the substrate o-nitrophenyl-β-D-galactopyranose, yielding the product onitrophenol, a dye with color intensity at 405/420 nm. This absorption is detected by the SPU, with the raw signal transmitted to the LAS, where it is analyzed to generate a concentration of sodium based on the rate at which o-nitrophenol is formed. This Sodium assay is designed to detect Sodium in plasma with a reportable range of about 90-200 mM.

o-nitrophenyl-β-D-galactopyranose (ONPG) $\xrightarrow[\beta\text{-galactosidase}]{Na^+}$ -continued o-nitrophenol + Galactose (read @ 405/420 nm)

Potassium Assay—Overview:

Potassium is the major cation of the intracellular fluid. It is an important mineral and electrolyte in the body. It is necessary for proper functioning of the heart, nerves, kidneys, muscles, and the digestive system. Disturbance of potassium homeostasis (intra- and extracellular) can cause serious health effects. Decreases in extracellular potassium are characterized by muscle weakness, irritability, and eventual paralysis. Cardiac effects include tachycardia, other cardiac conduction abnormalities that are apparent by electrocardiographic examination, and eventual cardiac arrest. Hypokalemia is common in vomiting, diarrhea, alcoholism, and folic acid deficiency. Additionally, >90% of hypertensive patients with aldosteronism have hypokalemia. Abnormally high extracellular potassium levels produce symptoms of mental confusion; weakness, numbness and tingling of the extremities; weakness of the respiratory muscles; flaccid paralysis of the extremities; slowed heart rate; and eventually peripheral vascular collapse and cardiac arrest. Hyperkalemia may be seen in end-stage renal failure, hemolysis, trauma, Addison's disease, metabolic acidosis, acute starvation, dehydration, and with rapid potassium infusion. As discussed above, evaluation of Potassium levels is important in the evaluation and management of patients presenting with signs and symptoms of Ebola virus infection.

Potassium Assay—Principle of the Method:

Potassium is normally maintained in levels from 3.5 to 5.5 mM within the body and most test methods only read out to 8 mM, making for a very narrow assay range. Potassium levels are often determined using ion selective electrodes or flame photometry. A potassium assay may use a sodium tetraphenylborate method for the determination of potassium levels. In this method the compound Sodium Tetraphenylborate reacts with potassium from plasma. K+ replaces Na+ from Sodium Tetraphenylborate (NaTPB) to form potassium tetraphenylborate, a white precipitate. The precipitate remains in suspension with the help of some thickeners and stabilizers, causing an increase in turbidity. The resulting increase in turbidity is detected by the SPU at 450 nm. This raw signal is transmitted to the LAS, where it is analyzed to generate the concentration of potassium. The assay has a reportable range of about 0.1-7.5 mM for Potassium.

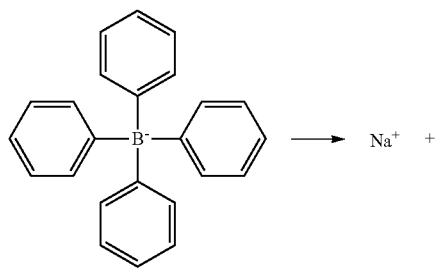

Reagent Lists for Sodium Assay and Potassium Assays

Reagents used in the electrolyte assays (sodium assay and potassium assay) as disclosed herein are described and listed in the following table (Table 2).

TABLE 2

Sodium and Potassium Assay reagent list:

| ASSAY | REAGENT | COMPOSITION | CONCENTRATION | VOLUME (µL) | VESSEL |
|---|---|---|---|---|---|
| Sodium | A | Cryptand β-D-galactosidase | >0.4 mM <8 U/mL | 1 × 160 µL | 1 Wash Strip |
| | B | O-Nitrophenyl β-D-galactosidase | >0.5 mM | 3 Vessels × 65 µL | 3 vessels |
| | Medical Decision Level Control 1 | Serum Based | 135 mM | 60 | Round vessel |
| | Medical Decision Level Control 2 | Serum Based | 150 mM | 60 | Round vessel |
| Potassium | A | Sodium Tetraphenyl Borate | <100 mM | 1 × 160 µL | 1 Wash strip |
| | Medical Decision Level Control 1 | Serum Based | 3.0 mM | 60 | Round vessel |
| | Medical Decision Level Control 2 | Serum Based | 7.5 mM | 60 | Round vessel |

The Ebola assays disclosed herein have been validated using the components referenced above. These Ebola assays were developed using primers and probes directed to Ebola Zaire strain viral nucleic acids, and antigens and antibodies indicative of the presence of Ebola Zaire strain virus and of a subject's immune response to such virus.

Figure 2B:
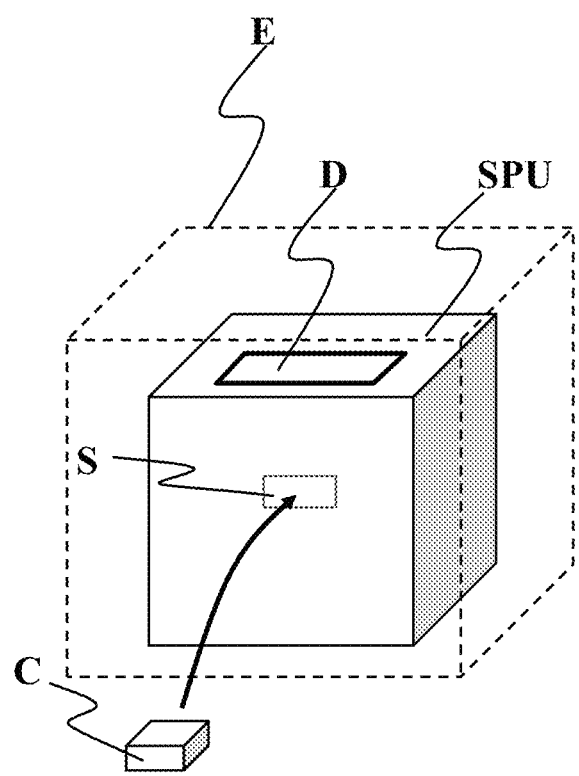
FIG. 2B shows a simplified depiction of one embodiment of SPU and one embodiment of a cartridge as described herein.

By way of non-limiting example, FIG. 2B shows a simplified view of one embodiment of an SPU that may be used herein. The Ebola assays disclosed herein have been validated using automatic sample analysis devices such as but not limited to those disclosed herein and in, e.g., U.S. Pat. Nos. 8,088,593; 8,380,541; 8,435,738; 8,475,739; 8,840,838; U.S. patent application Ser. No. 13/933,035, filed Jul. 1, 2013; U.S. patent application Ser. No. 13/769,820, filed Feb. 18, 2013; U.S. patent application Ser. No. 14/183,503, filed Feb. 18, 2014; and U.S. patent application Ser. No. 14/214,850, filed Mar. 15, 2014.

Referring still to FIG. 2B, an SPU may be configured to have a display D which may be touchscreen or non-touch screen display. The display D may be on a top surface, a front surface, an angled top surface, or a side surface of the SPU. As seen in FIG. 2B, a cartridge C which may contain all reagents, diluents, pipette tips, and/or other disposable used to perform all testing herein, is configured to be received in a cartridge insertion location S of the SPU. Optionally, a cartridge C which may contain substantially all reagents, diluents, pipette tips, and/or other disposable used to perform all testing herein, is configured to be received in a cartridge insertion location S of the SPU. In one example the cartridge C may contain all reagents except perhaps a common diluent (such as water or the like) or a common reagent used in processing. Optionally, at least some pipette tips in the cartridge C are coated (inside of tip or outside of tip) with an ebola antibody such as described herein. In one non-limiting example, the cartridge C is configured with assay(s) for diagnostic marker(s) and assay(s) for prognostic marker(s) for the disease at issue.

Optionally, some embodiments may use a further containment enclosure E about the SPU which in manner similar to a fume hood glove box, may include one or more ports or other devices that allow for protected access. In one non-limiting example, the enclosure E may be configured to have hardware to implement a negative pressure environment to minimize the risk of contaminants escaping the enclosure. Optionally, some embodiments may configure the SPU to have the negative pressure environment within the SPU. In embodiments, a containment enclosure E may include one or more air filters, e.g., high efficiency particulate air (HEPA) filters suitable for blocking the flow of contaminants and micro-organisms. In embodiments, such air filters may filter outside air as it flows into, or may filter internal air as it leaves, or both, the interior of the containment enclosure. Such filters may be effective to reduce or prevent the entry of dust or other contamination into the SPU, and to reduce or prevent contamination from exiting the SPU (including reducing or preventing contamination from samples from exiting an enclosure E).

The assays have been completed within 1 hour of loading the sample into the cartridge and inserting the cartridge into the automatic sample analysis device.

Assay Results

Figure 3:
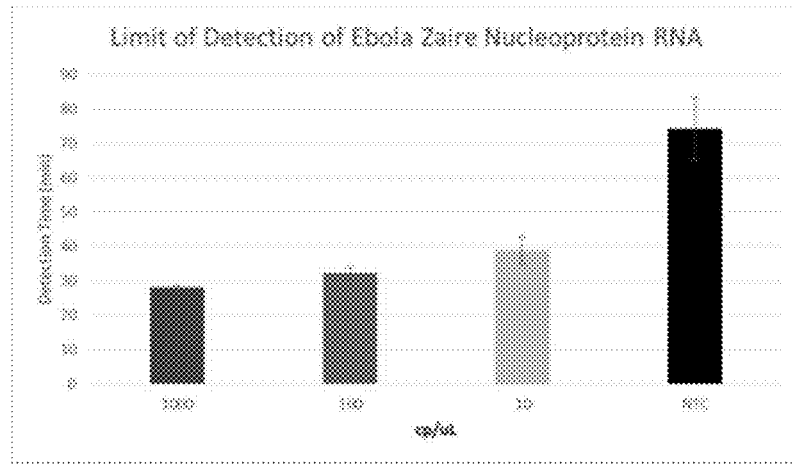
FIG. 3 illustrates experiments performed which show limits of detection (LOD) of the TNAA nucleic acid assay as applied to Ebola Zaire viral nucleoprotein RNA. As shown in the figure, titration of synthetic RNA target encoding Ebola Zaire nucleoprotein shows an LOD as low as 10 copies/uL. The y-axis shows the time of detection based on the fluorescent signal recorded in real-time during the TNAA amplification reaction (i.e., the amplification reaction performed in a TNAA nucleic acid assay). The cutoff for assessing a positive reaction was 45.6 minutes.
Figure 4:
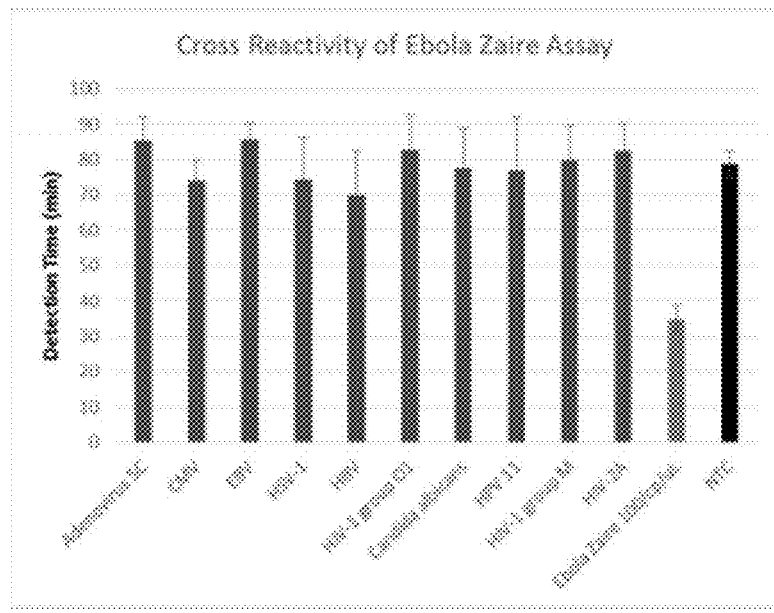
FIG. 4 illustrates experiments performed which show amounts of cross-reactivity of the TNAA nucleic acid assay as applied to Ebola Zaire viral nucleoprotein and potential cross-reactants. The cross reactivity of the TH-EZN reaction to other pathogens is shown here. No false positive reaction was seen. The positive control is labeled "Ebola Zaire 100/cp/uL". The non-template control is labeled "NTC". The y-axis shows the time of detection based on the fluorescent signal recorded in real-time during the TNAA amplification reaction. The cutoff for assessing a positive reaction was 45.6 minutes.

The results of TNAA assays directed at Ebola virus (Ebola Zaire strain) are shown in FIGS. 3-8. The data shown in FIG. 3 demonstrate performance data of the Ebola Zaire TNAA Assay. These data are for the TH-EZN reaction which detects the presence of the Ebola Zaire nucleoprotein RNA. FIG. 3 shows results from titration experiments using synthetic RNA target for Ebola Zaire nucleoprotein. The y-axis shows the time of detection based on the fluorescent signal recorded in real-time during the TNAA amplification reaction. The time-cutoff for assessing a positive reaction was 45.6 minutes. As few as 10 copies/uL (cp/uL) of synthetic Ebola Zaire nucleoprotein RNA was detectable in these experiments.

FIG. 3 plots the detection time in minutes (vertical axis) versus the copies per microliter (cp/uL) for four conditions: 1000 copies per microliter (cp/μL) of Ebola Zaire nucleoprotein RNA (left-most column), 100 cp/μL of Ebola Zaire nucleoprotein RNA (second from left column), 10 cp/μL of Ebola Zaire nucleoprotein RNA (second from right column), and "NTC" (no template control) in which no Ebola Zaire nucleoprotein RNA was present (right-most column). As shown in FIG. 3, the presence of Ebola RNA was detectable in less than 30 minutes for samples having 1000 cp/μL of Ebola Zaire nucleoprotein RNA; Ebola RNA was detectable in slightly more than 30 minutes for samples having 100 cp/μL of Ebola Zaire nucleoprotein RNA; even in samples having only 10 cp/μL of Ebola Zaire nucleoprotein RNA, Ebola RNA was detectable in less than 40 minutes. For comparison, (non-specific) signals from samples with no Ebola Zaire nucleoprotein RNA were not detected for times greater than about 70 minutes, and so are clearly distinguishable from clinically significant signals indicative of the presence of Ebola RNA.

The data shown in FIG. 4 demonstrate the performance of the Ebola Zaire nucleoprotein TNAA Assay in the presence of possibly cross-reacting substances. No false positive reaction was observed, as the detection time for all possibly cross-reacting pathogens was substantially longer than the cutoff time (45.6 minutes). The detection time for Ebola Zaire RNA at 100 cp/μL was substantially below the cutoff time, indicating positive detection of the target viral nucleic acid in the sample. No cross reactivity of the TH-EZN reaction to other pathogens in the assay shown was observed.

In FIG. 4, as in FIG. 3, the y-axis shows the time of detection based on the fluorescent signal recorded in real-time during the TNAA amplification reaction. Thus, the vertical axis plots detection time (in minutes) based on the fluorescent signal recorded in real-time during the TNAA amplification reaction. Columns heights indicate the time in minutes until an inflection in the measured fluorescent signal was identified; each column is labeled with the name of the pathogen nucleic acid presented for detection. The column labeled "Ebola Zaire 100 cp/uL" is the positive control. The non-template control is labeled "NTC" (no RNA target added). Natural or synthetic pathogen nucleic acids tested included nucleic acids from several forms of human immunodeficiency virus (HIV), Herpes Simplex Virus 1 (HSV-1), adenovirus SC, cytomegalovirus (CMV), Epstein-Barr virus (EBV), *Candida albicans*, human papilloma virus (HPV), herpes simplex virus (HSV), hepatitis B virus (HBV), and other pathogens. The cutoff for assessing a positive reaction was 45.6 minutes; only the signal for detection of Ebola Zaire was below the cutoff, indicating a positive reaction. It is notable that, for all pathogen RNA targets except Ebola Zaire, the column heights are similar to that of the NTC column height, indicating no detectable cross-reactivity.

As shown in FIG. 5, the specificity of the TH-EZN reaction was tested by adding the listed pathogens to the sample in addition to the positive control synthetic templates. No false negative reactions were seen. The positive control is labeled "Ebola Zaire 100/cp/ul". The non-template control is labeled "NTC". The y-axis shows the time of detection based on the fluorescent signal recorded in real time during the TNAA amplification reaction. The cutoff for assessing a positive reaction was 45.6 minutes.

The data shown in FIG. 5 demonstrate the specificity of the Ebola Zaire nucleoprotein TNAA Assay in the presence of possibly interfering substances. The specificity of the TH-EZN assay is quite good, as the detection time is not much affected by the presence of other pathogens, as shown in the figure. The same possible interfering pathogens as tested in the experiments shown in FIG. 4 were used in the experiments shown in FIG. 5 (forms of human immunodeficiency virus (HIV), Herpes Simplex Virus 1 (HSV-1), adenovirus SC, cytomegalovirus (CMV), Epstein-Barr virus (EBV), *Candida albicans*, human papilloma virus (HPV), herpes simplex virus (HSV), hepatitis B virus (HBV)).

The Table shown in FIG. 6 further illustrates the experiments performed which demonstrate the specificity of the Ebola Zaire nucleoprotein TNAA Assay in the presence of possibly interfering substances. The effect of interfering substances was tested for the TH-EZN reaction in two manners. First interfering substances were added to the sample in addition to the positive control synthetic templates to see if the substances interfered with the reaction. Second, interfering substances were added to a sample without any template (NTC) to assess if a non-specific reaction occurred. Each substance was tested at two levels (lx concentration and 0.1× concentration). As shown in FIG. 6, none of the possibly interfering substances prevented the detection of synthetic Ebola Zaire nucleic acid (columns labeled "inhibits true positive"). As shown in FIG. 6, only one of the possibly interfering substances, and only at the higher concentration, caused a false positive (hemoglobin at 5 g/L concentration). Thus, the Ebola Zaire TNAA Assay is quite robust.

The Ebola Zaire ELISA assays for detecting the presence of anti-Ebola virus IgG and IgM antibodies in samples (ZEBOV IgG and ZEBOV IgM assays, where ZEBOV stands for Zaire Ebola Virus), along with the Ebola Zaire ELISA assays for detecting the presence of GP antigen in samples (ZEBOV GP antigen assay), are suitable for the qualitative detection of IgM and IgG antibodies for Ebola virus and the quantitative measurement of ZEBOV GP antigen, all from EDTA anti-coagulated plasma (extracted from whole blood specimens). EDTA coagulated whole blood or plasma may be obtained, for example, by fingerstick, or may be obtained by other methods of drawing blood samples. These assays may also be performed on serum samples, which may be obtained, for example, by venipuncture. All of such samples may be obtained, for example, from individuals in affected areas with signs and symptoms of Ebola virus infection.

FIGS. 7A and 8A show the results of Ebola Zaire ELISA assays. The data shown provide performance data of the Ebola Zaire ELISA IgG and IgM Assays, and demonstrate detection of targets in the samples. FIG. 7A provides a comparison of in-house (negative) EDTA-anticoagulated plasma samples and high-concentration spiked samples. All samples in FIG. 7A were spiked with human anti-ZEBOV IgG to a nominal concentration of 1 ug/ml. FIG. 8A provides a comparison of in-house (negative) EDTA-anticoagulated plasma samples and low-concentration spiked samples. All samples in FIG. 8A were spiked with human anti-ZEBOV IgM to a nominal concentration of 0.3 ug/ml. As discussed above, the IgG and IgM assays (ELISA assays) may be performed in heparin-anticoagulated plasma samples or in EDTA-anticoagulated blood samples (e.g., whole blood or plasma); such samples may be collected by a fingerstick as whole blood, and then EDTA or heparin applied to whole blood or plasma.

For the qualitative assays (Ebola Zaire ELISA IgG and IgM Assays), the assay output is antibody index or antibody titer, which is directly related (but may not be quantitatively identical to) antibody titer. The antibody index is a continuum as opposed to the final output of the assay which is discrete/categorical. For the ZEBOV GP antigen assay which is a quantitative assay the measuring interval will span 2500-25 ng/ml of the GP antigen.

Anti-ZEBOV IgG assay: FIG. 7B shows a dose response as demonstrated by spiking pooled normal serum samples with a human anti-ZEBOV IgG clone at concentrations ranging from 0.05-500 ug/mL. EDTA plasma samples from n=40 in house normal donors was also tested. FIG. 7B compares assay results from negative and spiked samples; the figure shows signals from assays run with in-house (negative) EDTA-anticoagulated plasma samples (squares) and spiked samples. All samples were spiked with human anti-ZEBOV IgG. Putative cut-off set at signal 1.8 corresponds to a sensitivity of 0.5 ug/ml. The antigen used in this anti-ZEBOV IgG assay shows reactivity for antibodies against glycoprotein as well as other proteins of ZEBOV. Mild cross reactivity with Sudan EBOV IgG is also seen. Cross reactivity data is summarized in the Table shown in FIG. 7C.

As discussed above, FIG. 8A compares ZEBOV IgM ELISA assays results from (negative) EDTA-anticoagulated plasma samples with results from low-concentration spiked samples. FIG. 8B also compares assay results from negative and spiked samples, showing results from the Anti-ZEBOV IgM assay; the figure shows signals from assays run with in-house (negative) EDTA-anticoagulated plasma samples (squares) and spiked samples. The dose response shown in FIG. 8B is demonstrated by spiking pooled normal serum samples with a human anti-ZEBOV IgM control at concentrations ranging from 1 to 10 μg/mL. EDTA plasma samples from 12 normal donors was also tested. Putative cut-off was set at signal 1.5. All samples were spiked with human anti-ZEBOV IgM.

FIG. 9A shows dose-response results from assays with recombinant ZEBOV GP antigen spiked pooled normal serum calibrators. Recombinant ZEBOV GP antigen was spiked into pooled normal donor serum at concentrations ranging from 2.5 μg/mL to 25 ng/mL. FIG. 9A shows the dose response curve of the assay. The antibody pair used in this assay is very specific for the ZEBOV GP antigen and does not cross-react with the GP antigen from the Marburg genus virus. There is also no cross-reactivity seen with GP antigens form the other species of Ebola virus, and against other viral proteins in the ZEBOV genome. This cross-reactivity data is summarized in the Table shown in FIG. 9B.

Methods of Interpreting the Assay Results

All test controls should be examined prior to interpretation of patient results. If the controls are not valid, the patient results cannot be reliably interpreted. Assessment of clinical specimen test results should be performed after the positive and negative controls have been examined and determined to be valid and acceptable. Assay results may be compared to Ebola Zaire TNAA assay positive and negative controls, and may be reported as positive, equivocal, or negative for Ebola Zaire.

Interpretation of Nucleic Acid Assay Results:

Both TH-EZN and TH-EZG reactions should be positive for a positive Ebola test result. If only one of these reactions is positive, then the results are inconclusive and a retest is required. Both TH-EZN and TH-EZG reactions should be negative for a negative Ebola test result.

In order for a test run to be valid, all NTC reactions must be negative. If one or more NTC fails, the entire run is invalid and potential sources of contamination should be identified and corrected, and the specimen retested. Failure to achieve a positive PTC reaction for any of the assays (TH-EZN-PTC and TH-EZG-PTC) invalidates the run.

The TH-RNA-SIC assay and TH-HCR assay should both be positive. All runs should exhibit a positive TH-RNA-SIC assay. A negative TH-RNA-SIC assay could indicate improper RNA extraction, low recovery of RNA, improper reaction, reagent or equipment malfunction, or amplification inhibition.

All clinical specimens should exhibit a positive HCR reaction, indicating sufficient recovery of acceptable quality RNA from the specimen. A negative TH-HCR reaction could indicate improper RNA extraction, low recovery of RNA, improper reaction, reagent or equipment malfunction, amplification inhibition, or absence of sufficient human cellular material in the specimen to enable detection.

In embodiments, positive results for Ebola Zaire assays disclosed herein should override a failed (negative or uncertain) TH-RNA-SIC assay or TH-HCR assay result for that clinical specimen. In embodiments, a failed TH-RNA-SIC assay or TH-HCR assay reaction that accompanies a negative or uncertain target result requires retesting.

The following table provides an overview of nucleic acid assay results and their interpretation.

| TH-EZN | TH-EZG | TH-EZN-PTC | TH-EZG-PTC | TH-EZN-NTC | TH-EZG-NTC | TH-RNA-SIC | TH-HCR | Interpretation | Follow-up |
|---|---|---|---|---|---|---|---|---|---|
| + | + | + | + | − | − | + | + | Positive | |
| − | − | + | + | − | − | + | + | Negative | |
| + | − | + | + | − | − | + | + | Inconclusive | Retest |
| − | + | + | + | − | − | + | + | Inconclusive | Retest |
| | | − | | | | | | Invalid Run | Retest |
| | | | − | | | | | Invalid Run | Retest |
| | | | | + | | | | Invalid Run; possible contamination | Retest |
| | | | | | + | | | Invalid Run; possible contamination | Retest |
| − | − | | | | | − | | Extraction or Reagent Failure | Retest |
| − | − | | | | | | − | Invalid run or low sample quality | Retest |
| + | + | + | + | − | − | + | − | Positive | |
| + | + | + | + | − | − | − | + | Positive | |
| + | + | + | + | − | − | − | − | Positive | |

Interpretation of Antibody Assay Results:

Interpretation of the results of assays for anti-Ebola antibodies (ELISA assays) are discussed in the following.

A negative Anti-ZEBOV IgG result indicates no evidence of recent of past Ebola infection. Results must be interpreted in the context of clinical presentation. A negative Anti-ZEBOV IgG result does not rule out other etiologies.

A positive Anti-ZEBOV IgG result indicates recent or chronic Ebola infection. Results must be interpreted in the context of clinical presentation. A positive Anti-ZEBOV IgG result does not rule out co-infection or other etiologies.

An equivocal Anti-ZEBOV IgG result cannot determine Ebola status. Retesting of the subject after 1-2 weeks is indicated if symptoms persist.

A negative Anti-ZEBOV IgM result indicates no evidence of acute Ebola infection. Results must be interpreted in the context of clinical presentation. A negative Anti-ZEBOV IgM result does not rule out other etiologies.

A positive Anti-ZEBOV IgM result indicates acute Ebola infection. Results must be interpreted in the context of clinical presentation. A positive Anti-ZEBOV IgM result does not rule out co-infection or other etiologies.

An equivocal Anti-ZEBOV IgM result may not determine Ebola status. Retesting of the subject after 1-2 weeks is indicated if symptoms persist.

Controls: Each assay (Ebola IgG and Ebola IgM) is run with a positive and a negative control. If any of the controls do not pass, the results from that run may be considered invalid.

A ZEBOV GP antigen assay result that is greater than the lower limit of quantification (LLOQ) of the assay indicates an acute Ebola infection. Results must be interpreted in the context of clinical presentation, e.g., indication of an acute Ebola infection does not rule out co-infection or other etiologies as well.

A ZEBOV GP antigen assay result that is lower than the lower limit of quantification (LLOQ) of the assay indicates no evidence of an acute Ebola infection. Results must be interpreted in the context of clinical presentation, e.g., such a result does not rule out other etiologies.

Controls: Each ZEBOV GP antigen assay may be run with a positive and a negative control. If any of the controls do not pass, the results from that run may be considered invalid.

Interpretation of Electrolyte Assay Results:

Interpretation of the results of assays for sodium and for potassium are discussed in the following.

Sodium and potassium results should be interpreted based on routine clinical practice and help guide the care provider in administering supportive care including oral and/or intravenous (IV) fluids to maintain fluids and electrolytes.

Controls: Each assay (sodium and potassium) is run with a low and a high control. If any of the controls do not pass, the results from that run should be considered invalid.

Measurement of sodium levels in samples obtained from subjects suspected of suffering from an infectious disease such as Ebola, e.g., Ebola Zaire strain, is useful in providing and managing the treatment of that subject. Measurement of potassium levels in samples obtained from subjects suspected of suffering from an infectious disease such as Ebola, e.g., Ebola Zaire strain, is useful in providing and managing the treatment of that subject. Measurement of electrolytes such as sodium and potassium may be of particular use in providing and managing the treatment of subjects suffering from hemorrhagic diseases, such as Ebola, or other diseases which cause fluid loss (e.g., cholera).

Example 2

Nucleic acid sequences of Ebola viruses include, for example, Ebola Zaire nucleoprotein nucleic acid sequence, NCBI GenBank AF272001 Ebola Zaire (Mayinga strain) Nucleoprotein (SEQ ID NO: 1). (The nucleic acid sequence of SEQ ID NO: 1, and the other nucleic acid sequences provided herein, are written as the DNA sequence (i.e., where the RNA has uracil (u) the DNA has thymine (t)). Nucleic acid sequences encoding Ebola virus proteins include, for example, Ebola Zaire nucleoprotein (NCBI GenBank J04337.1 Ebola Zaire (Mayinga strain) (SEQ ID NO: 2)), and include, for example, the nucleic acid sequence encoding Ebola virus glycoprotein (NCBI GenBank U23187.1 Ebola Zaire (Mayinga strain) (SEQ ID NO: 3).

The amino acid sequences of Ebola virus proteins include the nucleoprotein amino acid sequence encoded by the above Ebola Zaire nucleoprotein, which has the amino acid sequence found in NCBI GenBank J04337.1 Ebola Zaire (Mayinga strain) (SEQ ID NO: 4). A further Ebola virus nucleoprotein amino acid sequence, for example, is Ebola Zaire nucleoprotein amino acid sequence, Uniprot Accession No. P18272 (version P18272.2, GI 6136281) (SEQ ID NO: 5). The amino acid sequences of Ebola virus proteins include, for example, the glycoprotein sequence encoded by the nucleic acid sequence mentioned above, which has the amino acid sequence found in NCBI GenBank U23187.1 Ebola Zaire (Mayinga strain) (SEQ ID NO: 6).

Further Ebola virus nucleic acid sequences (from which the amino acid sequences of Ebola virus proteins may be determined) are found, for example, listed by the National Center for Biotechnology Information (NCBI) (main URL: http://www.ncbi.nlm.nih.gov/) Bioproject for Zaire ebolavirus (Zaire ebolavirus genome sequencing) Accession No. PRJNA257197, ID No. 257197, all of which sequences are hereby incorporated by reference in their entireties. The amino acid sequences listed therein, the amino acids encoded by these nucleic acid sequences, and portions thereof, including C-terminal portions, may be antigenic, leading to anti-Ebola antibodies when present in an infected individual, and when presented to an experimental animal or organism in an artificial (e.g., laboratory-based) method for producing antibodies. Antibodies to Ebola virus antigens are discussed, for example, in *Virus Research* 176(0):83-90 (2013), which is hereby incorporated by reference in its entirety.

While the assays, methods, kits, devices, and systems have been described and illustrated with reference to certain particular embodiments thereof, those skilled in the art will appreciate that various adaptations, changes, modifications, substitutions, deletions, or additions of procedures and protocols may be made without departing from the spirit and scope of the invention. By way of example and not limitation, although many embodiments are described in the context of using TNAA, it should be understood that some other embodiments of systems, methods, devices, and/or kits herein may use other types of nucleic acid amplification (isothermal and/or thermal-cycled) currently known or other types of nucleic acid detection methods that may be developed in the future. It should also be understood that although many of the embodiments herein are described in regards to Zaire ebolavirus, the embodiments herein can be applied to other strains currently known (Sudan, Reston, Tai Forest, or Bundibugyo) or may be discovered in the future. It should also be understood that many of the samples analyzed herein are blood samples (capillary, venous, arterial, etc. . . . ), some embodiments may also be configured to process samples from oral swabs or tissues samples (spleen, liver, skin snips) that may be obtained by techniques such as biopsy. It should also be understood that embodiments herein may involve analysis of samples with EDTA and/or samples with heparin (from same subject). Samples to be transported for processing may be stored at about 4° C., optionally in the range of about 2° C. to about 6° C.

Example 3

Analytical Sensitivity of the ZEBOV GP Antigen Assay

The Zaire Ebola virus (ZEBOV) GP antigen assay is an antigen capture ELISA that is highly specific for the Zaire Ebola virus glycoprotein. The assay uses low sample volume and is designed for automated analysis of the ZEBOV GP antigen detection. The reagent coated on the surface of the Zaire Ebola Virus (ZEBOV) GP antigen assay is a protein A-purified mouse monoclonal antibody (clone 4F3) reactive to EBOV GP. The antibody detects GP in virus-like particles (VLP) and recombinant GP without the transmembrane region (rGPdTM). It is a monoclonal antibody of the IgG2a isotype. This antibody shows no cross-reactivity to Sudan virus (SUDV) or Marburg Virus (MARV) VLP or MARV rGPdTM. The antibody that is used as the detection antibody in the Zaire Ebola Virus (ZEBOV) GP antigen assay is a protein A-purified neutralizing human monoclonal antibody (KZ52) derived from a human convalescent patient who survived an EBOV infection. KZ52 is directed towards EBOV GP. The antibody detects recombinant EBOV GP without the transmembrane region (EBOV rGPdTM) expressed in both mammalian and insect cells. It is a human variable, human constant of the IgG1 isotype. This antibody shows no cross reactivity against Marburg virus (MARV) GP. The Zaire Ebola Virus (ZEBOV) GP antigen assay is very specific to the envelope bound GP and recombinant insect cell expressed GP with the truncated transmembrane domain and shows no cross reactivity against the soluble GP form which is released into the medium of EBOV-infected cells. This is because KZ52 antibody that is used as detection antibody in the assay binds exclusively to full length GP since the epitope is known to comprise amino acids present in both GP1 and GP2 subunits.

Limit of Blank (LoB):

The cut-off was established as the RLU value at the limit of the blank. Capillary samples were collected in Theranos Nanotainer™ Tubes from in-house subjects. Nanotainer™ Tubes were loaded on ZEBOV GP antigen, field locations cartridges and processed directly on SPU. RLU values were measured from 25 different ZEBOV GP negative capillary samples analyzed on the ZEBOV GP antigen assay. The maximum RLU value from this data set was 9.93. This value was rounded up to set the cut-off at 10 RLU. In other words, any sample greater than 10 RLU, would yield a Cut-off index (COI) of greater than 1.0, and would be classified as equivocal or positive. The equivocal zone and the rationale behind it is considered below.

Limit of Detection (LoD):

Inactivated viral isolate obtained from the CDC was used for determination of LoD. This gamma-irradiated viral stock is prepared from viral supernatant by the CDC from the Zaire Ebolavirus, Mayinga 1976 strain. This inactivated viral stock was reported at $2.5 \times 10^8$ $TCID_{50}$/ml.

K2-EDTA anti-coagulated venous whole blood was aliquoted into Theranos Nanotainer™ tubes. Different concentrations of titered viral stock were spiked into the Nanotainer™ Tube. The Nanotainer™ Tubes were loaded on ZEBOV GP antigen, field locations cartridges and processed directly on SPU. The results are tabulated in Table N-2.

Table N-2 provides a summary of the response of ZEBOV GP antigen assay to serial dilutions of inactivated viral isolate (from CDC).

TABLE N-2

| Virus Strain | Virus Titer ($10^7$ $TCID_{50}$/ml) | No. of positives called | % Positive |
|---|---|---|---|
| ZEBOV, Mayinga 1976 | 25 | 3 | 100 |
| ZEBOV, Mayinga 1976 | 2.5 | 3 | 100 |
| ZEBOV, Mayinga 1976 | 1.25 | 3 | 100 |
| ZEBOV, Mayinga 1976 | 0.83 | 3 | 100 |
| ZEBOV, Mayinga 1976 | 0.625 | 3 | 100 |
| ZEBOV, Mayinga 1976 | 0.500 | 2 | 66 |
| ZEBOV, Mayinga 1976 | 0.417 | 1 | 33 |

The lowest COI for lowest virus titer was 1.5, very close to 1. Based on these data, the tentative LoD is $6.25 \times 10^6$ $TCID_{50}$/ml.

In order to compare this LoD to LoD of a nucleic acid amplification assay and other ELISA assays found in literature, Towner et al (*Journal of Virology*, April 2004, p. 4330-4341) may be considered. Towner et al. studied sequential samples obtained from symptomatic patients during Ebola outbreak in Uganda in 2000-2001. In the Towner et al. study, the authors analyzed a subset of serum samples using a plaque assay (PFU/ml), a Q-RT-PCR assay (copies/ml) and an ELISA ($OD_{sum}$). Comparing the RNA copy number and $OD_{sum}$ (transformed into COI for the authors' assay) measured on the same samples, the following correlation was obtained (See Table N-3):

$$COI_{ELISA} = 0.0012 (RNA\ copies/ml)^{0.44}$$

This correlation implies that the LoD of the ELISA assay ($COI_{ELISA} = 1$) corresponds to $4.45 \times 10^6$ copies RNA/ml. Assuming 1 copy RNA/ml=1 $TCID_{50}$/ml for this virus, we estimate the LoD of the ELISA assay of Towner et al to be $4.45 \times 10^6$ $TCID_{50}$/ml. This number is of the same order as the tentative LoD for the present ZEBOV GP antigen assay determined above using gamma-irradiated inactivated Ebola virus: 1 COI=$6.25 \times 10^6$ copies RNA/ml, and 1 COI≡$2.1 \times 10^3$ PFU/ml. Table N-3 presents a summary of measurements on EBOV clinical samples by different methods from Towner et al. The cut-off of this ELISA assay was set at $OD_{sum} = 0.45$ (http://www.ncbi.nlm.nih.gov/pmc/articles/PMC374287/pdf/1940.pdf).

TABLE N-3

| Sample ID | PFU | RNA | log10(RNA) | $OD_{sum}$ | COI |
|---|---|---|---|---|---|
| 1469 | 5.00E+01 | 2.00E+05 | 5.3 | 0.11 | 0.24 |
| 1522 | 1.50E+04 | 1.80E+07 | 7.3 | 0.82 | 1.82 |
| 1527 | 4.30E+05 | 4.00E+08 | 8.6 | 3.54 | 7.87 |
| 1591 | 1.60E+06 | 3.30E+09 | 9.5 | 7.38 | 16.4 |
| 1612 | 5.30E+05 | 2.50E+08 | 8.4 | 7.46 | 16.60 |

Confirmation of LoD:

LoD of $6.25 \times 10^6$ $TCID_{50}$/ml was confirmed by analyzing 20 more replicates. Capillary samples were collected in Nanotainer™ Tubes from in-house subjects. These samples were spiked with viral isolate to nominally have virus concentration at the LoD. The Nanotainer™ Tubes were loaded on ZEBOV GP antigen, field locations cartridges and processed directly on a SPU. The results obtained from 25 ZEBOV GP negative samples, 6 samples between blank and the LoD, and 23 samples spiked at the LoD were analyzed on the ZEBOV GP antigen assay. Twenty two (22) samples tested positive, i.e. above the cut-off. One sample was in the equivocal zone (discussed below). The LoD of $6.25 \times 10^6$ $TCID_{50}$/ml is thus validated.

Equivocal Zone:

In the zone between the upper limit of the blank (cut-off) and the lower limit of the LoD replicates, the signal is too high to be a true blank, but too low to be called a certain positive. This zone was designated as the equivocal zone. Samples with antigen levels between the blank and the LoD will lie mostly in this zone.

Example 4

Analytical Specificity of the ZEBOV GP Antigen Assay

Reactivity:

Reactivity of the ZEBOV GP antigen assay was evaluated for additional isolates/recombinant antigens of Ebola virus and related families.

As seen in Table N-4, the ZEBOV GP antigen assay does not show reactivity to soluble sGP antigen. The Zaire Ebola Virus (ZEBOV) GP antigen assay is highly specific to the envelope bound GP and the recombinant insect cell expressed GP with the truncated transmembrane domain. This is because KZ52 antibody that is used as detection antibody in the assay binds exclusively to full length GP and the epitope is known to comprise amino acids present in both GP1 and GP2 subunits. This epitope does not exist in sGP. Table N-4 presents reactivity information for the ZEBOV GP antigen assay as disclosed herein.

TABLE N-4

| Strain Tested | Concentration | ZEBOV GP antigen assay results Detected/Not Detected |
| --- | --- | --- |
| ZEBOV culture cell slurry, Mayinga 1976 strain, gamma-irradiated, provided by CDC | Not determined. Cell slurry was used neat | 3/0 |
| ZEBOV, Mayinga 1976 strain. This same material was used for LoD | $2.5 \times 10^8$ TCID$_{50}$/ml | 3/0 |
| sGP, recombinant, spiked | 2.5 ug/ml | 0/3 |
| Reston EBOV GP, recombinant, spiked | 25 ug/ml | 0/1 |
| Sudan EBOV GP, recombinant, spiked | 25 ug/ml | 0/1 |
| ZEBOV VP40, recombinant, spiked | 25 ug/ml | 0/1 |
| Angola MARV GP, recombinant, spiked | 25 ug/ml | 0/1 |
| Bundibugyo EBOV GP, recombinant, spiked | 25 ug/ml | 0/1 |
| Musoke MARV GP, recombinant, spiked | 25 ug/ml | 0/1 |
| ZEBOV NP, recombinant, spiked | 25 ug/ml | 0/1 |

Cross Reactivity:

In order to identify microorganisms that may be expected to be present in blood samples from West Africa travelers, a literature review was undertaken. *Infectious Diseases: A Geographic Guide*, Editor(s): Eskild Petersen, Lin H. Chen, Patricia Schlagenhauf, Wiley was identified as a useful source of information. From this review, a summary of infectious diseases commonly observed in West Africa was compiled; this summary includes the following.

Travelers from West Africa (including Western tourists/businessmen, Africans resident in industrialized countries who return to their country of origin to visit friends and relatives and migrants of African origin) typically present with three conditions: fever, gastroenterological disorders and dermatological problems. Microorganisms observed to be responsible for these conditions are discussed in the following.

Fever: About 3-11% of travelers report occurrence of fever, with up to 50% presenting within first week of return and 96% within 6 months. Fevers are further classified as undifferentiated and differentiated fevers. Undifferentiated fevers include Malaria, *P. falciparum*, and more rarely *P. ovale*, or *P. vivax*. Also rare are Viral hemorrhagic fever (VHF), which may be caused by Marburg, Ebola and Lassa viruses. Differentiated fevers include Fevers with Rash, such as Measles, Rubella, *Neisseria meningitidis, Rickettsia* (rare), Dengue, West Nile, Chikungunya (occasional), Cytomegalovirus, *Toxoplasma*, Schistosomiasis, HIV, and *Treponema Pallidum*. Fevers with Respiratory symptoms include *Streptococcus Pneumoniae, Haemophilius influenzae*, group A *streptococuus*, influenza virus, Tuberculosis, *Ascaris, Strongyloides*, hookworm. Fever with Gastrointestinal symptoms include enteric fever. Fevers with Jaundice include Acute hepatitis (A, B, E), leptospirosis, *Shigella*. Fevers with Neurological symptoms include *Neisseria meningitides, S. pneumonia, H influenzae* type B, enterovirus, herpesviruses. Gastrointestinal disorders include *E. Coli, Salmonella* spp., *Shigella* spp., *Campylobacter*, rotavirus and noroviruses, *Giardia lamblia, Cryptosporidium* spp. Skin conditions include filariasis, guinea worm, mansonellosis, *Mycobacterium ulcerans*.

These conditions were further reviewed to evaluate the probability of observing the causative microorganisms in blood samples during infection. The following organisms were identified as unlikely candidates for appearing in a subject's bloodstream: Measles, Rubella, Schistosomiasis, *Treponema Pallidum*, Influenza Virus, Hookworm, Leptospirosis, *S. pneumonia, H. influenzae* type B, Enterovirus, *E. coli, Salmonella, Campylobacter*, Rotavirus, Norovirus, *Giardia lamblia*, Filariasis, Mansonellosis.

Other cross-reactants are more likely to be present in subject's bloodstream. Within the constraints of availability from commercial sources and lack of ability to culture some of the BSL3/3+/4 micro-organisms, the organisms/proteins listed in Table N-5 were selected for testing.

For cross-reactivity testing, either in-house cultures or commercial cultures with known titers were used. All viruses were spiked at concentrations greater than $10^6$ TCID$_{50}$/ml or at the maximum possible concentration allowed by the available stock. All bacteria were spiked at concentrations greater than $10_6$ CFU/ml or at the maximum possible concentration allowed by the available stock. After spiking, Nanotainer™ Tubes were loaded on ZEBOV GP antigen, field locations cartridges and processed directly on a SPU. Results are summarized in Table N-5 below, which provides a summary of cross-reactivity studies on ZEBOV GP antigen assay.

TABLE N-5

| Virus/Bacteria/Parasite | Strain | Concentration | Units | Results (Detected X/3) |
|---|---|---|---|---|
| Human Rotavirus | Wa | $5 \times 10^6$ | $TCID_{50}$/ml | 0/3 |
| Adenovirus | Serotype 3 | $2 \times 10^7$ | $TCID_{50}$/ml | 0/3 |
| Enterovirus 68 | Fermon | $1 \times 10^5$ | $TCID_{50}$/ml | 0/3 |
| Pseudomonas aeruginosa | Z139 | $1 \times 10^7$ | CFU/ml | 0/3 |
| Streptococcus pneumoniae | Z022 | $1 \times 10^7$ | CFU/ml | 0/3 |
| Hemophilus influenzae | MinnA | $1 \times 10^7$ | CFU/ml | 0/3 |
| Neisseria meningitidis | Serogroup A | $1 \times 10^7$ | CFU/ml | 0/3 |
| Lassa Virus, Recombinant | NP Protein | 100 | ug/ml | 0/3 |
| Rift Valley fever virus, Recombinant | Glycoprotein | 100 | ug/ml | 0/3 |
| Influenza A H3N2 | A/Texas/50/2012 | $1 \times 10^{5.15}$, neat | $TCID_{50}$/ml | 0/3 |
| Influenza B | B/Wisconsin/1/2010 | $1 \times 10^{5.23}$, neat | $TCID_{50}$/ml | 0/3 |
| Salmonella enterica Typhimurium | Z005 | $1.19 \times 10^9$ | CFU/ml | 0/3 |
| Vibrio cholera | Z132 | $1.8 \times 10^9$ | CFU/ml | 0/3 |
| Yersinia enterocolitica | Z036 | $1.16 \times 10^9$ | CFU/ml | 0/3 |
| Shigella boydii | Z131 | $4.63 \times 10^8$ | CFU/ml | 0/3 |
| Plasmodium vivax | South Vietnam | Unknown, neat | | 0/3 |
| Dengue Virus Type 4 | H241 | $1 \times 10^{6.77}$ | $TCID_{50}$/ml | 0/3 |
| Yellow Fever virus (Heat Inactivated) | 17D | $1 \times 10^{5.86}$, neat | $TCID_{50}$/ml | 0/3 |
| Chikungunya (Heat Inactivated) | R80422 | $1 \times 10^{5.86}$, neat | $TCID_{50}$/ml | 0/3 |
| Plasmodium Falciparum Cs Mosaic protein, Recombinant | Source: E. Coli | 100 | ug/ml | 0/3 |
| Plasmodium Falciparum HSP70 protein, Recombinant | Source: E. Coli | 100 | ug/ml | 0/3 |
| Crimean Congo Hemorrhagic Fever virus, Recombinant | NP Protein | 50 | ug/ml | 0/3 |

Interfering Substances:

The impact of potentially interfering substances on the ZEBOV GP antigen assay was evaluated. The evaluation was conducted to demonstrate that the potential interferents do not generate false positive results in known negative specimens, and do not lead to false negative results in known positive specimens.

K2-EDTA anti-coagulated venous samples were collected from in-house subjects. These samples were spiked with interferents at the concentrations recommended by the FDA in the latest guidance. These samples were then aliquoted into 6 Nanotainer™ Tubes. Of these, three Nanotainer™ Tubes were loaded on ZEBOV GP antigen, field locations cartridges and processed directly on a SPU. The remaining 3 were spiked with viral isolate to nominally have virus concentration at the LoD. All samples in Nanotainer™ Tubes were processed directly on a SPU. The results are summarized in Table N-6 (which presents a summary of response of the ZEBOV GP antigen assay to known negative samples spiked with interfering substances) and Table N-7 (which presents a Summary of response of ZEBOV GP antigen assay to known positive samples (at 1×LoD) spiked with interfering substances).

TABLE N-6

| Potential Interfering Substance | Concentration | Results (Detected X/3) |
|---|---|---|
| Hemoglobin | 20 g/dL | 0/3 |
| Bilirubin | 25 mg/dL | 0/3 |
| Intralipids | 1500 mg/dL | 0/3 |
| Serum Protein | 5 g/dL | 0/3 |
| HAMA (human anti-mouse antibody) | 800 ng/ml | 0/3 |
| Rheumatoid Factor | 2000 IU/ml | 2/3 |
| Rheumatoid Factor | 1000 IU/ml | 3/3 |
| Rheumatoid Factor | 500 IU/ml | 3/3 |
| Rheumatoid Factor | 250 IU/ml | 0/3 |
| Rheumatoid Factor | 125 IU/ml | 0/3 |

Interference from Rheumatoid factor was observed at high levels (≥500 IU/ml) which led to increase in observed signal and misclassification of the sample as positive. Therefore, false positive results may be observed for subjects with very high levels of rheumatoid factor. According to a large study performed in Denmark (BMJ 2012; 345:e5244), 250 IU/ml is in the 99.4[th] percentile of the general population, and >95th percentile for the 0.5-2% of the general population suffering from Rheumatoid Arthritis, Sjogren's Syndrome and Lupus. This risk of false positives is thus present in than 0.025%-0.1% of the general population.

TABLE N-7

| Potential Interfering Substance | Concentration | Results (Detected X/3) |
|---|---|---|
| Hemoglobin | 20 g/dL | 3/3 |
| Bilirubin | 25 mg/dL | 3/3 |
| Intralipids | 1500 mg/dL | 3/3 |
| Serum Protein | 5 g/dL | 3/3 |
| Rheumatoid Factor | 2000 IU/ml | 3/3 |

TABLE N-7-continued

| Potential Interfering Substance | Concentration | Results (Detected X/3) |
|---|---|---|
| HAMA (human anti-mouse antibody) | 800 ng/ml | 3/3 |

High Dose Hook Effect:

The data from titration of viral isolate summarized in Table N-2 did not show a high dose hook effect. Due to the fact that viral antigen concentration in the viral isolate could not be increased beyond the neat value, Applicant also used recombinant antigen spikes to verify the non-existence of high dose hook effect. It should be noted that the ZEBOV GP antigen assay uses sequential incubation of the sample and the AP-conjugated detection antibody with a wash in-between. Therefore the existence of a high dose hook effect is extremely unlikely. The data are summarized in Table N-8 below, which presents a summary of concentrations and COI measurements for high dose samples analyzed on ZEBOV GP antigen assay.

TABLE N-8

| Concentration of recombinant GP, uM | COI | Result |
|---|---|---|
| 10.24 | 215 | POS |
| 25.6 | 460 | POS |
| 64 | 672 | POS |
| 160 | 901 | POS |
| 400 | 1579 | POS |
| 1000 | 2161 | POS |
| 2500 | 2270 | POS |

Mock Clinical Study:

In order to establish the performance characteristics of the ZEBOV GP antigen assay, a mock clinical study was conducted.

Samples from 100 individual subjects were analyzed in this study. The 100 samples were divided into two sets: 50 samples were analyzed unspiked by three operators. Twenty-five samples were spiked with the viral isolate at the LoD and then analyzed in triplicate. The remaining twenty-five samples were spiked at (4/3)×, 2×, and 4× the LoD (approximately 8 each) and then analyzed in triplicate (see Table N-9). Since the concentration of the neat viral isolate is only 40×LoD, any spiking concentration greater than 4×LoD will lead to excessive dilution of the whole blood matrix. Three operators processed the samples for this mock clinical study in a blinded fashion. The results of the study are presented in terms of percent agreement with expected results. Table N-9 presents a summary of concentrations used for contriving spiked samples for the mock clinical study.

TABLE N-9

| Final Spiked Concentration ×$10^6$ $TCID_{50}$/ml | x LoD | Number of subjects |
|---|---|---|
| 0 | 0 | 50 |
| 6.25 | 1 | 25 |
| 8.33 | 4/3 | 9 |
| 12.5 | 2 | 8 |
| 25 | 4 | 8 |
| | Total | 100 |

Study Protocol:

a) Capillary samples are collected in 3 Nanotainer™ Tubes from each in-house subject. Venous samples from febrile patients are aliquoted into three Nanotainer™ Tubes. b) Separately, 4 spiking stocks are prepared such that spiking 7 ul of the stock into a Nanotainer™ Tube will yield final concentrations of 0, 1×LoD, 4/3×LoD, 2×LoD and 4×LoD. Spiking stocks are numbered 1 through 4, respectively. c) Each operator was provided with one Nanotainer™ Tube per subject. Each operator was provided cartridges labeled with the number of spiking solution. d) Operators spiked the Nanotainer™ Tubes inside a Biosafety Cabinet, inserted the Nanotainer™ Tube in ZEBOV GP antigen, field locations cartridges and process the sample directly on a SPU. e) In a blinded fashion, the results were analyzed by other members of the analytical staff and then matched with the key.

Data Analysis:

A) For each measurement, the following rules are applied to arrive at the final result:

i. If COI≤1.0, the result is NEGATIVE ii. If COI>1.0 AND COI≤1.6, the result is EQUIVOCAL iii. If COI>1.6, the result is POSITIVE B) For each subject, three measurements are available. If even one of these replicates is discrepant, the subject as a whole is considered discrepant.

C) The results on a per subject basis are compared to expected values and negative and positive percent agreements are calculated, along with exact 95% confidence intervals.

Out of the 100 samples analyzed, 15 were from febrile patients. Of these, 5 were run as negatives and 10 as spiked positives. For one subject spiked at the LoD, one of the replicates tested as EQUIVOCAL, while the other two replicates tested as POSITIVE. This subject has been considered as discrepant. Other subjects were 100% concordant. The percent agreements are summarized in Table N-10 below, which presents a summary of performance of the ZEBOV GP antigen assay in mock clinical study.

TABLE N-10

| | | Expected value | | | |
|---|---|---|---|---|---|
| | | Positive | Equivocal | Negative | Total |
| ZEBOV GP assay | Positive | 49 | 0 | 0 | 49 |
| | Equivocal | 1 | 0 | 0 | 1 |
| | Negative | 0 | 0 | 50 | 50 |
| | Total | 50 | 0 | 50 | 100 |

| Agreement classification | Numerator/ Denominator | Percent Agreement | 95% Confidence Interval |
|---|---|---|---|
| Negative Percent Agreement | 50/50 | 100 | 92.9-100 |
| Positive Percent Agreement | 49/50 | 98 | 89.4-99.9 |

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, and other sub-ranges.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. For example, U.S. Provisional Application Ser. No. 62/061,671 filed Oct. 8, 2014 is fully incorporated herein by reference for all purposes.

While preferred embodiments of the present invention have been shown and described herein, it may be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2014-2015 Thermos, Inc.

What is claimed is:

1. A method for detecting the presence of a virus in a blood sample obtained from a subject, or of detecting prior contact by the subject with said virus, the virus having viral nucleic acid, comprising:
   providing a cartridge with reagents for a nucleic acid assay, an assay for detecting antibodies, and at least two electrolyte assays;
   inserting said cartridge into a sample processing instrument for:
   i) performing said nucleic acid assay for detecting the presence of, or measuring the amount of, the virus in said blood sample obtained from a subject suspected of suffering from the viral disease, the assay comprising contacting a primer complementary to at least a portion of said viral nucleic acid with said sample;
   ii) performing said assay for detecting the presence of, or measuring the amount of, antibodies to the virus, in a sample obtained from a subject suspected of suffering from the viral disease, the assay comprising contacting a viral antigen with said sample; and
   iii) performing said electrolyte assays for measuring the amount of sodium and for measuring the amount of potassium in the blood sample;
   wherein the presence of the virus is detected in the occurrence of detection of viral nucleic acid, or prior contact by the subject with the virus is detected if antibodies to the virus are detected in the sample.

2. The method of claim 1, wherein said blood sample is a fingerstick blood sample.

3. The method of claim 1, wherein said nucleic acid assay comprises an isothermal nucleic acid assay.

4. The method of claim 1, wherein said assay for detecting the presence of, or measuring the amount of, antibodies to the virus, comprises IgM and IgG assays for antibodies to the virus.

5. The method of claim 1, wherein said nucleic acid assay provides results within a short time of less than about 1 hour and said assay for detecting the presence of, or measuring the amount of, antibodies to the virus provides results within a short time of less than about 1 hour.

6. The method of claim 1, wherein said blood sample comprises a sample of EDTA-anti-coagulated whole blood.

7. The method of claim 1, wherein said blood sample comprises a sample of heparin-anti-coagulated plasma.

8. An automatic sample analysis device configured to perform the following method at a point of service location:
   using a cartridge with reagents for a nucleic acid assay, an assay for detecting antibodies, and at least two electrolyte assays;
   inserting said cartridge into the automatic sample analysis device for:
   i) performing a nucleic acid assay for detecting the presence of, or measuring the amount of, the virus in said blood sample obtained from a subject suspected of suffering from the viral disease, the assay comprising contacting a primer complementary to at least a portion of said viral nucleic acid with said sample;

ii) performing an assay for detecting the presence of, or measuring the amount of, antibodies to the virus, in a sample obtained from a subject suspected of suffering from the viral disease, the assay comprising contacting a viral antigen with said sample; and iii) performing electrolyte assays for measuring the amount of sodium and for measuring the amount of potassium in the blood sample;

wherein the presence of the virus is detected in the occurrence of detection of viral nucleic acid, or prior contact by the subject with the virus is detected if antibodies to the virus are detected in the sample.

9. The automatic sample analysis system of claim 8, further comprising a cartridge containing reagents for performing the methods of claim 8.

10. The method of claim 1, wherein steps i to iii are performed using the sample processing instrument using the cartridge comprising:

a first polynucleotide primer and a second polynucleotide primer, wherein the first primer and the second primer are complementary to a nucleotide sequence from the Ebola virus, or to a complementary sequence thereof;

an anti-human IgM antibody;

an anti-human IgG antibody;

an isolated Ebola polypeptide antigen; and an isolated DNA polymerase having strand displacement activity.

11. The cartridge of claim 10, wherein the DNA polymerase is Bstl.

12. The method of claim 10, wherein at least one of the anti-human IgM antibody of the anti-human IgG antibody is immobilized on a solid surface.

13. The method of claim 10, wherein the cartridge further comprises reagents for the detection of one or both of sodium or potassium ions.

14. The method of claim 13, wherein the cartridge comprises β-galactosidase for the detection of sodium ions.

15. The method of claim 13, wherein the cartridge comprises sodium tetraphenylborate for the detection of potassium ions.

16. The method of claim 13, wherein the cartridge comprises β-galactosidase and sodium tetraphenylborate.

17. The method of claim 10, wherein the cartridge further comprises reagents for the detection of one or both of iron or hemoglobin.

18. The method of claim 10, wherein the cartridge further comprises a reagent to render a virus non-infectious.

19. The method of claim 10, wherein the cartridge further comprises an anti-Ebola virus antigen antibody.

20. A method for detecting the presence of a virus in a blood sample obtained from a subject, or of detecting prior contact by the subject with said virus, the virus having viral nucleic acid, comprising:

providing a cartridge with reagents for a nucleic acid assay, an assay for detecting antibodies, and at least two electrolyte assays;

inserting said cartridge into a sample processing instrument for:

i) performing said nucleic acid assay for detecting the presence of, or measuring the amount of, the virus in said blood sample obtained from a subject suspected of suffering from the viral disease, the assay comprising contacting a primer complementary to at least a portion of said viral nucleic acid with said sample;

ii) performing said assay for detecting the presence of, or measuring the amount of, antibodies to the virus, in a sample obtained from a subject suspected of suffering from the viral disease, the assay comprising contacting a viral antigen with said sample; and iii) performing said electrolyte assays for measuring the amount of sodium and for measuring the amount of potassium in the blood sample;

wherein the presence of the virus is detected in the occurrence of detection of viral nucleic acid, or prior contact by the subject with the virus is detected if antibodies to the virus are detected in the sample;

wherein said blood sample is a small volume blood sample having a volume of less than about 250 microliters (μL).

* * * * *

SEQUENCE LISTING

<160> NUMBER OF SEQ ID NOS: 6

<210> SEQ ID NO 1
<211> LENGTH: 18959
<212> TYPE: DNA
<213> ORGANISM: Zaire ebolavirus

<400> SEQUENCE: 1

```
cggacacaca aaaagaaaga agaattttta ggatcttttg tgtgcgaata actatgagga      60
agattaataa tttctctc attgaaattt atatcggaat ttaaattgaa attgttactg       120
taatcacacc tggtttgttt cagagccaca tcacaaagat agagaacaac ctaggtctcc     180
gaagggagca agggcatcag tgtgctcagt tgaaaatccc ttgtcaacac ctaggtctta    240
tcacatcaca agttccacct cagactctgc agggtgatcc aacaacctta atagaaacat    300
tattgttaaa ggacagcatt agttcacagt caaacaagca agattgagaa ttaaccttgg    360
ttttgaactt gaacacttag gggattgaag attcaacaac cctaaagctt ggggtaaaac    420
attggaaata gttaaaagac aaattgctcg gaatcacaaa attccgagta tggattctcg    480
tcctcagaaa atctggatgg cgccgagtct cactgaatct gacatggatt accacaagat    540
cttgacagca ggtctgtccg ttcaacaggg gattgttcgg caaagagtca tcccagtgta    600
tcaagtaaac aatcttgaag aaatttgcca acttatcata caggcctttg aagcaggtgt    660
tgattttcaa gagagtgcgg acagtttcct tctcatgctt tgtcttcatc atgcgtacca    720
gggagattac aaacttttct tggaaagtgg cgcagtcaag tatttggaag ggcacgggtt    780
ccgttttgaa gtcaagaagc gtgatggagt gaagcgcctt gaggaattgc tgccagcagt    840
atctagtgga aaaaacatta agagaacact tgctgccatg ccggaagagg agacaactga    900
agctaatgcc ggtcagtttc tctcctttgc aagtctattc cttccgaaat tggtagtagg    960
agaaaaggct tgccttgaga aggttcaaag gcaaattcaa gtacatgcag agcaaggact   1020
gatacaatat ccaacagctt ggcaatcagt aggacacatg atggtgattt tccgtttgat   1080
gcgaacaaat tttctgatca aatttctcct aatacaccaa gggatgcaca tggttgccgg   1140
```

```
gcatgatgcc aacgatgctg tgatttcaaa ttcagtggct caagctcgtt tttcaggctt    1200
attgattgtc aaaacagtac ttgatcatat cctacaaaag acagaacgag gagttcgtct    1260
ccatcctctt gcaaggaccg ccaaggtaaa aaatgaggtg aactccttta aggctgcact    1320
cagctccctg gccaagcatg gagagtatgc tcctttcgcc cgactttga acctttctgg     1380 agtaaataat cttgagcatg gtcttttccc tcaactatcg gcaattgcac tcggagtcgc    1440
cacagcacac gggagtaccc tcgcaggagt aaatgttgga gaacagtatc aacaactcag    1500
agaggctgcc actgaggctg agaagcaact ccaacaatat gcagagtctc gcgaacttga    1560
ccatcttgga cttgatgatc aggaaaagaa aattcttatg aacttccatc agaaaaagaa    1620
cgaaatcagc ttccagcaaa caaacgctat ggtaactcta agaaaagagc gcctggccaa    1680
gctgacagaa gctatcactg ctgcgtcact gcccaaaaca agtggacatt acgatgatga    1740
tgacgacatt ccctttccag acccatcaa tgatgacgac aatcctggcc atcaagatga     1800
tgatccgact gactcacagg atacgaccat tcccgatgtg gtggttgatc ctgatgatgg    1860
aagctacggc gaataccaga gttactcgga aaacggcatg aatgcaccag atgacttggt    1920
cctattcgat ctagacgagg acgacgagga cactaagcca gtgcctaata gatcgaccaa    1980
gggtggacaa cagaagaaca gtcaaaaggg ccagcatata gagggcagac agacacaatt    2040
caggccaatt caaaatgtcc caggccctca cagaacaatc caccacgcca gtgcgccact    2100
cacggacaat gacagaagaa atgaaccctc cggctcaacc agccctcgca tgctgacacc    2160
aattaacgaa gaggcagacc cactggacga tgccgacgac gagacgtcta gccttccgcc    2220
cttggagtca gatgatgaag agcaggacag ggacggaact tccaaccgca cacccactgt    2280
cgccccaccg gctcccgtat acagagatca ctctgaaaag aaagaactcc cgcaagacga    2340
gcaacaagat caggaccaca ctcaagaggc caggaaccag gacagtgaca cacccagtc    2400 agaacactcc cttgaggaga tgtatcgcca cattctaaga tcacaggggc catttgatgc    2460
tgttttgtat tatcatatga tgaaggatga gcctgtagtt ttcagtacca gtgatggcaa    2520
agagtacacg tatccagact cccttgaaga ggaatatcca ccatggctca ctgaaaaaga    2580
ggctatgaat gaagagaata gatttgttac attggatggt caacaatttt attggccggt    2640
gatgaatcac aagaataaat tcatggcaat cctgcaacat catcagtgaa tgagcatgga    2700
acaatgggat gattcaaccg acaaatagct aacattaagt agtcaaggaa cgaaaacagg    2760
aagaattttt gatgtctaag gtgtgaatta ttatcacaat aaaagtgatt cttattttg     2820 aatttaaagc tagcttatta ttactagccg ttttttcaaag ttcaatttga gtcttaatgc    2880
aaataggcgt taagccacag ttatagccat aattgtaact caatattcta actagcgatt    2940
tatctaaatt aaattacatt atgcttttat aacttaccta ctagcctgcc caacatttac    3000
acgatcgttt tataattaag aaaaaactaa tgatgaagat taaaaccttc atcatcctta    3060
cgtcaattga attctctagc actcgaagct tattgtcttc aatgtaaaag aaaagctggt    3120
ctaacaagat gacaactaga acaaagggca ggggccatac tgcggccacg actcaaaacg    3180
acagaatgcc aggccctgag ctttcgggct ggatctctga gcagctaatg accggaagaa    3240
ttcctgtaag cgacatcttc tgtgatattg agaacaatcc aggattatgc tacgcatccc    3300
aaatgcaaca aacgaagcca aacccgaaga cgcgcaacag tcaaacccaa acggacccaa    3360
tttgcaatca tagttttgag gaggtagtac aaacattggc ttcattggct actgttgtgc    3420
aacaacaaac catcgcatca gaatcattag aacaacgcat tacgagtctt gagaatggtc    3480
```

-continued

```
taaagccagt ttatgatatg caaaaacaa tctcctcatt gaacagggtt tgtgctgaga      3540
tggttgcaaa atatgatctt ctggtgatga caaccggtcg ggcaacagca accgctgcgg      3600
caactgaggc ttattgggcc gaacatggtc aaccaccacc tggaccatca ctttatgaag      3660
aaagtgcgat tcggggtaag attgaatcta gagatgagac cgtccctcaa agtgttaggg      3720
aggcattcaa caatctaaac agtaccactt cactaactga ggaaaatttt gggaaacctg      3780
acatttcggc aaaggatttg agaaacatta tgtatgatca cttgcctggt tttggaactg      3840 cttttccacca attagtacaa gtgatttgta aattgggaaa agatagcaac tcattggaca      3900
tcattcatgc tgagttccag gccagcctgg ctgaaggaga ctctcctcaa tgtgccctaa      3960
ttcaaattac aaaaagagtt ccaatcttcc aagatgctgc tccacctgtc atccacatcc      4020
gctctcgagg tgacattccc cgagcttgcc agaaaagctt gcgtccagtc ccaccatcgc      4080
ccaagattga tcgaggttgg gtatgtgttt ttcagcttca agatggtaaa acacttggac      4140
tcaaaatttg agccaatctc ccttccctcc gaaagaggcg aataatagca gaggcttcaa      4200
ctgctgaact atagggtacg ttacattaat gatacacttg tgagtatcag ccctggataa      4260
tataagtcaa ttaaacgacc aagataaaat tgttcatatc tcgctagcag cttaaaatat      4320
aaatgtaata ggagctatat ctctgacagt attataatca attgttatta agtaacccaa      4380
accaaaagtg atgaagatta agaaaaacct acctcggctg agagagtgtt ttttcattaa      4440
ccttcatctt gtaaacgttg agcaaaattg ttaaaaatat gaggcgggtt atattgccta      4500
ctgctcctcc tgaatatatg gaggccatat accctgtcag gtcaaattca acaattgcta      4560
gaggtggcaa cagcaataca ggcttcctga caccggagtc agtcaatggg gacactccat      4620
cgaatccact caggccaatt gccgatgaca ccatcgacca tgccagccac acaccaggca      4680
gtgtgtcatc agcattcatc cttgaagcta tggtgaatgt catatcgggc cccaaagtgc      4740
taatgaagca aattccaatt tggcttcctc taggtgtcgc tgatcaaaag acctacagct      4800
ttgactcaac tacggccgcc atcatgcttg cttcatacac tatcacccat ttcggcaagg      4860
caaccaatcc acttgtcaga gtcaatcggc tgggtcctgg aatcccggat catcccctca      4920
ggctcctgcg aattggaaac caggcttccc tccaggagtt cgttcttccg ccagtccaac      4980
taccccagta tttcaccttt gatttgacag cactcaaact gatcacccaa ccactgcctg      5040
ctgcaacatg gaccgatgac actccaacag gatcaaatgg agcgttgcgt ccaggaattt      5100
catttcatcc aaaacttcgc cccattcttt tacccaacaa aagtgggaag aaggggaaca      5160
gtgccgatct aacatctccg gagaaaatcc aagcaataat gacttcactc caggacttta      5220
agatcgttcc aattgatcca accaaaaata tcatgggaat cgaagtgcca gaaactctgg      5280
tccacaagct gaccggtaag aaggtgactt ctaaaaatgg acaaccaatc atccctgttc      5340
ttttgccaaa gtacattggg ttggacccgg tggctccagg agacctcacc atggtaatca      5400
cacaggattg tgacacgtgt cattctcctg caagtcttcc agctgtgatt gagaagtaat      5460
tgcaataatt gactcagatc cagttttata gaatcttctc agggatagtg ataacatcta      5520
tttagtaatc cgtccattag aggagacact tttaattgat caatatacta aggtgctttt      5580
acaccattgt cttttttctc tcctaaatgt agaacttaac aaaagactca taatatactt      5640 gttttttaaag gattgattga tgaaagatca taactaataa cattacaaat aatcctacta      5700
taatcaatac ggtgattcaa atgttaatct ttctcattgc atatacttt tgcccttatc      5760 ctcaaattgc ctgcatgctt acatctgagg atagccagtg tgacttggat tggaaatgtg      5820
gagaaaaaat cgggacccat ttctaggttg ttcacaatcc aagtacagac attgcccttc      5880
```

```
taattaagaa aaaatcggcg atgaagatta agccgacagt gagcgtaatc ttcatctctc    5940
ttagattatt tgttttccag agtaggggtc gtcaggtcct tttcaatcgt gtaaccaaaa    6000
taaactccac tagaaggata ttgtggggca acaacacaat gggcgttaca ggaatattgc    6060
agttacctcg tgatcgattc aagaggacat cattctttct tgggtaatt atccttttcc     6120 aaagaacatt ttccatccca cttggagtca tccacaatag cacattacag gttagtgatg    6180
tcgacaaact agtttgtcgt gacaaactgt catccacaaa tcaattgaga tcagttggac    6240
tgaatctcga agggaatgga gtggcaactg acgtgccatc tgcaactaaa agatggggct    6300
tcaggtccgg tgtcccacca aaggtggtca attatgaagc tggtgaatgg gctgaaaact    6360
gctacaatct tgaaatcaaa aaacctgacg ggagtgagtg tctaccagca gcgccagacg    6420
ggattcgggg cttcccccgg tgccggtatg tgcacaaagt atcaggaacg ggaccgtgtg    6480
ccggagactt tgccttccat aaagagggtg ctttcttcct gtatgatcga cttgcttcca    6540
cagttatcta ccgaggaacg actttcgctg aaggtgtcgt tgcatttctg atactgcccc    6600
aagctaagaa ggacttcttc agctcacacc ccttgagaga gccggtcaat gcaacggagg    6660
acccgtctag tggctactat tctaccacaa ttagatatca ggctaccggt tttggaacca    6720
atgagacaga gtacttgttc gaggttgaca atttgaccta cgtccaactt gaatcaagat    6780
tcacaccaca gtttctgctc cagctgaatg agacaatata tacaagtggg aaaaggagca    6840
ataccacggg aaaactaatt tggaaggtca accccgaaat tgatacaaca atcggggagt    6900
gggccttctg ggaaactaaa aaaacctcac tagaaaaatt cgcagtgaag agttgtcttt    6960
cacagttgta tcaaacggag ccaaaaacat cagtggtcag agtccggcgc gaacttcttc    7020
cgacccaggg accaacacaa caactgaaga ccacaaaatc atggcttcag aaaattcctc    7080
tgcaatggtt caagtgcaca gtcaaggaag ggaagctgca gtgtcgcatc taacaaccct    7140
tgccacaatc tccacgagtc cccaatccct cacaaccaaa ccaggtccgg acaacagcac    7200
ccataataca cccgtgtata aacttgacat ctctgaggca actcaagttg aacaacatca    7260
ccgcagaaca gacaacgaca gcacagcctc cgacactccc tctgccacga ccgcagccgg    7320 accccccaaaa gcagagaaca ccaacacgag caagagcact gacttcctgg accccgccac    7380
cacaacaagt ccccaaaacc acagcgagac cgctggcaac aacaacactc atcaccaaga    7440
taccggagaa gagagtgcca gcagcgggaa gctaggctta attaccaata ctattgctgg    7500
agtcgcagga ctgatcacag gcgggagaag aactcgaaga gaagcaattg tcaatgctca    7560
acccaaatgc aaccctaatt tacattactg gactactcag gatgaaggtg ctgcaatcgg    7620
actggcctgg ataccatatt tcgggccagc agccgaggga atttacatag agggctaat    7680 gcacaatcaa gatggtttaa tctgtgggtt gagacagctg ccaacgaga cgactcaagc    7740 tcttcaactg ttcctgagag ccacaactga gctacgcacc ttttcaatcc tcaaccgtaa    7800
ggcaattgat ttcttgctgc agcgatgggg cggcacatgc cacattctgg accggactg    7860 ctgtatcgaa ccacatgatt ggaccaagaa cataacagac aaaattgatc agattattca    7920
tgattttgtt gataaaaccc ttccggacca gggggacaat gacaattggt ggacaggatg    7980
gagacaatgg atacggcag gtattggagt tacaggcgtt ataattgcag ttatcgcttt    8040
attctgtata tgcaaatttg tctttttagtt tttcttcaga ttgcttcatg gaaaagctca    8100
gcctcaaatc aatgaaaacca ggatttaatt atatggatta cttgaatcta agattacttg    8160
acaaatgata atataataca ctggagcttt aaacatagcc aatgtgattc taactccttt    8220
```

```
aaactcacag ttaatcataa acaaggtttg acatcaatct agttatctct tgagaatga      8280 taaacttgat gaagattaag aaaaaggtaa tctttcgatt atctttaatc ttcatccttg      8340
attctacaat catgacagtt gtctttagtg acaagggaaa gaagcctttt tattaagttg      8400
taataatcag atctgcgaac cggtagagtt tagttgcaac ctaacacaca taaagcattg      8460
gtcaaaaagt caatagaaat ttaaacagtg agtggagaca acttttaaat ggaagcttca      8520
tatgagagag gacgcccacg agctgccaga cagcattcaa gggatggaca cgaccaccat      8580
gttcgagcac gatcatcatc cagagagaat tatcgaggtg agtaccgtca atcaaggagc      8640
gcctcacaag tgcgcgttcc tactgtattt cataagaaga gagttgaacc attaacagtt      8700
cctccagcac ctaaagacat atgtccgacc ttgaaaaaag gattttttgtg tgacagtagt     8760 ttttgcaaaa aagatcacca gttggagagt ttaactgata gggaattact cctactaatc      8820
gcccgtaaga cttgtggatc agtagaacaa caattaaata taactgcacc caaggactcg      8880
cgcttagcaa atccaacggc tgatgatttc cagcaagagg aaggtccaaa aattaccttg      8940
ttgacactga tcaagacggc agaacactgg gcgagacaag acatcagaac catagaggat      9000
tcaaaattaa gagcattgtt gactctatgt gctgtgatga cgaggaaatt ctcaaaatcc      9060
cagctgagtc ttttatgtga gacacaccta aggcgcgagg ggcttgggca agatcaggca      9120
gaacccgttc tcgaagtata tcaacgatta cacagtgata aaggaggcag ttttgaagct      9180
gcactatggc aacaatggga ccgacaatcc ctaattatgt ttatcactgc attcttgaat      9240
attgctctcc agttaccgtg tgaaagttct gctgtcgttg tttcagggtt aagaacattg      9300
gttcctcaat cagataatga ggaagcttca accaacccgg ggacatgctc atggtctgat      9360
gagggtaccc cttaataagg ctgactaaaa cactatataa ccttctactt gatcacaata      9420
ctccgtatac ctatcatcat atatttaatc aagacgatat cctttaaaac ttattcagta      9480
ctataatcac tctcgtttca aattaataag atgtgcatga ttgccctaat atatgaagag     9540
gtatgataca acectaacag tgatcaaaga aaatcataat ctcgtatcgc tcgaaatata      9600
acctgccaag catacctctt gcacaaagtg attcttgtac acaaataatg ttttactcta      9660
caggaggtag caacgatcca tcccatcaaa aaataagtat ttcatgactt actaatgatc      9720
tcttaaaata ttaagaaaaa ctgacggaac ataaattctt tatgcttcaa gctgtggagg      9780
aggtgtttgg tattggctat tgttatatta caatcaataa caagcttgta aaaatattgt      9840
tcttgtttca agaggtagat tgtgaccgga aatgctaaac taatgatgaa gattaatgcg      9900
gaggtctgat aagaataaac cttattattc agattaggcc ccaagaggca ttcttcatct      9960 cctttttagca aagtactatt tcagggtagt ccaattagtg gcacgtcttt tagctgtata     10020
tcagtcgccc ctgagatacg ccacaaaagt gtctctaagc taaattggtc tgtacacatc     10080
ccatacattg tattagggc aataatatct aattgaactt agccgtttaa aatttagtgc      10140
ataaatctgg gctaacacca ccaggtcaac tccattggct gaaaagaagc ttacctacaa     10200
cgaacatcac tttgagcgcc ctcacaatta aaaaatagga acgtcgttcc aacaatcgag     10260
cgcaaggttt caaggttgaa ctgagagtgt ctagacaaca aaatattgat actccagaca     10320
ccaagcaaga cctgagaaaa aaccatggct aaagctacgg gacgatacaa tctaatatcg     10380
cccaaaaagg acctggagaa aggggttgtc ttaagcgacc tctgtaactt cttagttagc     10440
caaactattc aggggtggaa ggtttattgg gctggtattg agtttgatgt gactcacaaa     10500
ggaatggccc tattgcatag actgaaaact aatgactttg cccctgcatg gtcaataaca     10560
aggaatctct ttcctcattt atttcaaaat ccgaattcca caattgaatc accgctgtgg     10620
```

```
gcattgagag tcatccttgc agcagggata caggaccagc tgattgacca gtctttgatt    10680
gaacccttag caggagccct tggtctgatc tctgattggc tgctaacaac caacactaac    10740
catttcaaca tgcgaacaca acgtgtcaag gaacaattga gcccaaaaat gctgtcgttg    10800
attcgatcca atattctcaa gtttattaac aaattggatg ctctacatgt cgtgaactac    10860
aacggattgt tgagcagtat tgaaattgga actcaaaatc atataatcat cataactcga    10920
actaacatgg gttttctggt ggagctccaa gaacccgaca atcggcaat gaaccgcatg     10980
aagcctgggc cggcgaaatt ttccctcctt catgagtcca cactgaaagc atttacacaa    11040
ggatcctcga cacgaatgca aagtttgatt cttgaattta atagctctct tgctatctaa    11100
ctaaggtaga atacttcata ttgagctaac tcatatatgc tgactcaata gttatcttga    11160
catctctgct ttcataatca gatatataag cataataaat aaatactcat atttcttgat    11220
aatttgttta accacagata aatcctcact gtaagccagc ttccaagttg acacccttac    11280
aaaaaccagg actcagaatc cctcaaacaa gagattccaa gacaacatca tagaattgct    11340
ttattatatg aataagcatt ttatcaccag aaatcctata tactaaatgg ttaattgtaa    11400
ctgaacccgc aggtcacatg tgttaggttt cacagattct atatattact aactctatac    11460
tcgtaattaa cattagataa gtagattaag aaaaaagcct gaggaagatt aagaaaaact    11520
gcttattggg tctttccgtg ttttagatga agcagttgaa attcttcctc ttgatattaa    11580
atggctacac aacatacccca ataccccagac gctaggttat catcaccaat tgtattggac   11640
caatgtgacc tagtcactag agcttgcggg ttatattcat catactccct taatccgcaa    11700
ctacgcaact gtaaactccc gaaacatatc taccgtttga aatacgatgt aactgttacc    11760
aagttcttga gtgatgtacc agtggcgaca ttgcccatag atttcatagt cccagttctt    11820
ctcaaggcac tgtcaggcaa tggattctgt cctgttgagc cgcggtgcca acagttctta    11880
gatgaaatca ttaagtacac aatgcaagat gctctcttct tgaaatatta tctcaaaaat    11940
gtgggtgctc aagaagactg tgttgatgaa cactttcaag agaaaatctt atcttcaatt    12000
cagggcaatg aatttttaca tcaaatgttt ttctggtatg atctggctat tttaactcga    12060
aggggtagat aaatcgagg aaactctaga tcaacatggt ttgttcatga tgatttaata     12120
gacatcttag gctatgggga ctatgttttt tggaagatcc caatttcaat gttaccactg    12180
aacacacaag gaatccccca tgctgctatg gactggtatc aggcatcagt attcaaagaa    12240
gcggttcaag gcatacaca cattgttttct gtttctactg ccgacgtctt gataatgtgc    12300
aaagatttaa ttcatgtcg attcaacaca actctaatct caaaaatagc agagattgag     12360
gatccagttt gttctgatta tcccaatttt aagattgtgt ctatgcttta ccagagcgga    12420
gattacttac tctccatatt agggtctgat gggtataaaa ttattaagtt cctcgaacca    12480
ttgtgcttgg ccaaaattca attatgctca agtacactg agaggaaggg ccgattctta     12540
acacaaatgc atttagctgt aaatcacacc ctagaagaaa ttacagaaat gcgtgcacta    12600
aagccttcac aggctcaaaa gatccgtgaa ttccatagaa cattgataag gctggagatg    12660
acgccacaac aactttgtga gctatttttcc attcaaaaac actggggggca tcctgtgcta   12720
catagtgaaa cagcaatcca aaaagttaaa aaacatgcta cggtgctaaa agcattacgc    12780
cctatagtga ttttcgagac atactgtgtt tttaaatata gtattgccaa acattatttt    12840
gatagtcaag gatcttggta cagtgttact tcagatagga atctaacacc gggtcttaat    12900
tcttatatca aagaaaatca attccctccg ttgccaatga ttaaagaact actatgggaa    12960
```

```
ttttaccacc ttgaccaccc tccacttttc tcaaccaaaa ttattagtga cttaagtatt    13020
tttataaaag acagagctac cgcagtagaa aggacatgct gggatgcagt attcgagcct    13080
aatgttctag gatataatcc acctcacaaa tttagtacta aacgtgtacc ggaacaattt    13140
ttagagcaag aaaactttc tattgagaat gttctttcct acgcacaaaa actcgagtat    13200
ctactaccac aatatcggaa cttttctttc tcattgaaag agaaagagtt gaatgtaggt    13260
agaaccttcg gaaaattgcc ttatccgact cgcaatgttc aaacactttg tgaagctctg    13320
ttagctgatg gtcttgctaa agcatttcct agcaatatga tggtagttac ggaacgtgag    13380
caaaaagaaa gcttattgca tcaagcatca tggcaccaca caagtgatga ttttggtgaa    13440
catgccacag ttagagggag tagctttgta actgatttag agaaatacaa tcttgcattt    13500
agatatgagt ttacagcacc ttttatagaa tattgcaacc gttgctatgg tgttaagaat    13560 gttttaatt ggatgcatta tacaatccca cagtgttata tgcatgtcag tgattattat    13620
aatccaccac ataaccctca actggagaat cgagacaacc cccccgaagg gcctagttca    13680
tacaggggtc atatgggagg gattgaagga ctgcaacaaa aactctggac aagtatttca    13740
tgtgctcaaa tttctttagt tgaaattaag actggtttta agttacgctc agctgtgatg    13800
ggtgacaatc agtgcattac tgtttatca gtcttcccct tagagactga cgcagacgag    13860
caggaacaga gcgccgaaga caatgcagcg agggtggccg ccagcctagc aaaagttaca    13920
agtgcctgtg gaatctttt aaaacctgat gaaacatttg tacattcagg ttttatctat    13980
tttggaaaaa aacaatattt gaatggggtc caattgcctc agtcccttaa acggctgca    14040 agaatggcac cattgtctga tgcaattttt gatgatcttc aagggaccct ggctagtata    14100
ggcactgctt ttgagcgatc catctctgag acacgacata tctttccttg caggataacc    14160 gcagcttcc atacgttttt ttcggtgaga atcttgcaat atcatcatct cgggttcaat    14220
aaaggttttg accttggaca gttaacactc ggcaaacctc tggatttcgg aacaatatca    14280
ttggcactag cggtaccgca ggtgcttgga gggttatcct tcttgaatcc tgagaaatgt    14340
ttctaccgga atctaggaga tccagttacc tcaggcttat ccagttaaaa aacttatctc    14400
cgaatgattg agatggatga tttattctta cctttaattg cgaagaaccc tgggaactgc    14460
actgccattg actttgtgct aaatcctagc ggattaaatg tccctgggtc gcaagactta    14520
acttcatttc tgcgccagat tgtacgcagg accatcaccc taagtgcgaa aaacaaactt    14580
attaatacct tatttcatgc gtcagctgac ttcgaagacg aaatggtttg taaatggcta    14640
ttatcatcaa ctcctgttat gagtcgtttt gcggccgata tcttttcacg cacgccgagc    14700
gggaagcgat tgcaaattct aggataccg gaaggaacac gcacattatt agcctctaag    14760
atcatcaaca ataatacaga gacaccggtt ttggacagac tgaggaaaat aacattgcaa    14820
aggtggagcc tatggtttag ttatcttgat cattgtgata atatcctggc ggaggcttta    14880
acccaaataa cttgcacagt tgatttagca cagattctga gggaatattc atgggctcat    14940
attttagagg gaagacctct tattggagcc acactcccat gtatgattga gcaattcaaa    15000
gtgttttggc tgaaacccta cgaacaatgt ccgcagtgtt caaatgcaaa gcaaccaggt    15060
gggaaaccat tcgtgtcagt ggcagtcaag aaacatattg ttagtgcatg gccgaacgca    15120
tcccgaataa gctggactat cggggatgga atcccataca ttggatcaag gacagaagat    15180
aagataggac aacctgctat taaaccaaaa tgtccttccg cagccttaag agaggccatt    15240
gaattggcgt cccgtttaac atgggtaact caaggcagtt cgaacagtga cttgctaata    15300
aaaccatttt tggaagcacg agtaaattta agtgttcaag aaatacttca aatgaccct    15360
```

```
tcacattact caggaaatat tgttcacagg tacaacgatc aatacagtcc tcattctttc   15420
atggccaatc gtatgagtaa ttcagcaacg cgattgattg tttctacaaa cactttaggt   15480
gagttttcag gaggtggcca gtctgcacgc gacagcaata ttattttcca gaatgttata   15540
aattatgcag ttgcactgtt cgatattaaa tttagaaaca ctgaggctac agatatccaa   15600
tataatcgtg ctcaccttca tctaactaag tgttgcaccc gggaagtacc agctcagtat   15660
ttaacataca catctacatt ggatttagat ttaacaagat accgagaaaa cgaattgatt   15720
tatgacagta atcctctaaa aggaggactc aattgcaata tctcattcga taatccattt   15780
ttccaaggta aacggctgaa cattatagaa gatgatctta ttcgactgcc tcacttatct   15840
ggatgggagc tagccaagac catcatgcaa tcaattattt cagatagcaa caattcatct   15900
acagacccaa ttagcagtgg agaaacaaga tcattcacta cccatttctt aacttatccc   15960
aagataggac ttctgtacag ttttggggcc tttgtaagtt attatcttgg caatacaatt   16020
cttcggacta gaaaattaac acttgacaat tttttatatt acttaactac tcaaattcat   16080
aatctaccac atcgctcatt gcgaatactt aagccaacat tcaaacatgc aagcgttatg   16140
tcacggttaa tgagtattga tcctcatttt tctatttaca taggcggtgc tgcaggtgac   16200
agaggactct cagatgcggc caggttattt ttgagaacgt ccatttcatc ttttcttaca   16260
tttgtaaaag aatggataat taatcgcgga acaattgtcc ctttatggat agtatatccg   16320
ctagagggtc aaaacccaac acctgtgaat aattttctct atcagatcgt agaactgctg   16380
gtgcatgatt catcaagaca acaggctttt aaaactacca taagtgatca tgtacatcct   16440
cacgacaatc ttgtttacac atgtaagagt acagccagca atttcttcca tgcatcattg   16500
gcgtactgga ggagcagaca cagaaacagc aaccgaaaat acttggcaag agactcttca   16560
actggatcaa gcacaaacaa cagtgatggt catattgaga gaagtcaaga acaaaccacc   16620
agagatccac atgatggcac tgaacggaat ctagtcctac aaatgagcca tgaaataaaa   16680
agaacgacaa ttccacaaga aaacacgcac cagggtccgt cgttccagtc ctttctaagt   16740
gactctgctt gtggtacagc aaatccaaaa ctaaatttcg atcgatcgag acacaatgtg   16800
aaatttcagg atcataactc ggcatccaag agggaaggtc atcaaataat ctcacaccgt   16860
ctagtcctac ctttctttac attatctcaa gggacacgcc aattaacgtc atccaatgag   16920
tcacaaaccc aagacgagat atcaaagtac ttacggcaat tgagatccgt cattgatacc   16980
acagtttatt gtagatttac cggtatagtc tcgtccatgc attacaaact tgatgaggtc   17040
ctttgggaaa tagagagttt caagtcggct gtgacgctag cagagggaga aggtgctggt   17100
gccttactat tgattcagaa ataccaagtt aagaccttat ttttcaacac gctagctact   17160
gagtccagta tagagtcaga aatagtatca ggaatgacta ctcctaggat gcttctacct   17220
gttatgtcaa aattccataa tgaccaaatt gagattattc ttaacaactc agcaagccaa   17280
ataacagaca taacaaatcc tacttggttt aaagaccaaa gagcaaggct acctaagcaa   17340
gtcgaggtta taaccatgga tgcagagaca acagagaata taaacagatc gaaattgtac   17400
gaagctgtat ataaattgat cttacaccat attgatccta gcgtattgaa agcagtggtc   17460
cttaaagtct ttctaagtga tactgagggt atgttatggc taaatgataa tttagccccg   17520 tttttttgcca ctggttattt aattaagcca ataacgtcaa gtgctagatc tagtgagtgg   17580
tatctttgtc tgacgaactt cttatcaact acacgtaaga tgccacacca aaaccatctc   17640
agttgtaaac aggtaatact tacggcattg caactgcaaa ttcaacgaag cccatactgg   17700
```

| | |
|---|---|
| ctaagtcatt taactcagta tgctgactgt gagttacatt taagttatat ccgccttggt | 17760 |
| tttccatcat tagagaaagt actataccac aggtataacc tcgtcgattc aaaaagaggt | 17820 |
| ccactagtct ctatcactca gcacttagca catcttagag cagagattcg agaattaact | 17880 |
| aatgattata atcaacagcg acaaagtcgg actcaaacat atcactttat tcgtactgca | 17940 |
| aaaggacgaa tcacaaaact agtcaatgat tatttaaaat tctttcttat tgtgcaagca | 18000 |
| ttaaaacata atgggacatg gcaagctgag tttaagaaat taccagagtt gattagtgtg | 18060 |
| tgcaataggt tctaccatat tagagattgc aattgtgaag aacgtttctt agttcaaacc | 18120 |
| ttatatttac atagaatgca ggattctgaa gttaagctta tcgaaaggct gacagggctt | 18180 |
| ctgagtttat ttccggatgg tctctacagg tttgattgaa ttaccgtgca tagtatcctg | 18240 |
| atacttgcaa aggttggtta ttaacataca gattataaaa aactcataaa ttgctctcat | 18300 |
| acatcatatt gatctaatct caataaacaa ctatttaaat aacgaaagga gtccctatat | 18360 |
| tatatactat atttagcctc tctccctgcg tgataatcaa aaaattcaca atgcagcatg | 18420 |
| tgtgacatat tactgccgca atgaatttaa cgcaacataa taaactctgc actctttata | 18480 |
| attaagcttt aacgaaaggt ctgggctcat attgttattg atataataat gttgtatcaa | 18540 |
| tatcctgtca gatggaatag tgttttggtt gataacacaa cttcttaaaa caaaattgat | 18600 |
| ctttaagatt aagttttta taattatcat tactttaatt tgtcgtttta aaacggtga | 18660 |
| tagccttaat ctttgtgtaa aataagagat taggtgtaat aaccttaaca tttttgtcta | 18720 |
| gtaagctact atttcataca gaatgataaa attaaaagaa aaggcaggac tgtaaaatca | 18780 |
| gaaataccct ctttacaata tagcagacta gataataatc ttcgtgttaa tgataattaa | 18840 |
| gacattgacc acgctcatca gaaggctcgc cagaataaac gttgcaaaaa ggattcctgg | 18900 |
| aaaaatggtc gcacacaaaa atttaaaaat aaatctattt cttcttttt gtgtgtcca | 18959 |

<210> SEQ ID NO 2
<211> LENGTH: 3021
<212> TYPE: DNA
<213> ORGANISM: Zaire ebolavirus

<400> SEQUENCE: 2

| | |
|---|---|
| cggacacaca aaagaaaga agaattttta ggatcttttg tgtgcgaata actatgagga | 60 |
| agattaataa ttttcctctc attgaaattt atatcggaat ttaaattgaa attgttactg | 120 |
| taatcacacc tggtttgttt cagagccaca tcacaaagat agagaacaac ctaggtctcc | 180 |
| gaagggagca agggcatcag tgtgctcagt tgaaaatccc ttgtcaacac ctaggtctta | 240 |
| tcacatcaca agttccacct cagactctgc agggtgatcc aacaacctta atagaaacat | 300 |
| tattgttaaa ggacagcatt agttcacagt caaacaagca agattgagaa ttaaccttgg | 360 |
| ttttgaactt gaacacttag gggattgaag attcaacaac cctaaagctt ggggtaaaac | 420 |
| attggaaata gttaaaagac aaattgctcg gaatcacaaa attccgagta tggattctcg | 480 |
| tcctcagaaa atctggatgg cgccgagtct cactgaatct gacatggatt accacaagat | 540 |
| cttgacagca ggtctgtccg ttcaacaggg gattgttcgg caaagagtca tcccagtgta | 600 |
| tcaagtaaac aatcttgaag aaatttgcca acttatcata caggcctttg aagcaggtgt | 660 |
| tgattttcaa gagagtgcgg acagtttcct tctcatgctt tgtcttcatc atgcgtacca | 720 |
| gggagattac aaacttttct tggaaagtgg cgcagtcaag tatttggaag gcacgggtt | 780 |
| ccgttttgaa gtcaagaagc gtgatggagt gaagcgcctt gaggaattgc tgccagcagt | 840 |
| atctagtgga aaaaacatta agagaacact tgctgccatg ccggaagagg agacaactga | 900 |

| | |
|---|---|
| agctaatgcc ggtcagtttc tctcctttgc aagtctattc cttccgaaat tggtagtagg | 960 |
| agaaaaggct tgcttgagga aggttcaaag gcaaattcaa gtacatgcag agcaaggact | 1020 |
| gatacaatat ccaacagctt ggcaatcagt aggacacatg atggtgattt tccgtttgat | 1080 |
| gcgaacaaat tttctgatca aatttctcct aatacaccaa gggatgcaca tggttgccgg | 1140 |
| gcatgatgcc aacgatgctg tgatttcaaa ttcagtggct caagctcgtt tttcaggctt | 1200 |
| attgattgtc aaaacagtac ttgatcatat cctacaaaag acagaacgag gagttcgtct | 1260 |
| ccatcctctt gcaaggaccg ccaaggtaaa aaatgaggtg aactccctta aggctgcact | 1320 |
| cagctccctg gccaagcatg gagagtatgc tcctttcgcc cgacttttga acctttctgg | 1380 |
| agtaaataat cttgagcatg gtcttttccc tcaactatcg gcaattgcac tcggagtcgc | 1440 |
| cacagcacac gggagtaccc tcgcaggagt aaatgttgga gaacagtatc aacaactcag | 1500 |
| agaggctgcc actgaggctg agaagcaact ccaacaatat gcagagtctc gcgaacttga | 1560 |
| ccatcttgga cttgatgatc aggaaaagaa aattcttatg aacttccatc agaaaaagaa | 1620 |
| cgaaatcagc ttccagcaaa caaacgctat ggtaactcta agaaaagagc gcctggccaa | 1680 |
| gctgacagaa gctatcactg ctgcgtcact gcccaaaaca agtggacatt acgatgatga | 1740 |
| tgacgacatt ccctttccag gacccatcaa tgatgacgac aatcctggcc atcaagatga | 1800 |
| tgatccgact gactcacagg atacgaccat tcccgatgtg gtggttgatc ccgatgatgg | 1860 |
| aagctacggc gaataccaga gttactcgga aaacggcatg aatgcaccag atgacttggt | 1920 |
| cctattcgat ctagacgagg acgacgagga cactaagcca gtgcctaata gatcgaccaa | 1980 |
| gggtggacaa cagaagaaca gtcaaaaggg ccagcatata gagggcagac agacacaatc | 2040 |
| caggccaatt caaaatgtcc caggccctca gaacaatcc caccacgcca gtgcgccact | 2100 |
| cacggacaat gacagaagaa atgaaccctc cggctcaacc agccctcgca tgctgacacc | 2160 |
| aattaacgaa gaggcagacc cactggacga tgccgacgac gagacgtcta gccttccgcc | 2220 |
| cttggagtca gatgatgaag agcaggacag ggacggaact tccaaccgca cacccactgt | 2280 |
| cgccccaccg gctcccgtat acagagatca ctctgaaaag aaagaactcc cgcaagacga | 2340 |
| gcaacaagat caggaccaca ctcaagaggc caggaaccag gacagtgaca cacccagtc | 2400 |
| agaacactct tttgaggaga tgtatcgcca cattctaaga tcacggggc catttgatgc | 2460 |
| tgttttgtat tatcatatga tgaaggatga gcctgtagtt ttcagtacca gtgatggcaa | 2520 |
| agagtacacg tatccagact cccttgaaga ggaatatcca ccatggctca ctgaaaaaga | 2580 |
| ggctatgaat gaagagaata gatttgttac attggatggt caacaatttt attggccggt | 2640 |
| gatgaatcac aagaataaat tcatggcaat cctgcaacat catcagtgaa tgagcatgga | 2700 |
| acaatgggat gattcaaccg acaaatagct aacattaagt agtcaaggaa cgaaaacagg | 2760 |
| aagaattttt gatgtctaag gtgtgaatta ttatcacaat aaaagtgatt cttattttg | 2820 |
| aatttaaagc tagccttatt attactagcc gttttcaaa gttcaatttg agtcttaatg | 2880 |
| caaataggcg ttaagccaca gttatagcca taattgtaac tcaatattct aactagcgat | 2940 |
| ttatctaaat taaattacat tatgctttta taacttacct actagcctgc ccaacattta | 3000 |
| cacgatcgtt ttataattaa g | 3021 |

<210> SEQ ID NO 3
<211> LENGTH: 2408
<212> TYPE: DNA
<213> ORGANISM: Zaire ebolavirus

<400> SEQUENCE: 3

```
gcgatgaaga ttaagccgac agtgagcgta atcttcatct ctcttagatt atttgttttc      60
cagagtaggg gtcgtcaggt cctttcaat cgtgtaacca aaataaactc cactagaagg     120
atattgtggg gcaacaacac aatgggcgtt acaggaatat tgcagttacc tcgtgatcga     180
ttcaagagga catcattctt tctttgggta attatccttt tccaaagaac attttccatc     240
ccacttggag tcatccacaa tagcacatta caggttagtg atgtcgacaa actagtttgt     300
cgtgacaaac tgtcatccac aaatcaattg agatcagttg gactgaatct cgaagggaat     360
ggagtggcaa ctgacgtgcc atctgcaact aaaagatggg gcttcaggtc cggtgtccca     420
ccaaaggtgg tcaattatga agctggtgaa tgggctgaaa actgctacaa tcttgaaatc     480
aaaaaacctg acgggagtga gtgtctacca gcagcgccag acgggattcg ggcttcccc      540
cggtgccggt atgtgcacaa agtatcagga acggaccgt gtgccggaga ctttgccttc     600
cataaagagg gtgctttctt cctgtatgat cgacttgctt ccacagttat ctaccgagga     660
acgactttcg ctgaaggtgt cgttgcattt ctgatactgc cccaagctaa gaaggacttc     720
ttcagctcac accccttgag agagccggtc aatgcaacgg aggacccgtc tagtggctac     780
tattctacca caattagata tcaggctacc ggttttggaa ccaatgagac agagtacttg     840
ttcgaggttg acaatttgac ctacgtccaa cttgaatcaa gattcacacc acagtttctg     900
ctccagctga atgagacaat atatacaagt gggaaaagga gcaataccac gggaaaacta     960
atttggaagg tcaaccccga aattgataca acaatcgggg agtgggcctt ctgggaaact    1020
aaaaaaccct cactagaaaa attcgcagtg aagagttgtc tttcacagtt gtatcaaacg    1080
gagccaaaaa catcagtggt cagagtccgg cgcgaacttc ttccgaccca gggaccaaca    1140
caacaactga agaccacaaa atcatggctt cagaaaattc ctctgcaatg gttcaagtgc    1200
acagtcaagg aagggaagct gcagtgtcgc atctaacaac ccttgccaca atctccacga    1260
gtccccaatc cctcacaacc aaaccaggtc cggacaacag cacccataat acaccgtgt     1320
ataaacttga catctctgag gcaactcaag ttgaacaaca tcaccgcaga acagacaacg    1380
acagcacagc ctccgacact ccctctgcca cgaccgcagc cggacccca aaagcagaga     1440
acaccaacac gagcaagagc actgacttcc tggaccccgc caccacaaca agtccccaaa    1500
accacagcga accgctggc aacaacaaca ctcatcacca agataccgga gaagagagtg     1560
ccagcagcgg gaagctaggc ttaattacca atactattgc tggagtcgca ggactgatca    1620
caggcgggag aagaactcga agagaagcaa ttgtcaatgc tcaacccaaa tgcaacccta    1680
atttacatta ctggactact caggatgaag gtgctgcaat cggactggcc tggataccat    1740
atttcgggcc agcagccgag ggaatttaca tagaggggct aatgcacaat caagatggtt    1800
taatctgtgg gttgagacag ctggccaacg agacgactca agctcttcaa ctgttcctga    1860
gagccacaac tgagctacgc accttttcaa tcctcaaccg taaggcaatt gatttcttgc    1920
tgcagcgatg gggcggcaca tgccacattc tgggaccgga ctgctgtatc gaaccacatg    1980
attggaccaa gaacataaca gacaaaattg atcagattat tcatgatttt gttgataaaa    2040
cccttccgga ccaggggac aatgacaatt ggtggacagg atggagacaa tggataccgg    2100
caggtattgg agttacaggc gttataattg cagttatcgc tttattctgt atatgcaaat    2160
ttgtctttta gttttctc agattgcttc atggaaaagc tcagcctcaa atcaatgaaa    2220
ccaggattta attatatgga ttacttgaat ctaagattac ttgacaaatg ataatataat    2280
acactggagc tttaaacata gccaatgtga ttctaactcc tttaaactca cagttaatca    2340
```

-continued

```
taaacaaggt tgacatcaa tctagttatc tctttgagaa tgataaactt gatgaagatt    2400
aagaaaaa                                                            2408
```

<210> SEQ ID NO 4
<211> LENGTH: 739
<212> TYPE: PRT
<213> ORGANISM: Zaire ebolavirus

<400> SEQUENCE: 4

```
Met Asp Ser Arg Pro Gln Lys Ile Trp Met Ala Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Pro Ala Val Ser Ser Gly Lys
        115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Arg Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Leu Lys Ala Ala Leu Ser Ser Leu Ala
        275                 280                 285

Lys His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350
```

Gln Leu Gln Gln Tyr Ala Glu Ser Arg Glu Leu Asp His Leu Gly Leu
            355                 360                 365
Asp Asp Gln Glu Lys Lys Ile Leu Met Asn Phe His Gln Lys Lys Asn
370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Ala Ala Ser Leu Pro Lys
                405                 410                 415
Thr Ser Gly His Tyr Asp Asp Asp Asp Ile Pro Phe Pro Gly Pro
            420                 425                 430
Ile Asn Asp Asp Asp Asn Pro Gly His Gln Asp Asp Asp Pro Thr Asp
            435                 440                 445
Ser Gln Asp Thr Thr Ile Pro Asp Val Val Asp Pro Asp Asp Gly
    450                 455                 460
Ser Tyr Gly Glu Tyr Gln Ser Tyr Ser Glu Asn Gly Met Asn Ala Pro
465                 470                 475                 480
Asp Asp Leu Val Leu Phe Asp Leu Asp Glu Asp Asp Glu Asp Thr Lys
                485                 490                 495
Pro Val Pro Asn Arg Ser Thr Lys Gly Gly Gln Gln Lys Asn Ser Gln
            500                 505                 510
Lys Gly Gln His Ile Glu Gly Arg Gln Thr Gln Ser Arg Pro Ile Gln
            515                 520                 525
Asn Val Pro Gly Pro His Arg Thr Ile His His Ala Ser Ala Pro Leu
            530                 535                 540
Thr Asp Asn Asp Arg Arg Asn Glu Pro Ser Gly Ser Thr Ser Pro Arg
545                 550                 555                 560
Met Leu Thr Pro Ile Asn Glu Glu Ala Asp Pro Leu Asp Asp Ala Asp
                565                 570                 575
Asp Glu Thr Ser Ser Leu Pro Pro Leu Glu Ser Asp Asp Glu Glu Gln
            580                 585                 590
Asp Arg Asp Gly Thr Ser Asn Arg Thr Pro Thr Val Ala Pro Pro Ala
            595                 600                 605
Pro Val Tyr Arg Asp His Ser Glu Lys Lys Glu Leu Pro Gln Asp Glu
            610                 615                 620
Gln Gln Asp Gln Asp His Thr Gln Glu Ala Arg Asn Gln Asp Ser Asp
625                 630                 635                 640
Asn Thr Gln Ser Glu His Ser Phe Glu Glu Met Tyr Arg His Ile Leu
                645                 650                 655
Arg Ser Gln Gly Pro Phe Asp Ala Val Leu Tyr Tyr His Met Met Lys
            660                 665                 670
Asp Glu Pro Val Val Phe Ser Thr Ser Asp Gly Lys Glu Tyr Thr Tyr
            675                 680                 685
Pro Asp Ser Leu Glu Glu Glu Tyr Pro Pro Trp Leu Thr Glu Lys Glu
690                 695                 700
Ala Met Asn Glu Glu Asn Arg Phe Val Thr Leu Asp Gly Gln Gln Phe
705                 710                 715                 720
Tyr Trp Pro Val Met Asn His Lys Asn Lys Phe Met Ala Ile Leu Gln
                725                 730                 735
His His Gln

<210> SEQ ID NO 5
<211> LENGTH: 739
<212> TYPE: PRT
<213> ORGANISM: Zaire ebolavirus

```
<400> SEQUENCE: 5

Met Asp Ser Arg Pro Gln Lys Ile Trp Met Ala Pro Ser Leu Thr Glu
1               5                   10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Leu Pro Ala Val Ser Ser Gly Lys
        115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Lys His Gly Glu Tyr Ala Pro Phe Ala Arg Leu Leu Asn Leu Ser Gly
290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
        355                 360                 365

Asp Asp Gln Glu Lys Lys Ile Leu Met Asn Phe His Gln Lys Lys Asn
370                 375                 380

Glu Ile Ser Phe Gln Gln Thr Asn Ala Met Val Thr Leu Arg Lys Glu
385                 390                 395                 400

Arg Leu Ala Lys Leu Thr Glu Ala Ile Thr Ala Ala Ser Leu Pro Lys
```

```
                    405                 410                 415
Thr Ser Gly His Tyr Asp Asp Asp Asp Ile Pro Phe Pro Gly Pro
            420                 425                 430

Ile Asn Asp Asp Asn Pro Gly His Gln Asp Asp Pro Thr Asp
            435                 440                 445

Ser Gln Asp Thr Thr Ile Pro Asp Val Val Asp Pro Asp Asp Gly
            450                 455                 460

Ser Tyr Gly Glu Tyr Gln Ser Tyr Ser Glu Asn Gly Met Asn Ala Pro
465                 470                 475                 480

Asp Asp Leu Val Leu Phe Asp Leu Asp Glu Asp Glu Asp Thr Lys
            485                 490                 495

Pro Val Pro Asn Arg Ser Thr Lys Gly Gly Gln Gln Lys Asn Ser Gln
            500                 505                 510

Lys Gly Gln His Ile Glu Gly Arg Gln Thr Gln Ser Arg Pro Ile Gln
            515                 520                 525

Asn Val Pro Gly Pro His Arg Thr Ile His His Ala Ser Ala Pro Leu
            530                 535                 540

Thr Asp Asn Asp Arg Arg Asn Glu Pro Ser Gly Ser Thr Ser Pro Arg
545                 550                 555                 560

Met Leu Thr Pro Ile Asn Glu Glu Ala Asp Pro Leu Asp Asp Ala Asp
                565                 570                 575

Asp Glu Thr Ser Ser Leu Pro Pro Leu Glu Ser Asp Asp Glu Glu Gln
                580                 585                 590

Asp Arg Asp Gly Thr Ser Asn Arg Thr Pro Thr Val Ala Pro Pro Ala
            595                 600                 605

Pro Val Tyr Arg Asp His Ser Glu Lys Lys Glu Leu Pro Gln Asp Glu
            610                 615                 620

Gln Gln Asp Gln Asp His Thr Gln Glu Ala Arg Asn Gln Asp Ser Asp
625                 630                 635                 640

Asn Thr Gln Ser Glu His Ser Phe Glu Glu Met Tyr Arg His Ile Leu
                645                 650                 655

Arg Ser Gln Gly Pro Phe Asp Ala Val Leu Tyr Tyr His Met Met Lys
                660                 665                 670

Asp Glu Pro Val Val Phe Ser Thr Ser Asp Gly Lys Glu Tyr Thr Tyr
            675                 680                 685

Pro Asp Ser Leu Glu Glu Glu Tyr Pro Pro Trp Leu Thr Glu Lys Glu
            690                 695                 700

Ala Met Asn Glu Glu Asn Arg Phe Val Thr Leu Asp Gly Gln Gln Phe
705                 710                 715                 720

Tyr Trp Pro Val Met Asn His Lys Asn Lys Phe Met Ala Ile Leu Gln
                725                 730                 735

His His Gln

<210> SEQ ID NO 6
<211> LENGTH: 676
<212> TYPE: PRT
<213> ORGANISM: Zaire ebolavirus

<400> SEQUENCE: 6

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
```

```
                35                  40                  45
Asp Lys Leu Val Cys Arg Asp Lys Leu Ser Ser Thr Asn Gln Leu Arg
 50                  55                  60

Ser Val Gly Leu Asn Leu Glu Gly Asn Gly Val Ala Thr Asp Val Pro
65                   70                  75                  80

Ser Ala Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
290                 295                 300

Glu Leu Ser Phe Thr Val Val Ser Asn Gly Ala Lys Asn Ile Ser Gly
305                 310                 315                 320

Gln Ser Pro Ala Arg Thr Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
450                 455                 460
```

-continued

```
His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
        610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675
```